United States Patent
Sholev et al.

(10) Patent No.: US 9,820,754 B2
(45) Date of Patent: Nov. 21, 2017

(54) CIRCULAR BONE TUNNELING DEVICE EMPLOYING A STABILIZING ELEMENT

(75) Inventors: Mordehai Sholev, Moshav Amikam (IL); Gilad Lavi, Rishon Lezion (IL); Raphael Meloul, Shilo (IL); Ronen Raz, Magal (IL)

(73) Assignee: MININVASIVE LTD., Magal (IL)

( * ) Notice: Subject to any disclaimer, the term of this patent is extended or adjusted under 35 U.S.C. 154(b) by 647 days.

(21) Appl. No.: 14/240,082

(22) PCT Filed: Aug. 23, 2012

(86) PCT No.: PCT/IL2012/000319
§ 371 (c)(1),
(2), (4) Date: Apr. 9, 2014

(87) PCT Pub. No.: WO2013/027210
PCT Pub. Date: Feb. 28, 2013

(65) Prior Publication Data
US 2014/0214038 A1    Jul. 31, 2014

Related U.S. Application Data

(60) Provisional application No. 61/526,717, filed on Aug. 24, 2011, provisional application No. 61/584,267, (Continued)

(51) Int. Cl.
*A61B 17/16* (2006.01)
*A61B 17/04* (2006.01)
(Continued)

(52) U.S. Cl.
CPC ...... *A61B 17/1604* (2013.01); *A61B 17/0401* (2013.01); *A61B 17/0482* (2013.01);
(Continued)

(58) Field of Classification Search
CPC ........................... A61B 17/16; A61B 17/1604
(Continued)

(56) References Cited

U.S. PATENT DOCUMENTS 2,579,192 A   12/1951   Kohl
5,250,055 A   10/1993   Moore et al.
(Continued)

FOREIGN PATENT DOCUMENTS

CN   101193600   9/2010
EP   1898812     3/2008
(Continued)

OTHER PUBLICATIONS

An English translation of an Office Action dated Mar. 24, 2015, which issued during the prosecution of Japanese Patent Application No. 519213/2013.
(Continued)

*Primary Examiner* — Christopher Beccia
(74) *Attorney, Agent, or Firm* — Sughrue Mion, PLLC

(57) ABSTRACT

The present invention provides a circular bone tunneling device, comprising: a hollow elongate body comprising a hollow elongate body head, said hollow elongate body head defining a rigid circular arc, comprising a surgical needle; an extendable and retractable support element, reconfigurable from an extended configuration to a retracted configuration; said support element, in said extended configuration, adapted to be located along said path formed by said rigid circular arc; said support element and said hollow elongate body head are adapted to grasp said bone from at least two points along the circumference of said bone; a stabilizing element.

8 Claims, 65 Drawing Sheets

Related U.S. Application Data filed on Jan. 8, 2012, provisional application No. 61/636,751, filed on Apr. 23, 2012.

(51) Int. Cl.
   *A61B 17/88* (2006.01)
   *A61B 17/06* (2006.01)
   *A61B 17/29* (2006.01)
   *A61B 17/00* (2006.01)

(52) U.S. Cl.
   CPC ...... *A61B 17/0483* (2013.01); *A61B 17/1642* (2013.01); *A61B 17/8861* (2013.01); *A61B 17/06061* (2013.01); *A61B 2017/0046* (2013.01); *A61B 2017/00398* (2013.01); *A61B 2017/0404* (2013.01); *A61B 2017/0427* (2013.01); *A61B 2017/06042* (2013.01); *A61B 2017/2923* (2013.01)

(58) Field of Classification Search
   USPC .......................................................... 606/79
   See application file for complete search history.

(56) References Cited

U.S. PATENT DOCUMENTS

| | | | |
|---|---|---|---|
| 5,387,221 | A | 2/1995 | Bisgaard |
| 5,499,991 | A | 3/1996 | Garman et al. |
| 5,665,096 | A | 9/1997 | Yoon |
| 5,681,333 | A | 10/1997 | Burkhart et al. |
| 5,961,530 | A | 10/1999 | Moore |
| 6,328,744 | B1 | 12/2001 | Harari |
| 6,443,963 | B1 | 9/2002 | Baldwin |
| 6,523,417 | B1 | 2/2003 | Donahue |
| 7,029,479 | B2 | 4/2006 | Tallarida |
| 7,097,648 | B1 | 8/2006 | Globerman et al. |
| 7,166,116 | B2 | 1/2007 | Lizardi et al. |
| 7,662,171 | B2 | 2/2010 | West, Jr. |
| 8,282,657 | B2 | 10/2012 | McClurg et al. |
| 2002/0040227 | A1 | 4/2002 | Harari |
| 2003/0078599 | A1 | 4/2003 | O'Quinn |
| 2006/0195121 | A1 | 8/2006 | Chu |
| 2006/0271060 | A1 | 11/2006 | Gordon |
| 2007/0005067 | A1 | 1/2007 | Dross |
| 2007/0179509 | A1 | 8/2007 | Nagata et al. |
| 2008/0109015 | A1 | 5/2008 | Chu et al. |
| 2008/0228224 | A1 | 9/2008 | Sauer |
| 2009/0012538 | A1 | 1/2009 | Saliman et al. |
| 2009/0062819 | A1 | 3/2009 | Burkhart |
| 2009/0069823 | A1 | 3/2009 | Foerster |
| 2009/0105729 | A1* | 4/2009 | Zentgraf ............ A61B 17/0469 606/139 |
| 2009/0105743 | A1 | 4/2009 | Chu |
| 2009/0131956 | A1 | 5/2009 | Dewey |
| 2009/0138029 | A1 | 5/2009 | Saliman et al. |
| 2009/0312782 | A1 | 12/2009 | Park |
| 2010/0076436 | A1 | 3/2010 | Hajianpour |
| 2010/0106194 | A1 | 4/2010 | Bonutti et al. |
| 2010/0152751 | A1* | 6/2010 | Meade ............... A61B 17/0469 606/144 |
| 2010/0191248 | A1 | 7/2010 | Mehta et al. |
| 2010/0198258 | A1 | 8/2010 | Heaven et al. |
| 2010/0318139 | A1 | 12/2010 | Beauchamp |
| 2011/0022063 | A1 | 1/2011 | McClurg |
| 2011/0106124 | A1* | 5/2011 | Beauchamp ....... A61B 17/0482 606/170 |
| 2012/0239085 | A1 | 9/2012 | Schlotterback et al. |
| 2012/0323248 | A1 | 12/2012 | Dross |
| 2013/0123810 | A1 | 5/2013 | Brown et al. |
| 2013/0178854 | A1 | 7/2013 | Sholev et al. |
| 2014/0219483 | A1 | 8/2014 | Hong |
| 2014/0303625 | A1 | 10/2014 | Sholev |

FOREIGN PATENT DOCUMENTS

| | | |
|---|---|---|
| EP | 1970016 | 9/2008 |
| EP | 2698128 | 2/2014 |
| JP | 1996-033635 | 2/1996 |
| JP | 1996-509918 | 10/1996 |
| JP | 2003-501132 | 1/2003 |
| JP | 2008-510526 | 4/2008 |
| JP | 2008-546489 | 12/2008 |
| WO | 96/27331 | 9/1996 |
| WO | 97/47246 | 12/1997 |
| WO | 00/74578 | 12/2000 |
| WO | 02/07609 | 1/2002 |
| WO | 2009/107121 | 9/2009 |
| WO | 2010/056785 | 5/2010 |
| WO | 2010/056786 | 5/2010 |
| WO | 2010/056787 | 5/2010 |
| WO | 2011/160166 | 12/2011 |
| WO | 2012/007941 | 1/2012 |
| WO | 2013/027209 | 2/2013 |
| WO | 2013/027210 | 2/2013 |
| WO | 2013/071234 | 5/2013 |
| WO | 2013/102909 | 7/2013 |
| WO | 2014/147619 | 9/2014 |

OTHER PUBLICATIONS

An Office Action dated Feb. 18, 2016 which issued during the prosecution of Australian Patent Application No. 2012298197.
An International Search Report and a Written Opinion both dated Mar. 10, 2016, which issued during the prosecution of Applicant's PCT/IL2015/050923.
European Search Report dated Jun. 11, 2015 which issued during the prosecution of Applicant's European App No. 12826407.4.
An Office Action dated Jul. 11, 2016 which issued during the prosecution of Australian Patent Application No. 2012298197.
An International Search Report and a Written Opinion both dated Jun. 9, 2016, which issued during the prosecution of Applicant's PCT/IL2015/050978.
An Office Action dated Jun. 27, 2016, which issued during the prosecution of Australian Patent Application No. 2015202032.
An Office Action dated May 24, 2016 which issued during the prosecution of Chinese Patent Application No. 2013800124154.
European Search Report dated Jan. 27, 2016 which issued during the prosecution of Applicant's European App No. 13733888.
An Invitation to pay additional fees dated Dec. 23, 2015, which issued during the prosecution of Applicant's PCT/IL2015/050923.
An Office Action dated Jan. 5, 2016, which issued during the prosecution of Japanese Patent Application No. 2013-519213.
An Office Action dated Feb. 25, 2016, which issued during the prosecution of U.S. Appl. No. 13/809,562.
An Office Action dated Nov. 22, 2016 which issued during the prosecution of Japanese Patent Application No. 550801/2014.
Translation of Notice of Reasons for Refusal, mailed Sep. 6, 2016, issued in corresponding JP Application No. 2014-526597, 5 pages in English.
An Office Action dated Mar. 21, 2017, which issued during the prosecution of U.S. Appl. No. 14/240,227.
European Search Report dated Jan. 17, 2017, which issued during the prosecution of Applicant's European App No. 14769413.7.
European Search Report dated May 11, 2017, which issued during the prosecution of Applicant's European App No. 11806391.6.
U.S. Appl. No. 61/636,751, filed Apr. 23, 2012.
U.S. Appl. No. 61/584,267, filed Jan. 8, 2012.
U.S. Appl. No. 61/526,717, filed Aug. 24, 2011.
U.S. Appl. No. 61/363,247, filed Jul. 11, 2010.
U.S. Appl. No. 61/714,813, filed Oct. 17, 2012.
An International Search Report and a Written Opinion both dated Jan. 23, 2013, which issued during the prosecution of Applicant's PCT/IL2012/000318.
An International Search Report and a Written Opinion both dated Dec. 5, 2011, which issued during the prosecution of Applicant's PCT/IL2011/000549.

(56) References Cited

OTHER PUBLICATIONS

An International Search Report and a Written Opinion both dated May 10, 2013 which issued during the prosecution of Applicant's PCT/IL2013/050030.
An International Search Report dated Jan. 8, 2013 which issued during the prosecution of Applicant's PCT/IL2012/000319.
An English translation of an Office Action dated Jul. 3, 2014 which issued during the prosecution of Chinese Patent Application 2011800437287.
An International Search Report and Written Opinion both dated Jul. 11, 2014, which issued during the prosecution of Applicant's PCT/IL 14/50299.
An International Preliminary Search Report dated Aug. 26, 2014, which issued during the prosecution of Applicant's PCT/IL2013/050030.
An International Preliminary Report dated Feb. 25, 2014 which issued during the prosecution of Applicant's PCT/IL2012/000319.
Written Opinion dated Jan. 8, 2013 which issued during the prosecution of Applicant's PCT/IL2012/000319.
An International Preliminary Report dated Feb. 25, 2014 which issued during the prosecution of Applicant's PCT/IL2012/000318.
An Office Action dated Apr. 5, 2014 which issued during the prosecution of Australian Patent Application No. 2011277949.

* cited by examiner

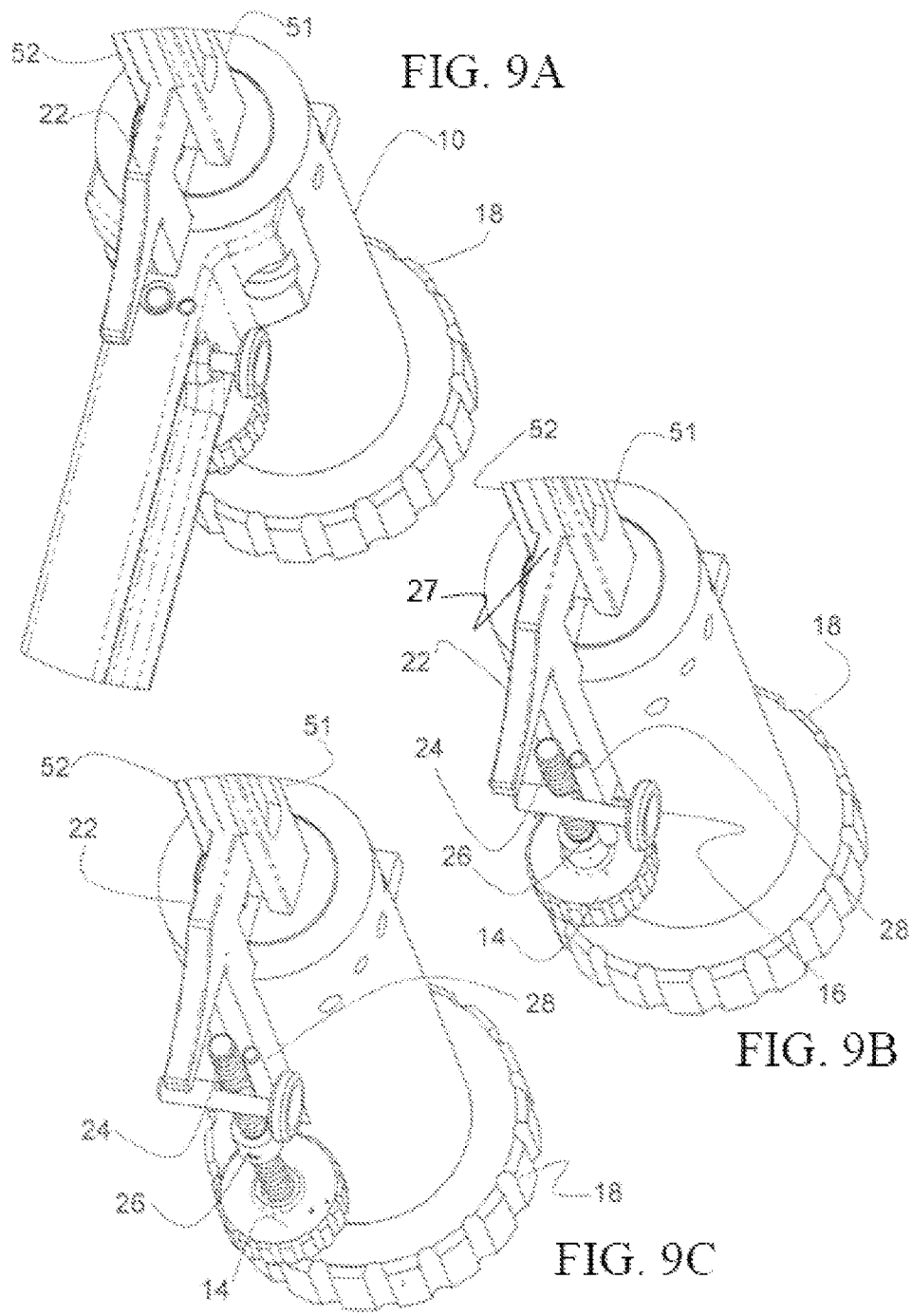

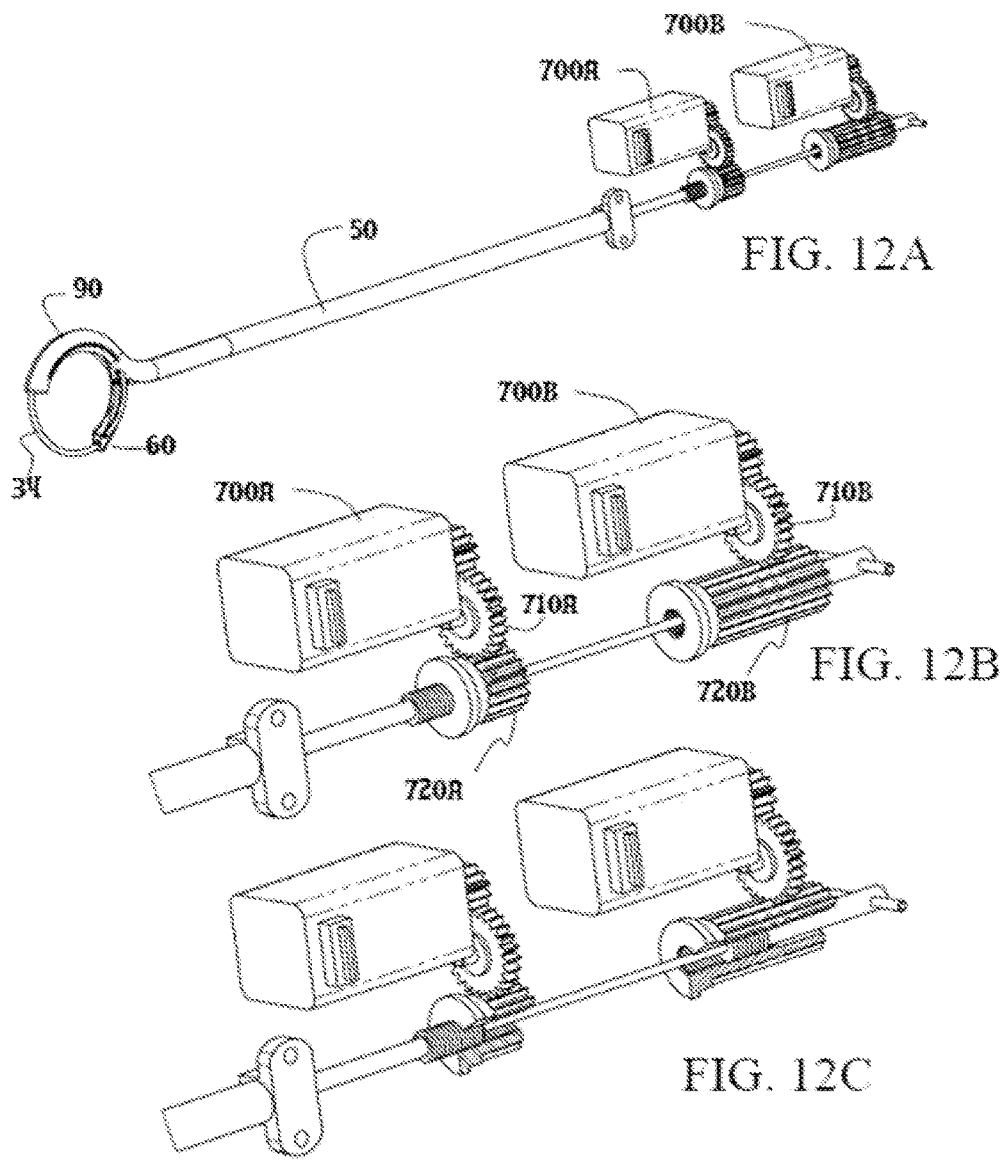

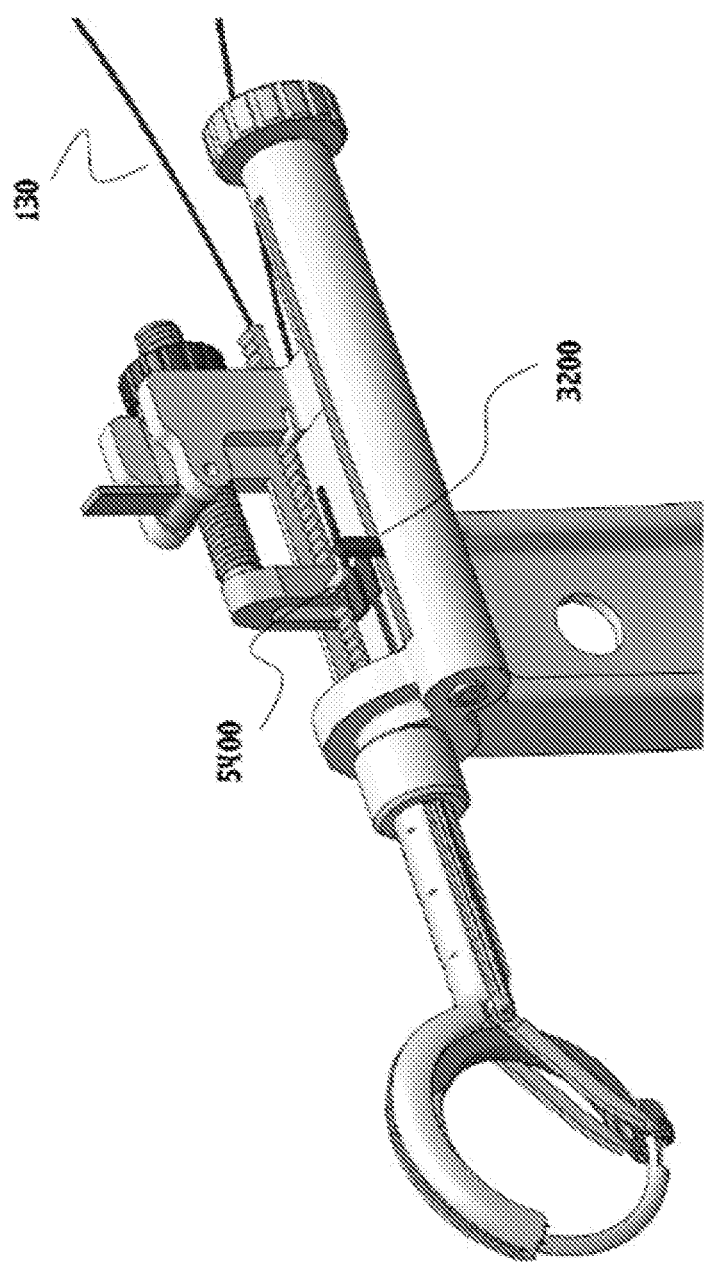

CIRCULAR BONE TUNNELING DEVICE EMPLOYING A STABILIZING ELEMENT

CROSS REFERENCE TO RELATED APPLICATIONS

This application is a National Stage of International Application No. PCT/IL2012/000319 filed Aug. 23, 2012, claiming priorities based on U.S. Provisional Patent Application Nos. 61/526,717, filed Aug. 24, 2011, 61/584,267, filed Jan. 8, 2012, and 61/636,751, filed Apr. 23, 2012, the contents of all of which are incorporated herein by reference in their entirety.

FIELD OF THE INVENTION

This invention generally relates to a bone tunneling device and an adjustable suture passer for use in arthroscopic surgery. Specifically, it relates to suture passers that are capable of passing a suture by transosseous technique through a bone directly without need for drilling through the bone.

The present invention provides an adjustable suture passer, adapted to create a transosseous tunnel and enable passage of a suture through a bone while grasping the circumference of the same.

In other words the present invention provides a bone tunneling device that partially encompasses and firmly holds the bone at two different contact points along an arc and is further stabilized by a stabilizing element that reduces the movement (degrees of freedom) of the device by fixating the device to the bone at a third contact point such that movement is minimized preventing rotation around the first two contact points. The additional fixation point can prevent inadvertent movement by the physician due to minor hand movements during surgical procedures.

BACKGROUND OF THE INVENTION

Reattachment of a ligament to a bone in arthroscopic procedures such as, for example, repair of a torn rotator cuff typically involves two steps. First, an anchor is inserted into the bone. Then, the ligament is attached to the bone by passing a suture through the ligament tissue and then through the anchor, thereby tying the ligament to the bone.

There are several drawbacks to this method. First, two separate actions must be performed in order to attach the ligament to the bone, namely, insertion of the anchor into the bone and suturing of the ligament. The necessary involvement of at least two separate sets of tools inherently complicates the surgical procedure, when compared to performing the procedure while using a single tool.

In addition, placement of the anchor may require drilling into the bone, which creates debris that must be removed and can increase the stress on the bone. The procedures described above often require large access ports and/or open surgery to enable the positioning and actuation of the required tools.

Methods that do not require an anchor generally require creation of a plurality of bores in the bone. U.S. Pat. No. 6,523,417 discloses a method for suturing soft tissue to a bone in which a hole is drilled into the bone and a slit cut into it. PCT Pat. Application WO09/107121 discloses a method of suturing soft tissue to a bone in which two bores are made in the bone at an angle, preferably 70°. PCT Pat. Applications WO10/056785, WO10/056786, and WO10/056787 disclose suture anchoring systems in which two orthogonal bores are made in the bone. A major disadvantage of these methods is that the presence of a plurality of bores at an angle significantly weakens the bone, increasing the likelihood of later injury, fractures and eventually weakening of the bone. The main disadvantage in said publication is that these methods require highly invasive surgery in order to allow access and actuation of tools used in the procedure.

U.S. Pat. No. 6,328,744 discloses a bone suturing device in which a needle enters a bone at a non-perpendicular angle and a curved path due to the force exerted on the needle by a hinged handle. In preferred embodiments of the invention, a second needle is used as well and the bore created from two sides. While the purpose of the second needle is to increase the pressure used by the first needle to enter the bone rather than to push the bone away, the amount of stabilization actually performed by the second needle is limited because the two needles enter the bone from the same side. Thus. It is a long felt need to provide a device which will enable stable fixation of the needle tunneling device to the targeted bone surface in order to create an arched transosseous tunnel without drilling in a minimally invasive surgical procedure.

There is thus a long-felt need for a device that supports the bone from a side other than that through which the needle enters and can enable direct attachment of the ligament and the bone by passing the suture through the bone without any need for a separate anchor or for drilling holes such as two orthogonal holes in the bone.

Yet more, it is a further long-felt need for a transosseous tunneling device that is adapted to pass a suture through transosseous tunnel so as to provide said attachment of ligament to the bone.

Yet more, it is a further long felt need to provide a tool that can be applied to the bone surface through a small minimally invasive incision and then be converted into a second larger profile that enables fixation to a bone surface along the path of an arc within the bone without enlargement of the access incision point.

SUMMARY OF THE INVENTION

It is therefore one object to provide a circular bone tunneling device for use in arthroscopic surgery, comprising: a hollow elongate body comprising a hollow elongate body head, said a hollow elongate body head defining a rigid circular arc; said hollow elongate body head comprising a surgical needle adapted to tunnel through a bone along a path formed by said rigid circular arc; and, an extendable and retractable support element, reconfigurable from at least one extended configuration to at least one retracted configuration; said support element, in said extended configuration is adapted to be located along said path formed by said rigid circular arc; said support element, in said extended configuration, and said hollow elongate body head are adapted to grasp said bone from at least two points along the circumference of said bone; a stabilizing element reconfigurable from at least one extended configuration to at least one retracted configuration; wherein said stabilizing element in said extended configuration is adapted to be in physical contact with said bone so as to reversibly fixate the orientation of said circular bone tunneling device relative to said bone.

It is another object of the present invention to provide the circular bone tunneling device as defined above, wherein said stabilizing element is adapted to reciprocally move along the main longitudinal axis of said circular bone tunneling device so as to be reconfigured from said extended configuration to said retracted configuration and vice versa.

It is another object of the present invention to provide the circular bone tunneling device as defined above, wherein said stabilizing element is pivotally coupled, at a pivot point, to the distal end of said hollow elongate body at a pivot point of said circular bone tunneling device.

It is another object of the present invention to provide the circular bone tunneling device as defined above, wherein said stabilizing element is adapted to radially and pivotably rotate around said pivot point so as to be reconfigured from said extended configuration to said retracted configuration and vice versa.

It is another object of the present invention to provide the circular bone tunneling device as defined above, wherein said stabilizing element in said extended configuration is adapted to be reversibly anchored within said bone.

It is another object of the present invention to provide the circular bone tunneling device as defined above, wherein said stabilizing element comprises a distal end and a proximal end; said distal end comprises a flange and a tip; said tip is adapted to penetrate said bone and to reversibly anchor said stabilizing element within the same.

It is another object of the present invention to provide the circular bone tunneling device as defined above, said flange is adapted to limit the insertion of said distal end of said stabilizing element into said bone such that only said tip is anchored within said bone.

It is another object of the present invention to provide the circular bone tunneling device as defined above, wherein the shape of said tip of said stabilizing element is selected from a group consisting of nail-like tip, screw-like tip and any combination thereof.

It is another object of the present invention to provide the circular bone tunneling device as defined above, wherein said stabilizing element comprises at least one marker, adapted to indicate to the user as for said stabilizing element position with respect to the bone.

It is another object of the present invention to provide the circular bone tunneling device as defined above, wherein said device further comprises an indicator said indicator is provided with a yardstick having numerical references on the same; said numerical references are adapted to indicate to the user the depth of penetration of said stabilizing element into said the bone.

It is another object of the present invention to provide the circular bone tunneling device as defined above, additionally comprising a locking mechanism adapted to lock said stabilizing element in the desired position.

It is another object of the present invention to provide the circular bone tunneling device as defined above, additionally comprising at least one suture cartridge comprising a suture; said suture is adapted to be passed through said circular transosseous tunnel previously tunneled through said bone.

It is another object of the present invention to provide the circular bone tunneling device as defined above, wherein said suture cartridge comprising an external scaffold enclosing an inner body throughout which a surgical tool is inserted.

It is another object of the present invention to provide the circular bone tunneling device as defined above, wherein said inner body is characterized by having diameter of at least 3 mm.

It is another object of the present invention to provide the circular bone tunneling device as defined above, wherein said surgical tool is selected from a group consisting of grasper, tendon holder, scissors, diathermy, scalpel, stapler, jig, suturing means, said stabilizing element and any combination thereof.

It is another object of the present invention to provide the circular bone tunneling device as defined above, further comprising a shaft, parallel to said device's main longitudinal axis; wherein said hollow elongate body head located at the distal end of said shaft and defining said rigid circular arc with the concave side of said arc forming said underside of said hollow elongate body head.

It is another object of the present invention to provide the circular bone tunneling device as defined above, wherein said shaft additionally comprising an inner elongated hollow tube throughout which a surgical tool is inserted.

It is another object of the present invention to provide the circular bone tunneling device as defined above, wherein said inner elongated hollow tube is characterized by having diameter of at least 3 mm.

It is another object of the present invention to provide the circular bone tunneling device as defined above, wherein said suture cartridge is coupled to said shaft and adapted to reciprocally move along the main longitudinal axis of the same.

It is another object of the present invention to provide the circular bone tunneling device as defined above, wherein said support element comprises at least one hook adapted to encase said suture.

It is another object of the present invention to provide the circular bone tunneling device as defined above, wherein said movement of said suture cartridge in the direction of said support element loads said suture onto said hook of said support element.

It is another object of the present invention to provide the circular bone tunneling device as defined above, wherein said surgical needle is a rigid surgical needle.

It is another object of the present invention to provide the circular bone tunneling device as defined above, wherein said surgical needle is either straight or curved and shaped as circular arc.

It is another object of the present invention to provide the circular bone tunneling device as defined above, wherein said needle is adapted to engage with said support element once said needle has tunneled through and exited said bone along said arced path.

It is another object of the present invention to provide the circular bone tunneling device as defined above, wherein said needle comprises catching means adapted to catch and encase said suture once said needle engages with said support member.

It is another object of the present invention to provide the circular bone tunneling device as defined above, wherein said catching means are selected from a group consisting of mechanical means, magnetically, electrical means or any combination thereof.

It is another object of the present invention to provide the circular bone tunneling device as defined above, wherein said mechanical means are at least one hook adapted to encase said suture once said needle engages with said support member.

It is another object of the present invention to provide the circular bone tunneling device as defined above, wherein said needle comprises at least one hook adapted to encase said suture once said needle engages with said support member.

It is another object of the present invention to provide the circular bone tunneling device as defined above, wherein said extendable and retractable support element (54) is attached to the distal end of said shaft and structured and configured such that when said support element is extended, it opposes the underside of said curved hollow elongate body head and its distal end is located along the path formed by said rigid circular arc.

It is another object of the present invention to provide the circular bone tunneling device as defined above, wherein said hollow elongate body head comprising an arc-like shaft along which said support member is guided along tracks so as to be reconfigured to said extended configuration.

It is another object of the present invention to provide the circular bone tunneling device as defined above, additionally comprising a support element driving mechanism, adapted, upon activation of a support element control, to drive the motion of said support element.

It is another object of the present invention to provide the circular bone tunneling device as defined above, wherein upon activation of said support element, the same is extended, such that said bone is being grasped by and between said extendable and retractable support element and said head.

It is another object of the present invention to provide the circular bone tunneling device as defined above, wherein the distal end of said hollow elongate body head comprises an orifice through which a rigid circular hollow tube passes through.

It is another object of the present invention to provide the circular bone tunneling device as defined above, wherein the extendable and retractable support element is adapted to reach, upon various degrees of extension, predetermined locations relative to the distal end of said rigid circular hollow tube, such that the distance between said distal end of said rigid circular hollow tube and the upper side of said support element provides a slip fit over a bone through which a suture is to be passed.

It is another object of the present invention to provide the circular bone tunneling device as defined above, additionally comprising a handle (12).

It is another object of the present invention to provide the circular bone tunneling device as defined above, wherein said handle is either a reusable handle or a single use handle.

It is another object of the present invention to provide the circular bone tunneling device as defined above, wherein said arthroscopic surgery is performed without the need of drilling through said bone.

It is another object of the present invention to provide the circular bone tunneling device as defined above, wherein said hollow elongate body comprises: at least one track (522) disposed within said hollow elongate body; a connecting wire (132) forming a loop within said hollow elongate body, the proximal end of said loop physically connected to said rigid circular hollow tube control mechanism; a distal slidable member (4) disposed within said track and adapted to slide within said track while maintaining said needle and one leg of said loop formed by said connecting wire to pass through said hollow elongate body unhindered, said distal slidable member comprising a substantially flat distal edge; and a channel (206) passing through said distal slidable member through which the second leg of said loop formed by said connecting wire passes; a plurality of additional slidable members (2) disposed within said track and adapted to slide along it while allowing said needle and one leg of said loop formed by said connecting wire to pass through said hollow elongate body unhindered, each of said additional slidable members comprising a channel passing through said distal slidable member through which the second leg of said loop formed by said connecting wire passes; and a rigid circular hollow tube actuator (6) disposed within said body proximally to the most proximally located slidable member, said activator disposed so as to engage said rigid circular hollow tube control; wherein said slidable members provide a constant tool profile during said arthroscopic surgery.

It is another object of the present invention to provide the circular bone tunneling device as defined above, wherein said slidable members (2, 4) have the shape of a cylinder with an indentation (204, 404) about its circumference, said channel (206) passing through said cylinder within indentation substantially perpendicular to the longitudinal axis of said cylinder.

It is another object of the present invention to provide the circular bone tunneling device as defined above, wherein said handle comprises a distally located movable segment (12A) and a proximally located stationary segment (12B), said movable segment in physical connection with said support element driving mechanism.

It is another object of the present invention to provide the circular bone tunneling device as defined above, further incorporating indicating means for indicating the movement, along said arc, of said rigid circular hollow tube.

It is another object of the present invention to provide the circular bone tunneling device as defined above, wherein said indicating means comprise
  a window disposed on one side of said shaft; and,
  an indicator located within said shaft, physically connected to said rigid circular hollow tube's driving mechanism such that the distance through which said indicator travels is proportional to the distance the distal end of said rigid circular hollow tube travels, and disposed such that at least part of the travel of said indicator is visible through said window.

It is another object of the present invention to provide the circular bone tunneling device as defined above, further comprising a mark on said side of said shaft in which said window is disposed, said mark is located such that when said indicator reaches said mark, the distal end of said rigid circular hollow tube is fully extended.

It is another object of the present invention to provide the circular bone tunneling device as defined above, additionally comprising a needle control adapted to control the forward and reverse movement of said needle along said path.

It is another object of the present invention to provide the circular bone tunneling device as defined above, wherein said needle control comprises a rotatable knob (18) in communication with said needle such that the forward and reverse movement of needle is proportional to the rotation of said rotatable handle.

It is another object of the present invention to provide the circular bone tunneling device as defined above, wherein said needle control imparts sufficient force to said needle such that the same is provided with sufficient force to penetrate bone.

It is another object of the present invention to provide the circular bone tunneling device as defined above, wherein said sufficient force is in the range of about 500 to about 600 Newton.

It is another object of the present invention to provide the circular bone tunneling device as defined above, wherein said hollow elongate body further comprises at least one body slot (330) along at least part of its length, said hollow elongate body head further comprising at least one hollow elongate body head slot (390) along at least part of its length, and said rigid circular hollow tube's driving mechanism comprises:

a rigid circular hollow tube actuator (6) physically connected to said rigid circular hollow tube control, said rigid circular hollow tube actuator disposed within said elongate hollow body and adapted to slide along the proximal-distal axis of said hollow body; and, a yoke (300) disposed external to said hollow elongate body, said yoke pivotably connected substantially at its proximal end to said rigid circular hollow tube actuator via a connection that passes through said body slot (330) and at pivotably connected substantially at its distal end to said rigid circular hollow tube via a connection that passes through said hollow elongate body head slot (390).

It is another object of the present invention to provide the circular bone tunneling device as defined above, wherein said support element driving mechanism comprises an actuator (58) adapted to reconfigure said support element to said retracted configuration to said extended configuration and vice versa.

It is another object of the present invention to provide the circular bone tunneling device as defined above, wherein said support element driving mechanism comprises a yoke (340) pivotably connected at its proximal end to said actuator (58) and pivotably connected to said support element.

It is another object of the present invention to provide the circular bone tunneling device as defined above, wherein at least one selected from a group consisting of said support element, said needle and any combination thereof is actuated mechanically by a motor.

It is another object of the present invention to provide the circular bone tunneling device as defined above, wherein said needle is characterized by having cross sectional area selected from a group consisting of circular, triangular, rectangular, flat or any combination thereof.

It is another object of the present invention to provide the circular bone tunneling device as defined above, additionally comprising a retractable sleeve characterized by having at least two positions (a) an extended position, in which said sleeve completely encircles said needle; and, (b) retracted position, in which said needle partially protrudes out of said retractable sleeve.

It is another object of the present invention to provide the circular bone tunneling device as defined above, additionally comprising at least one anchor, in mechanical communication with said suture.

It is another object of the present invention to provide the circular bone tunneling device as defined above, wherein said needle is adapted to engage with said anchor so as to encase said suture.

It is another object of the present invention to provide the circular bone tunneling device as defined above, wherein said engagement of said suture with said anchor forms at least one loop.

It is another object of the present invention to provide the circular bone tunneling device as defined above, wherein n additional sutures are interleaved and threaded through said loop; n is an integer greater than 1.

It is another object of the present invention to provide a method for tunneling through a bone during arthroscopic surgery, said method comprising steps of:
  a. providing a curved bone tunneling device comprising:
    a hollow elongate body comprising a hollow elongate body head, said a hollow elongate body head defining a rigid circular arc; said hollow elongate body head comprising a surgical needle adapted to tunnel through a bone along a path formed by said rigid circular arc; an extendable and retractable support element, reconfigurable from at least one extended configuration to at least one retracted configuration; and, a stabilizing element reconfigurable from at least one extended configuration to at least one retracted configuration; wherein said stabilizing element in said extended configuration, is adapted to be in physical contact with said bone so as to reversibly fixate the orientation of said circular bone tunneling device relative to said bone;
  b. positioning said hollow elongate body of said device adjacent to the circumference of a bone;
  c. fixating said needle to said bone;
  d. extending said retractable support element to a location along the path formed by said circular arc; thereby grasping said bone with said support element and said hollow elongate body at two points along the circumference of said bone;
  e. extending said stabilizing element so as to reconfigure the same from said retracted configuration to said extended configuration; thereby reversibly fixating the orientation of said curved bone tunneling device relative to said bone;
  f. actuating said needle, thereby tunneling through said bone along said circular arc path;
  g. inserting said needle into said support element once said needle has been extracted out of said bone;
  h. loading said suture onto said needle;
  i. retracting said needle out of said bone.

It is another object of the present invention to provide the method as defined above, additionally comprising step of reciprocally moving said stabilizing element along the main longitudinal axis of said circular bone tunneling device so as to be reconfigured from said extended configuration to said retracted configuration and vice versa.

It is another object of the present invention to provide the method as defined above, additionally comprising step of pivotally coupling said stabilizing element, at a pivot point, to the distal end of said hollow elongate body at a pivot point of said circular bone tunneling device.

It is another object of the present invention to provide the method as defined above, wherein said stabilizing element is adapted to radially and pivotably rotate around said pivot point so as to be reconfigured from said extended configuration to said retracted configuration and vice versa.

It is another object of the present invention to provide the method as defined above, wherein said stabilizing element in said extended configuration is adapted to be reversibly anchored within said bone.

It is another object of the present invention to provide the method as defined above, wherein said stabilizing element comprises a distal end and a proximal end; said distal end comprises a flange and a tip; said tip is adapted to penetrate said bone and to reversibly anchor said stabilizing element within the same.

It is another object of the present invention to provide the method as defined above, said flange is adapted to limit the insertion of said distal end of said stabilizing element into said bone such that only said tip is reversibly anchored within said bone.

It is another object of the present invention to provide the method as defined above, wherein the shape of said tip of said stabilizing element is selected from a group consisting of nail-like tip, screw-like tip and any combination thereof.

It is another object of the present invention to provide the method as defined above, additionally comprising step of providing said stabilizing element with at least one marker, adapted to indicate the user as for said stabilizing element position with respect to the bone.

It is another object of the present invention to provide the method as defined above, additionally comprising step of providing said device further with an indicator; said indicator is provided with a yardstick having numerical references on the same; said numerical references are adapted to indicate to the user the depth of penetration of said stabilizing element into said the bone.

It is another object of the present invention to provide the method as defined above, additionally comprising step of providing said device with a locking mechanism adapted to lock said stabilizing element in the desired position.

It is another object of the present invention to provide the method as defined above, additionally comprising step of providing said circular bone tunneling device with at least one suture cartridge comprising a suture; said suture is adapted to be passed through said circular transosseous tunnel previously tunneled through said bone.

It is another object of the present invention to provide the method as defined above, additionally comprising step of linearly moving said suture cartridge in the direction of said support element; thereby loading said suture onto said support element.

It is another object of the present invention to provide the method as defined above, wherein said suture cartridge comprising an external scaffold enclosing an inner body throughout which a surgical tool is inserted.

It is another object of the present invention to provide the method as defined above, wherein said inner body is characterized by having diameter of at least 3 mm.

It is another object of the present invention to provide the method as defined above, additionally comprising step of selecting said surgical tool is a group consisting of grasper, tendon holder, scissors, diathermy, scalpel, stapler, jig, suturing means, and any combination thereof.

It is another object of the present invention to provide the method as defined above, further comprising a step of providing said device with a shaft, parallel to said device's main longitudinal axis; wherein said hollow elongate body head located at the distal end of said shaft and defining said rigid circular arc with the concave side of said arc forming said underside of said hollow elongate body head.

It is another object of the present invention to provide the method as defined above, wherein said shaft additionally comprising an inner elongated hollow tube throughout which a surgical tool is inserted.

It is another object of the present invention to provide the method as defined above, wherein said inner elongated hollow tube is characterized by having diameter of at least 3 mm.

It is another object of the present invention to provide the method as defined above, additionally comprising step of selecting said surgical tool from a group consisting of grasper, tendon holder, scissors, diathermy, scalpel, stapler, jig, suturing means, and any combination thereof.

It is another object of the present invention to provide the method as defined above, wherein said suture cartridge is coupled to said shaft and adapted to reciprocally move along the main longitudinal axis of the same.

It is another object of the present invention to provide the method as defined above, wherein said support element comprises at least one hook adapted to encase said suture.

It is another object of the present invention to provide the method as defined above, wherein said movement of said suture cartridge in the direction of said support element loads said suture onto said hook of said support element.

It is another object of the present invention to provide the method as defined above, wherein said surgical needle is a rigid surgical needle.

It is another object of the present invention to provide the method as defined above, wherein said surgical needle is either straight or curved and shaped as circular arc.

It is another object of the present invention to provide the method as defined above, wherein said needle is adapted to engage with said support element once said needle has tunneled through and exited said bone along said arced path.

It is another object of the present invention to provide the method as defined above, wherein said needle comprises catching means adapted to catch and encase said suture once said needle engages with said support element.

It is another object of the present invention to provide the method as defined above, wherein said catching means are selected from a group consisting of mechanical means, magnetically, electrical means or any combination thereof.

It is another object of the present invention to provide the method as defined above, wherein said mechanical means are at least one hook adapted to encase said suture once said needle engages with said support member.

It is another object of the present invention to provide the method as defined above, wherein said needle comprises at least one hook adapted to encase said suture once said needle engages with said support member.

It is another object of the present invention to provide the method as defined above, wherein said extendable and retractable support element (54) is attached to the distal end of said shaft and structured and configured such that when said support element is extended, it opposes the underside of said curved hollow elongate body head and its distal end is located along the path formed by said rigid circular arc.

It is another object of the present invention to provide the method as defined above, wherein said hollow elongate body head comprising an arc-like shaft along which said support member is guided along tracks so as to be reconfigured to said extended configuration.

It is another object of the present invention to provide the method as defined above, additionally comprising step of providing said device with a support element driving mechanism, adapted, upon activation of a support element control, to drive the motion of said support element.

It is another object of the present invention to provide the method as defined above, wherein upon activation of said support element, the same is extended, such that said bone is being grasped by and between said extendable and retractable support element and said head.

It is another object of the present invention to provide the method as defined above, wherein the distal end of said hollow elongate body head comprises an orifice through which a rigid circular hollow tube passes through.

It is another object of the present invention to provide the method as defined above, wherein the extendable and retractable support element is adapted to reach, upon various degrees of extension, a predetermined location relative to the distal end of said rigid circular hollow tube, such that the distance between said distal end of said rigid circular hollow tube and the upper side of said support element provides a slip fit over a bone through which a suture is to be passed.

It is another object of the present invention to provide the method as defined above, additionally comprising a handle (12).

It is another object of the present invention to provide the method as defined above, wherein said handle is either a reusable handle or a single use handle.

It is another object of the present invention to provide the method as defined above, wherein said arthroscopic surgery is performed without the need of drilling through said bone.

It is another object of the present invention to provide the method as defined above, wherein said hollow elongate body comprises:
  a. at least one track (522) disposed within said hollow elongate body;
  b. a connecting wire (132), forming a loop within said hollow elongate body, the proximal end of said loop physically connected to said rigid circular hollow tube control mechanism;
  c. a distal slidable member (4) disposed within said track and adapted to slide within said track while maintaining said needle and one leg of said loop formed by said connecting wire to pass through said hollow elongate body unhindered, said distal slidable member comprising:
    i. a substantially flat distal edge; and,
    ii. a channel (206) passing through said distal slidable member through which the second leg of said loop formed by said connecting wire passes;
  d. a plurality of additional slidable members (2) disposed within said track and adapted to slide along it while allowing said needle and one leg of said loop formed by said connecting wire to pass through said hollow elongate body unhindered, each of said additional slidable members comprising a channel passing through said distal slidable member through which the second leg of said loop formed by said connecting wire passes; and,
  e. a rigid circular hollow tube actuator (6) disposed within said body proximally to the most proximally located slidable member, said activator disposed so as to engage said rigid circular hollow tube control; wherein said slidable members provides a constant tool profile during said arthroscopic surgery.

It is another object of the present invention to provide the method as defined above, wherein said slidable members (2,4) have the shape of a cylinder with an indentation (204, 404) about its circumference, said channel (206) passing through said cylinder within indentation substantially perpendicular to the longitudinal axis of said cylinder. It is another object of the present invention to provide the method as defined above, wherein said handle comprises a distally located movable segment (12A) and a proximally located stationary segment (12B), said movable segment in physical connection with said support element driving mechanism.

It is another object of the present invention to provide the method as defined above, further incorporating indicating means for indicating the movement, along said acr, of said rigid circular hollow tube.

It is another object of the present invention to provide the method as defined above, wherein said indicating means comprise a window disposed on one side of said shaft; and an indicator located within said shaft, physically connected to said rigid circular hollow tube's driving mechanism such that the distance through which said indicator travels is proportional to the distance the distal end of said rigid circular hollow tube travels, and disposed such that at least part of the travel of said indicator is visible through said window.

It is another object of the present invention to provide a circular bone tunneling device as defined above, wherein said indicating means comprise: a needle indicator in physical communication with the proximal end of actuating means for said rigid circular hollow tube, said needle indicator comprising at least one element visible to the operator of said circular bone tunneling device that undergoes linear motion proportional to the motion of said circular hollow tube; and a support indicator in physical communication with the actuating means for said support element, said support indicator comprising at least one element visible to the operator of said circular bone tunneling device that undergoes linear motion proportional to the motion of said support element.

It is another object of the present invention to provide the method as defined above, further comprising a mark on said side of said shaft in which said window is located, said mark disposed such that when said indicator reaches said mark, the distal end of said rigid circular hollow tube is fully extended.

It is another object of the present invention to provide the method as defined above, additionally comprising step of providing said device with a needle control adapted to control the forward and reverse movement of the needle along said path.

It is another object of the present invention to provide the method as defined above, wherein said needle control comprises a rotatable handle (18) in communication with said needle such that the forward and reverse movement of needle is proportional to the rotation of said rotatable handle.

It is another object of the present invention to provide the method as defined above, wherein said needle control imparts sufficient force to said needle such that the same is provided with sufficient force to penetrate bone.

It is another object of the present invention to provide the method as defined above, wherein said sufficient force is in the range of about 500 to about 600 Newton.

It is another object of the present invention to provide the method as defined above, wherein said hollow elongate body further comprises at least one body slot (330) along at least part of its length, said hollow elongate body head further comprising at least one hollow elongate body head slot (390) along at least part of its length, and said rigid circular hollow tube's driving mechanism comprises:
  a. a rigid circular hollow tube actuator (6) physically connected to said rigid circular hollow tube control, said rigid circular hollow tube actuator disposed within said elongate hollow body and adapted to slide along the proximal-distal axis of said hollow body; and,
  b. a yoke (300) disposed external to said hollow elongate body, said yoke pivotably connected substantially at its proximal end to said rigid circular hollow tube actuator via a connection that passes through said body slot (330) and at pivotably connected substantially at its distal end to said rigid circular hollow tube via a connection that passes through said hollow elongate body head slot (390).

It is another object of the present invention to provide the method as defined above, wherein said support element driving mechanism comprises an actuator (58) adapted to reconfigure said support element to said retracted configuration to said extended configuration and vice versa.

It is another object of the present invention to provide the method as defined above, wherein said support element driving mechanism comprises a yoke (340) pivotably connected at its proximal end to said actuator (58) and pivotably connected to said support element.

It is another object of the present invention to provide the method as defined above, wherein at least one selected from a group consisting of said support element, said needle and any combination thereof is actuated mechanically by a motor.

It is another object of the present invention to provide the method as defined above, wherein said needle is characterized by having cross sectional area selected from a group consisting of circular, triangular, rectangular, flat, or any combination thereof.

It is another object of the present invention to provide the method as defined above, additionally comprising step of providing said device with a retractable sleeve characterized by having at least two positions (a) an extended position, in which said sleeve completely encircles said needle; and, (b) retracted position, in which said needle partially protrudes out of said retractable sleeve.

It is another object of the present invention to provide the method as defined above, additionally comprising step of providing said device with at least one anchor, in mechanical communication with said suture.

It is another object of the present invention to provide the method as defined above, wherein said needle is adapted to engage with said anchor so as to encase said suture.

It is another object of the present invention to provide the method as defined above, wherein said engagement of said suture with said anchor forms at least one loop.

It is another object of the present invention to provide the method as defined above, wherein n additional sutures are interleaved and threaded through said loop; n is an integer greater than 1.

The circular bone tunneling device as defined above, wherein said needle is characterized by having cross sectional area selected from a group consisting of circular, triangular, rectangular, flat or any combination thereof.

It is another object of the present invention to provide the circular bone tunneling device as defined above, wherein said handle is attached to the body of said device so as to permit translation of said handle in the proximal-distal direction relative to the body, rotation of said handle about its longitudinal axis, and fixing of the position of said handle.

It is another object of the present invention to provide the circular bone tunneling device as defined above, wherein said indicating means comprise:
a. a needle indicator in physical communication with the proximal end of actuating means for said rigid circular hollow tube, said needle indicator comprising at least one element visible to the operator of said circular bone tunneling device that undergoes linear motion proportional to the motion of said circular hollow tube; and,
b. a support indicator in physical communication with the actuating means for said support element, said support indicator comprising at least one element visible to the operator of said circular bone tunneling device that undergoes linear motion proportional to the motion of said support element.

It is another object of the present invention to provide the circular bone tunneling device as defined above, wherein said yoke comprises a single prong disposed on one side of said shaft.

It is another object of the present invention to provide the circular bone tunneling device as defined above, further comprising a surgical tool disposed within said shaft.

It is another object of the present invention to provide the circular bone tunneling device as defined above, wherein said surgical tool is selected from a group consisting of grasper, tendon holder, scissors, diathermy, scalpel, stapler, jig, suturing means, and any combination thereof.

It is another object of the present invention to provide the circular bone tunneling device as defined above, further comprising an extendable jig disposed within said shaft.

It is another object of the present invention to provide the method as defined above, wherein said needle is characterized by having cross sectional area selected from a group consisting of circular, triangular, rectangular, flat or any combination thereof.

It is another object of the present invention to provide the method as defined above, wherein said handle is attached to the body of said device so as to permit translation of said handle in the proximal-distal direction relative to the body, rotation of said handle about its longitudinal axis, and fixing of the position of said handle.

It is another object of the present invention to provide the method as defined above, wherein said indicating means comprise:
c. a needle indicator in physical communication with the proximal end of actuating means for said rigid circular hollow tube, said needle indicator comprising at least one element visible to the operator of said circular bone tunneling device that undergoes linear motion proportional to the motion of said circular hollow tube; and,
d. a support indicator in physical communication with the actuating means for said support element, said support indicator comprising at least one element visible to the operator of said circular bone tunneling device that undergoes linear motion proportional to the motion of said support element.

It is another object of the present invention to provide the method as defined above, wherein said yoke comprises a single prong disposed on one side of said shaft.

It is another object of the present invention to provide the method as defined above, further comprising a surgical tool disposed within said shaft.

It is another object of the present invention to provide the method as defined above, wherein said surgical tool is selected from a group consisting of grasper, tendon holder, scissors, diathermy, scalpel, stapler, jig, suturing means, and any combination thereof.

It is another object of the present invention to provide the method as defined above, further comprising an extendable jig disposed within said shaft.

It is therefore another object to provide a circular bone tunneling device for use in arthroscopic surgery, comprising: a hollow elongate body comprising a hollow elongate body head, said a hollow elongate body head defining a rigid circular arc; said hollow elongate body head comprising a surgical needle adapted to tunnel through a bone along a path formed by said rigid circular arc; and, an extendable and retractable support element, reconfigurable from at least one extended configuration to at least one retracted configuration; said support element, in said extended configuration, is adapted to be located along said path formed by said rigid circular arc; said support element, in said extended configuration, and said hollow elongate body head are adapted to grasp said bone from at least two points along the circumference of said bone; a suture cartridge comprising a suture to be passed through said circular arc tunneled through said bone.

It is another object of the present invention to provide the circular bone tunneling device as defined above, wherein said suture cartridge comprising an external scaffold enclosing an inner body throughout which a surgical tool is inserted.

It is another object of the present invention to provide the circular bone tunneling device as defined above, wherein said inner body is characterized by having diameter of at least 3 mm.

It is another object of the present invention to provide the circular bone tunneling device as defined above, wherein said surgical tool is selected from a group consisting of grasper, tendon holder, scissors, diathermy, scalpel, stapler, jig, suturing means, and any combination thereof.

It is another object of the present invention to provide the circular bone tunneling device as defined above, further comprising a shaft; wherein said hollow elongate body head located at the distal end of said shaft and defining said rigid circular arc with the concave side of said arc forming said underside of said hollow elongate body head.

It is another object of the present invention to provide the circular bone tunneling device as defined above, wherein said shaft additionally comprising an inner elongated hollow tube throughout which a surgical tool is inserted.

It is another object of the present invention to provide the circular bone tunneling device as defined above, wherein said inner elongated hollow tube is characterized by having diameter of at least 3 mm.

It is another object of the present invention to provide the circular bone tunneling device as defined above, wherein said surgical tool is selected from a group consisting of grasper, tendon holder, scissors, diathermy, scalpel, stapler, jig, suturing means, and any combination thereof.

It is another object of the present invention to provide the circular bone tunneling device as defined above, wherein said suture cartridge is coupled to said shaft and adapted to reciprocally move along the main longitudinal axis of the same.

It is another object of the present invention to provide the circular bone tunneling device as defined above, wherein said support element comprises at least one hook adapted to encase said suture.

It is another object of the present invention to provide the circular bone tunneling device as defined above, wherein said movement of said suture cartridge in the direction of said support element loads said suture onto said hook of said support member.

It is another object of the present invention to provide the circular bone tunneling device as defined above, wherein said surgical needle is a rigid surgical needle.

It is another object of the present invention to provide the circular bone tunneling device as defined above, wherein said surgical needle is either straight or curved and shaped as circular arc.

It is another object of the present invention to provide the circular bone tunneling device as defined above, wherein said needle is adapted to engage with said support member once said needle has tunneled through said bone along said arc-like path.

It is another object of the present invention to provide the circular bone tunneling device as defined above, wherein said needle comprises means adapted to catch and encase said suture once said needle engages with said support member.

It is another object of the present invention to provide the circular bone tunneling device as defined above, wherein said means are selected from a group consisting of mechanical means, magnetically, electrical means or any combination thereof.

It is another object of the present invention to provide the circular bone tunneling device as defined above, wherein said mechanical means are at least one hook adapted to encase said suture once said needle engages with said support member.

It is another object of the present invention to provide the circular bone tunneling device as defined above, wherein said needle comprises at least one hook adapted to encase said suture once said needle engages with said support member.

It is another object of the present invention to provide the circular bone tunneling device as defined above, wherein said extendable and retractable support element (54) is attached to the distal end of said shaft and disposed such that when said support element is extended, it opposes the underside of said curved hollow elongate body head and its distal end is located along the path formed by said rigid circular arc.

It is another object of the present invention to provide the circular bone tunneling device as defined above, wherein said hollow elongate body head comprising an arc-like shaft along which said support member slides so as to be reconfigured to said extended configuration.

It is another object of the present invention to provide the circular bone tunneling device as defined above, additionally comprising a support element driving mechanism, adapted, upon activation of a support element control, to drive the motion of said support element.

It is another object of the present invention to provide the circular bone tunneling device as defined above, wherein upon activation of said support element, the same is extended, such that said bone is being grasped by said extendable and retractable support element and said head.

It is another object of the present invention to provide the circular bone tunneling device as defined above, wherein the extendable and retractable support element is adapted to reach, upon extension, a predetermined location relative to the distal end of said rigid circular hollow tube, such that the distance between said distal end of said rigid circular hollow tube and the upper side of said support element provides a slip fit over a bone through which a suture is to be passed.

It is another object of the present invention to provide the circular bone tunneling device as defined above, additionally comprising a handle (12).

It is another object of the present invention to provide the circular bone tunneling device as defined above, wherein said handle is either a reusable handle or a single use handle.

It is another object of the present invention to provide the circular bone tunneling device as defined above, wherein said arthroscopic surgery is performed without the need of drilling through said bone.

It is another object of the present invention to provide the circular bone tunneling device as defined above, wherein said hollow elongate body comprises: at least one track (522) disposed within said hollow elongate body; a connecting wire (132), forming a loop within said hollow elongate body, the proximal end of said loop physically connected to said rigid circular hollow tube control mechanism; a distal slidable member (4) disposed within said track and adapted to slide along it while allowing said needle and one leg of said loop formed by said connecting wire to pass through said hollow elongate body unhindered, said distal slidable member comprising a substantially flat distal edge; and a channel (206) passing through said distal slidable member through which the second leg of said loop formed by said connecting wire passes; a plurality of additional slidable members (2) disposed within said track and adapted to slide along it while allowing said needle and one leg of said loop formed by said connecting wire to pass through said hollow elongate body unhindered, each of said additional slidable members comprising a channel passing through said distal slidable member through which the second leg of said loop formed by said connecting wire passes; and a rigid circular hollow tube actuator (6) disposed within said body proximally to the most proximally located slidable member, said activator disposed so as to engage said rigid circular hollow tube control; wherein said slidable members provide a constant tool profile during said arthroscopic surgery.

It is another object of the present invention to provide the circular bone tunneling device as defined above, wherein said slidable members (2,4) have the shape of a cylinder with an indentation (204) about its circumference, said channel (206) passing through said cylinder within indentation substantially perpendicular to the longitudinal axis of said cylinder.

It is another object of the present invention to provide the circular bone tunneling device as defined above, wherein said handle comprises a distally located movable segment (12A) and a proximally located stationary segment (12B), said movable segment in physical connection with said support element driving mechanism.

It is another object of the present invention to provide the circular bone tunneling device as defined above, further incorporating indicating means for indicating the extent of travel, along said arc, of said rigid circular hollow tube.

It is another object of the present invention to provide the circular bone tunneling device as defined above, wherein said indicating means comprise
 a window disposed on one side of said shaft; and,
 an indicator located within said shaft, physically connected to said rigid circular hollow tube driving mechanism such that the distance through which said indicator travels is proportional to the distance the distal end of said rigid circular hollow tube travels, and disposed such that at least part of the travel of said indicator is visible through said window;

It is another object of the present invention to provide the circular bone tunneling device as defined above, further comprising a mark on said side of said shaft in which said window is disposed, said mark disposed such that when said indicator reaches said mark, the distal end of said rigid circular hollow tube is fully extended.

It is another object of the present invention to provide the circular bone tunneling device as defined above, additionally comprising a needle control adapted to control the amount of movement the needle has traveled.

It is another object of the present invention to provide the circular bone tunneling device as defined above, wherein said needle control comprises a rotatable handle (18) in communication with said needle such that the distance through which said needle travels is proportional to the rotational angle through which said rotatable handle is rotated.

It is another object of the present invention to provide the circular bone tunneling device as defined above, wherein said needle control imparts sufficient force to said needle such that the same is provided with sufficient force to penetrate bone.

It is another object of the present invention to provide the circular bone tunneling device as defined above, wherein said sufficient force is in the range of about 500 to about 600 Newton.

It is another object of the present invention to provide the circular bone tunneling device as defined above, wherein said hollow elongate body further comprises at least one body slot (330) along at least part of its length, said hollow elongate body head further comprising at least one hollow elongate body head slot (390) along at least part of its length, and said rigid circular hollow tube driving mechanism comprises:

a rigid circular hollow tube actuator (310) physically connected to said rigid circular hollow tube control, said rigid circular hollow tube actuator disposed within said elongate hollow body and adapted to slide along the proximal-distal axis of said hollow body; and,
 a yoke (300) disposed external to said hollow elongate body, said yoke pivotably connected substantially at its proximal end to said rigid circular hollow tube actuator via a connection that passes through said body slot (330) and at pivotably connected substantially at its distal end to said rigid circular hollow tube via a connection that passes through said hollow elongate body head slot (390).

It is another object of the present invention to provide the circular bone tunneling device as defined above, wherein said support element driving mechanism comprises an actuator (58) adapted to reconfigure said support element to said retracted configuration to said extended configuration and vice versa.

It is another object of the present invention to provide the circular bone tunneling device as defined above, wherein said support element driving mechanism comprises a yoke (340) pivotably connected at its proximal end to said actuator (58) and pivotably connected to said support element.

It is another object of the present invention to provide the circular bone tunneling device as defined above, wherein at least one selected from a group consisting of said support element, said needle and any combination thereof is actuated mechanically by a motor.

It is another object of the present invention to provide the circular bone tunneling device as defined above, wherein said needle is characterized by having cross sectional area selected from a group consisting of circular, triangular, rectangular, flat or any combination thereof.

It is another object of the present invention to provide the circular bone tunneling device as defined above, additionally comprising a retractable sleeve characterized by having at least two positions (a) an extended position, in which said sleeve completely encircles said needle; and, (b) retracted position, in which said needle partially protrudes out of said retractable sleeve.

It is another object of the present invention to provide the circular bone tunneling device as defined above, additionally comprising at least one anchor, in mechanical communication with said suture.

It is another object of the present invention to provide the circular bone tunneling device as defined above, wherein said needle is adapted to engage with said anchor so as to encase said suture.

It is another object of the present invention to provide the circular bone tunneling device as defined above, wherein said anchor comprises means adapted to enable interleave of n additional sutures threaded through the same; n is an integer greater than 1.

It is another object of the present invention to provide a method for tunneling through a bone during arthroscopic surgery, said method comprising steps of:
 a. providing a curved bone tunneling device comprising:
  a hollow elongate body comprising a hollow elongate body head, said a hollow elongate body head defining a rigid circular arc; said hollow elongate body head comprising a surgical needle adapted to tunnel through a bone along a path formed by said rigid circular arc;
  i. an extendable and retractable support element, reconfigurable from at least one extended configuration to at least one retracted configuration; and,
  ii. a suture cartridge comprising a suture;

b. positioning said hollow elongate body of said device adjacent to the circumference of a bone;
c. fixating said needle to said bone;
d. extending said retractable support element to a location along the path formed by said circular arc; thereby grasping said bone with said support element and said hollow elongate body at two points along the circumference of said bone;
e. linearly moving said suture cartridge in the direction of said support element; thereby loading said suture onto said support element;
f. actuating said needle, thereby tunneling through said bone along said circular arc path;
g. inserting said needle into said support element once said needle has been extracted out of said bone;
h. loading said suture onto said needle;
i. retracting said needle out of said bone;
j. wherein said step of tunneling through said bone is performed without drilling.

It is another object of the present invention to provide the method as defined above, wherein said suture cartridge comprising an external scaffold enclosing an inner body throughout which a surgical tool is inserted.

It is another object of the present invention to provide the method as defined above, wherein said inner body is characterized by having diameter of at least 3 mm.

It is another object of the present invention to provide the method as defined above, additionally comprising step of selecting said surgical tool is a group consisting of grasper, tendon holder, scissors, diathermy, scalpel, stapler, jig, suturing means, and any combination thereof.

It is another object of the present invention to provide the method as defined above, further comprising a step of providing said device with a shaft; wherein said hollow elongate body head located at the distal end of said shaft and defining said rigid circular arc with the concave side of said arc forming said underside of said hollow elongate body head.

It is another object of the present invention to provide the method as defined above, wherein said shaft additionally comprising an inner elongated hollow tube throughout which a surgical tool is inserted.

It is another object of the present invention to provide the method as defined above, wherein said inner elongated hollow tube is characterized by having diameter of at least 3 mm.

It is another object of the present invention to provide the method as defined above, additionally comprising step of selecting said surgical tool from a group consisting of grasper, tendon holder, scissors, diathermy, scalpel, stapler, jig, suturing means, and any combination thereof.

It is another object of the present invention to provide the method as defined above, wherein said suture cartridge is coupled to said shaft and adapted to reciprocally move along the main longitudinal axis of the same.

It is another object of the present invention to provide the method as defined above, wherein said support element comprises at least one hook adapted to encase said suture.

It is another object of the present invention to provide the method as defined above, wherein said movement of said suture cartridge in the direction of said support element loads said suture onto said hook of said support member.

It is another object of the present invention to provide the method as defined above, wherein said surgical needle is a rigid surgical needle.

It is another object of the present invention to provide the method as defined above, wherein said surgical needle is either straight or curved and shaped as circular arc.

It is another object of the present invention to provide the method as defined above, wherein said needle is adapted to engage with said support member once said needle has tunneled through said bone along said arc-like path.

It is another object of the present invention to provide the method as defined above, wherein said needle comprises means adapted to catch and encase said suture once said needle engages with said support member.

It is another object of the present invention to provide the method as defined above, wherein said means are selected from a group consisting of mechanical means, magnetically, electrical means or any combination thereof.

It is another object of the present invention to provide the method as defined above, wherein said mechanical means are at least one hook adapted to encase said suture once said needle engages with said support member.

It is another object of the present invention to provide the method as defined above, wherein said needle comprises at least one hook adapted to encase said suture once said needle engages with said support member.

It is another object of the present invention to provide the method as defined above, wherein said extendable and retractable support element (54) is attached to the distal end of said shaft and disposed such that when said support element is extended, it opposes the underside of said curved hollow elongate body head and its distal end is located along the path formed by said rigid circular arc.

It is another object of the present invention to provide the method as defined above, wherein said hollow elongate body head comprising an arc-like shaft along which said support member slides so as to be reconfigured to said extended configuration.

It is another object of the present invention to provide the method as defined above, additionally comprising step of providing said device with a support element driving mechanism, adapted, upon activation of a support element control, to drive the motion of said support element.

It is another object of the present invention to provide the method as defined above, wherein upon activation of said support element, the same is extended, such that said bone is being grasped by said extendable and retractable support element and said head.

It is another object of the present invention to provide the method as defined above, wherein the extendable and retractable support element is adapted to reach, upon extension, a predetermined location relative to the distal end of said rigid circular hollow tube, such that the distance between said distal end of said rigid circular hollow tube and the upper side of said support element provides a slip fit over a bone through which a suture is to be passed.

It is another object of the present invention to provide the method as defined above, additionally comprising a handle (12).

It is another object of the present invention to provide the method as defined above, wherein said handle is either a reusable handle or a single use handle.

It is another object of the present invention to provide the method as defined above, wherein said arthroscopic surgery is performed without the need of drilling through said bone.

It is another object of the present invention to provide the method as defined above, wherein said hollow elongate body comprises:
a. at least one track (522) disposed within said hollow elongate body;

b. a connecting wire (132), forming a loop within said hollow elongate body, the proximal end of said loop physically connected to said rigid circular hollow tube control mechanism;
c. a distal slidable member (4) disposed within said track and adapted to slide along it while allowing said needle and one leg of said loop formed by said connecting wire to pass through said hollow elongate body unhindered, said distal slidable member comprising:
   i. a substantially flat distal edge; and,
   ii. a channel (206) passing through said distal slidable member through which the second leg of said loop formed by said connecting wire passes;
d. a plurality of additional slidable members (2) disposed within said track and adapted to slide along it while allowing said needle and one leg of said loop formed by said connecting wire to pass through said hollow elongate body unhindered, each of said additional slidable members comprising a channel passing through said distal slidable member through which the second leg of said loop formed by said connecting wire passes; and,
e. a rigid circular hollow tube actuator (6) disposed within said body proximally to the most proximally located slidable member, said activator disposed so as to engage said rigid circular hollow tube control; wherein said slidable members provides a constant tool profile during said arthroscopic surgery.

It is another object of the present invention to provide the method as defined above, wherein said slidable members (2,4) have the shape of a cylinder with an indentation (204) about its circumference, said channel (206) passing through said cylinder within indentation substantially perpendicular to the longitudinal axis of said cylinder. It is another object of the present invention to provide the method as defined above, wherein said handle comprises a distally located movable segment (12A) and a proximally located stationary segment (12B), said movable segment in physical connection with said support element driving mechanism.

It is another object of the present invention to provide the method as defined above, further incorporating indicating means for indicating the extent of travel, along said acr, of said rigid circular hollow tube.

It is another object of the present invention to provide the method as defined above, wherein said indicating means comprise a window disposed on one side of said shaft; and an indicator located within said shaft, physically connected to said rigid circular hollow tube driving mechanism such that the distance through which said indicator travels is proportional to the distance the distal end of said rigid circular hollow tube travels, and disposed such that at least part of the travel of said indicator is visible through said window.

It is another object of the present invention to provide a circular bone tunneling device as defined above, wherein said indicating means comprise: a needle indicator in physical communication with the proximal end of actuating means for said rigid circular hollow tube, said needle indicator comprising at least one element visible to the operator of said circular bone tunneling device that undergoes linear motion proportional to the motion of said circular hollow tube; and a support indicator in physical communication with the actuating means for said support element, said support indicator comprising at least one element visible to the operator of said circular bone tunneling device that undergoes linear motion proportional to the motion of said support element.

It is another object of the present invention to provide the method as defined above, further comprising a mark on said side of said shaft in which said window is disposed, said mark disposed such that when said indicator reaches said mark, the distal end of said rigid circular hollow tube is fully extended.

It is another object of the present invention to provide the method as defined above, additionally comprising step of providing said device with a needle control adapted to control the amount of movement the needle has traveled.

It is another object of the present invention to provide the method as defined above, wherein said needle control comprises a rotatable handle (18) in communication with said needle such that the distance through which said needle travels is proportional to the rotational angle through which said rotatable handle is rotated.

It is another object of the present invention to provide the method as defined above, wherein said needle control imparts sufficient force to said needle such that the same is provided with sufficient force to penetrate bone.

It is another object of the present invention to provide the method as defined above, wherein said sufficient force is in the range of about 500 to about 600 Newton.

It is another object of the present invention to provide the method as defined above, wherein said hollow elongate body further comprises at least one body slot (330) along at least part of its length, said hollow elongate body head further comprising at least one hollow elongate body head slot (390) along at least part of its length, and said rigid circular hollow tube driving mechanism comprises:
a. a rigid circular hollow tube actuator (310) physically connected to said rigid circular hollow tube control, said rigid circular hollow tube actuator disposed within said elongate hollow body and adapted to slide along the proximal-distal axis of said hollow body; and,
b. a yoke (300) disposed external to said hollow elongate body, said yoke pivotably connected substantially at its proximal end to said rigid circular hollow tube actuator via a connection that passes through said body slot (330) and at pivotably connected substantially at its distal end to said rigid circular hollow tube via a connection that passes through said hollow elongate body head slot (390).

It is another object of the present invention to provide the method as defined above, wherein said support element driving mechanism comprises an actuator (58) adapted to reconfigure said support element to said retracted configuration to said extended configuration and vice versa.

It is another object of the present invention to provide the method as defined above, wherein said support element driving mechanism comprises a yoke (340) pivotably connected at its proximal end to said actuator (58) and pivotably connected to said support element.

It is another object of the present invention to provide the method as defined above, wherein at least one selected from a group consisting of said support element, said needle and any combination thereof is actuated mechanically by a motor.

It is another object of the present invention to provide the method as defined above, wherein said needle is characterized by having cross sectional area selected from a group consisting of circular, triangular, rectangular, flat, or any combination thereof.

It is another object of the present invention to provide the method as defined above, additionally comprising step of providing said device with a retractable sleeve characterized by having at least two positions (a) an extended position, in which said sleeve completely encircles said needle; and, (b) retracted position, in which said needle partially protrudes out of said retractable sleeve.

It is another object of the present invention to provide the method as defined above, additionally comprising step of providing said device with at least one anchor, in mechanical communication with said suture.

It is another object of the present invention to provide the method as defined above, wherein said needle is adapted to engage with said anchor so as to encase said suture.

It is another object of the present invention to provide the method as defined above, wherein said anchor comprises means adapted to enable interleave of n additional sutures threaded through the same; n is an integer greater than 1.

The circular bone tunneling device according to claim 1, wherein said needle is characterized by having cross sectional area selected from a group consisting of circular, triangular, rectangular, flat or any combination thereof.

It is another object of the present invention to provide the circular bone tunneling device as defined above, wherein said handle is attached to the body of said device so as to permit translation of said handle in the proximal-distal direction relative to the body, rotation of said handle about its longitudinal axis, and fixing of the position of said handle.

It is another object of the present invention to provide the circular bone tunneling device as defined above, wherein said indicating means comprise:
 a. a needle indicator in physical communication with the proximal end of actuating means for said rigid circular hollow tube, said needle indicator comprising at least one element visible to the operator of said circular bone tunneling device that undergoes linear motion proportional to the motion of said circular hollow tube; and,
 b. a support indicator in physical communication with the actuating means for said support element, said support indicator comprising at least one element visible to the operator of said circular bone tunneling device that undergoes linear motion proportional to the motion of said support element.

It is another object of the present invention to provide the circular bone tunneling device as defined above, wherein said yoke comprises a single prong disposed on one side of said shaft.

It is another object of the present invention to provide the circular bone tunneling device as defined above, further comprising a surgical tool disposed within said shaft.

It is another object of the present invention to provide the circular bone tunneling device as defined above, wherein said surgical tool is selected from a group consisting of grasper, tendon holder, scissors, diathermy, scalpel, stapler, jig, suturing means, and any combination thereof.

It is another object of the present invention to provide the circular bone tunneling device as defined above, further comprising an extendable jig disposed within said shaft.

It is another object of the present invention to provide the method as defined above, wherein said needle is characterized by having cross sectional area selected from a group consisting of circular, triangular, rectangular, flat or any combination thereof.

It is another object of the present invention to provide the method as defined above, wherein said handle is attached to the body of said device so as to permit translation of said handle in the proximal-distal direction relative to the body, rotation of said handle about its longitudinal axis, and fixing of the position of said handle.

It is another object of the present invention to provide the method as defined above, wherein said indicating means comprise:
 a. a needle indicator in physical communication with the proximal end of actuating means for said rigid circular hollow tube, said needle indicator comprising at least one element visible to the operator of said circular bone tunneling device that undergoes linear motion proportional to the motion of said circular hollow tube; and,
 b. a support indicator in physical communication with the actuating means for said support element, said support indicator comprising at least one element visible to the operator of said circular bone tunneling device that undergoes linear motion proportional to the motion of said support element.

It is another object of the present invention to provide the method as defined above, wherein said yoke comprises a single prong disposed on one side of said shaft.

It is another object of the present invention to provide the method as defined above, further comprising a surgical tool disposed within said shaft.

It is another object of the present invention to provide the method as defined above, wherein said surgical tool is selected from a group consisting of grasper, tendon holder, scissors, diathermy, scalpel, stapler, jig, suturing means, and any combination thereof.

It is another object of the present invention to provide the method as defined above, further comprising an extendable jig disposed within said shaft.

BRIEF DESCRIPTION OF THE DRAWINGS

The invention disclosed herein is now described with reference to the drawings, wherein:

FIGS. 9a-9c presents isometric views of the support element control according to a preferred embodiment of the invention;

FIGS. 12a-12c presents a schematic view of a motorized control system for the curved/circular bone tunneling device or adjustable suture passer disclosed herein;

DETAILED DESCRIPTION OF THE PREFERRED EMBODIMENTS

Figure 1A:
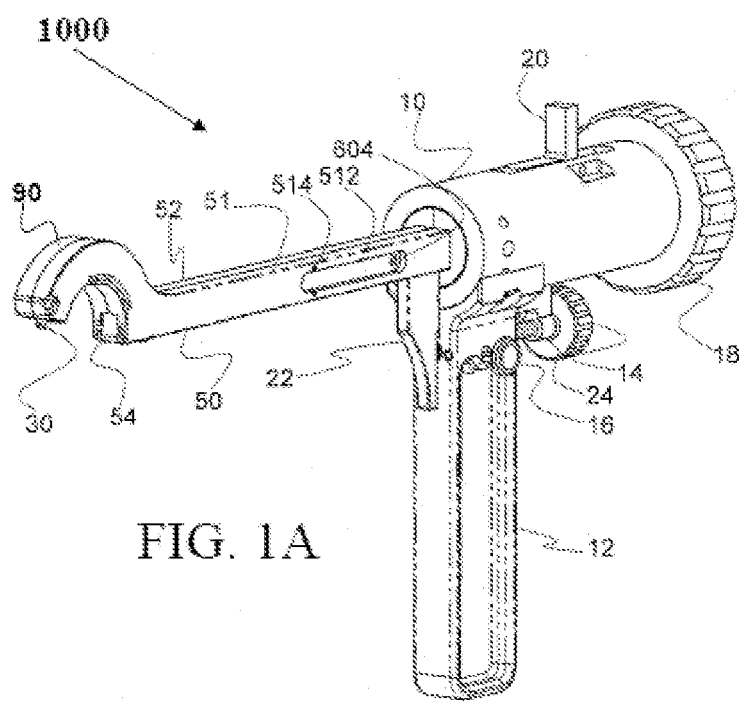
FIGS. 1a-1c presents isometric drawings of the curved/circular bone tunneling device or adjustable suture passer herein disclosed according to one embodiment of the invention.

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figures and described in the specification, but only as indicated in the accompanying claims, with the proper scope determined only by the broadest interpretation of said claims.

The present invention provides a bone tunneling device that "grabs" and firmly holds the bone at two different points along an arc and is stabilized by a stabilizing element that reduces the movement (degrees of freedom) by fixating the device to the bone at a third contact point such that movement is minimized and the forces applied to the needle will be facilitated to be able to drive into the bone and further inadvertent movement by the physician due to hand movements will not affect the position of the device.

The present invention provides a circular bone tunneling device, for use in arthroscopic surgery, comprising:
  a hollow elongate body comprising a hollow elongate body head, said a hollow elongate body head defining a rigid circular arc; said hollow elongate body head comprising a surgical needle adapted move along said hollow elongate body head and through an orifice in said hollow elongate body head to tunnel through a bone along a path formed by said rigid circular arc; and,
  an extendable and retractable support element, reconfigurable from at least one extended configuration to at least one retracted configuration;
  said support element, in said extended configuration is adapted to be located along said path formed by said rigid circular arc; said support element, in said extended configuration, and said hollow elongate body head are adapted to grasp said bone from at least two points along the circumference of said bone;
  a stabilizing element reconfigurable from at least one extended configuration to at least one retracted configuration; wherein said stabilizing element in said extended configuration, is adapted to be in physical contact with said bone so as to fixate the orientation of said circular bone tunneling device relative to said bone.

It is within the core essence of the present invention where said stabilizing element is adapted to reciprocally move along the main longitudinal axis of said circular bone tunneling device so as to be reconfigured from said extended configuration to said retracted configuration and vice versa.

It is within the core essence of the present invention where said stabilizing element is pivotally coupled, at a pivot point, to the distal end of said hollow elongate body at a pivot point of said circular bone tunneling device.

It is within the core essence of the present invention where said stabilizing element is adapted to radially and pivotably rotate around said pivot point so as to be reconfigured from said extended configuration to said retracted configuration and vice versa.

It is within the core essence of the present invention where said stabilizing element in said extended configuration is adapted to be anchored within said bone.

It is within the core essence of the present invention where said stabilizing element comprises a distal end and a proximal end; said distal end comprises a flange and a tip; said tip is adapted to penetrate said bone and to anchor said stabilizing element within the same.

It is within the core essence of the present invention where said flange is adapted to prevent the insertion of said proximal end of said stabilizing element into said bone such that only said tip is anchored within said bone.

It is within the core essence of the present invention where the shape of said tip of said stabilizing element is selected from a group consisting of nail-like tip, screw-like tip and any combination thereof.

It is within the core essence of the present invention where said device additionally comprising at least one suture cartridge comprising a suture; said suture is adapted to be passed through said circular arc tunneled through said bone.

It is within the core essence of the present invention where said support element, in said extended configuration is adapted to be located along said path formed by said circular arc.

It is within the core essence of the present invention where said support element, in said extended configuration, and said hollow elongate body are adapted to grasp said bone from at least two points along the circumference of said bone.

It is another object of the present invention to provide the circular bone tunneling device as defined above, wherein said suture cartridge comprising an external scaffold enclosing an inner body throughout which a surgical tool is inserted.

It is another object of the present invention to provide the circular bone tunneling device as defined above, wherein said surgical tool is selected from a group consisting of grasper, tendon holder and any combination thereof.

According to another embodiment of the present invention the surgical needle as defined above, is a rigid surgical needle.

According to another embodiment of the present invention the surgical needle's shape is slightly curved and approximately defines a circular arc.

The present invention also provides a method for tunneling through a bone during arthroscopic surgery. The method comprises steps of:
(a) providing a curved bone tunneling device comprising:
a hollow elongate body comprising a hollow elongate body head, said a hollow elongate body head defining a rigid circular arc; said hollow elongate body head comprising a surgical needle adapted move along said hollow elongate body head and through an orifice in said hollow elongate body head to tunnel through a bone along a path formed by said rigid circular arc;
an extendable and retractable support element, reconfigurable from at least one extended configuration to at least one retracted configuration; and,
a stabilizing element reconfigurable from at least one extended configuration to at least one retracted configuration; wherein said stabilizing element in said extended configuration, is adapted to be in physical contact with said bone so as to fixate the orientation of said circular bone tunneling device relative to said bone;
(b) positioning said hollow elongate body of said device adjacent to the circumference of a bone;
(c) fixating said needle to said bone;
(d) extending said retractable support element to a location along the path formed by said circular arc; thereby grasping said bone with said support element and said hollow elongate body at two points along the circumference of said bone;
(e) extending said stabilizing element so as to reconfigure the same from said retracted configuration to said extended configuration; thereby fixating the orientation of said curved bone tunneling device relative to said bone;
(f) actuating said needle, thereby tunneling through said bone along said circular arc path;
(g) inserting said needle into said support element once said needle has been extracted out of said bone;
(h) loading said suture onto said needle; and,
(i) retracting said needle out of said bone; wherein said step of tunneling through said bone is performed without drilling.

As described above, the present invention provides an arthroscopic bone tunneling device which tunnels through an arc defined by two points on the circumference of a bone. The tunnel is formed by penetration of a needle device attached to a rigid hollow tube without the need to drill.

According to one embodiment, the arthroscopic bone tunneling device is connected to a suture which is simultaneously passed through the tunnel so formed. The suture can then be used to fix a, tissue, muscle or ligament to a bone tissue.

The arthroscopic bone tunneling device comprises, inter alia, a rigid hollow tube and which penetrates the bone at a first point along the circumference of the same; and an extendable and retractable support element (will be disclosed hereinafter) which provides counter force at a second point along the circumference of the bone close to where the arc (i.e., the needle) exits the bone. Such an extendable and retractable support element enables the tunneling without drilling.

No anchors are required since the sutures are fixed to through the arc formed in the bone in a full loop configuration.

The extendable and retractable support (which provides the contra) device fixates the bone tunneling device onto the bone while tunneling is being performed.

The entire unit has a low profile when entering the incision and a slightly larger profile when the fixation device is deployed.

Thus the unit is the first truly minimally invasive tool for rotary cuff repair and does not require a large access incision and/or large sub-dermal space to deploy its streamline no drilling configuration.

The circular tunneler/adjustable suture passer of the present invention is characterized by the following advantages:
(a) unlike most of the prior art devices, the circular tunneler/adjustable suture passer of the present invention performs no drilling through the bone; alternatively the present invention tunnels through the bone by applying consistent and sufficient force to a needle enabled by the force applied on the bone by the retractable support element as counter force to the force applied to the bone by the needle.
(b) the penetration through the bone is performed according to an arc shaped path (e.g. single bone entrance). Several known prior art publications refer to the drilling of two orthogonal bores/channels so as to perform the arthroscopic surgery. As mentioned above, such orthogonal bores are likely to cause fractures to the bone by weakening the same.
(c) the suture passer is adjustable. Due to the novel configuration of the device (namely, the extendable and retractable support element, as will be disclosed hereinafter), the same can accommodate different bone diameters and different shapes and structures. In other words, the device of the present invention is adapted to various sizes, shapes and bone dimensions. The term "about" refers hereinafter to a range of 25% below or above the referred value.

As used herein, the term "needle" is understood to indicate any sharp instrument used in medical practice to penetrate tissue. Thus, as non-limiting examples, the term is understood to include such instruments as surgical needles and lances. It is also understood to include both hollow and solid instruments.

As used herein, the term "slip fit" refers to the mating of two mechanical components.

As used herein the term "ejecting" refers to an act of penetration or tunneling of an element through the bone without any drilling or removing bone material (e.g. debris).

As used herein the term "adjustable" refers to the ability of the circular bone tunneling device/suture passer to accommodate different bone diameters and different shapes and structures.

As used herein the term "support" refers to maintaining the hollow elongate body head unit flush with bone surface by means of fixation of the unit to the bone circumference.

As used herein the term "fixation" refers to non-displacement of the hollow elongate body head and/or the surgical needle and/or the hollow tube when forces are being applied by the hollow tube driving mechanism and insures that the position of the hollow elongate body head and/or the surgical needle and/or the hollow tube are maintained in the same selected position.

Figure 1B:
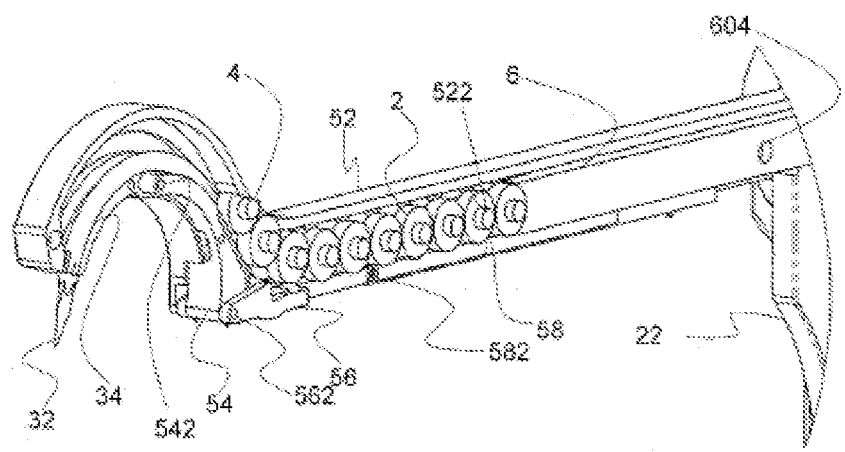
Figure 1C:
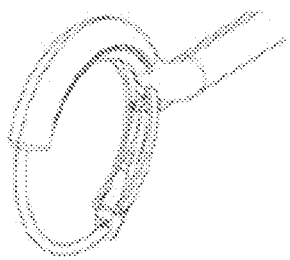

Reference is now made to FIG. 1, which presents isometric drawings of a preferred embodiment 1000 of the invention herein disclosed. FIG. 1A presents an external view of the circular bone tunneling device/adjustable suture passer. A hollow elongate body forms the distal portion of the tool. The distal portion of the body comprises a hollow elongate body head 90 (referred hereinafter as head or hollow elongate body head), which is curved downwards; as shown in the illustration, in preferred embodiments, the head describes a rigid and an essentially semicircular arc, the concave side of the arc being on the underside. The proximal portion is a shaft 50. In preferred embodiments of the invention, for ease of assembly the hollow elongate body is made from two separate pieces 51 and 52 which are joined together in the final step of the assembly of the body and the components that are found within. The body may be constructed of any suitable biocompatible material such as a hard inert polymer or metal. The distal end of the head contains an orifice through which a rigid circular hollow tube 34 passes. The rigid circular hollow tube comprises at its distal end a mechanism 30 by which connection can be made with an appropriately-sized surgical needle or lance 32, and is disposed within the head such that it can move back and forth and extend a sufficient distance from the end of the head such that the needle or lance can describe an essentially circular path through a circle of diameter equal to that of the arc described by the head. Means by which a surgical needle or lance can be attached to the end of the rigid circular hollow tube are well-known in the art.

In order to stabilize the bone during extension of the needle so that the needle can enter the bone as it is protrudes from the tool, the tool further comprises an extendable and retractable support element 54 that, when extended, will grasp the bone on a second point along the circumference of the bone, other that of the needle. The details of the mechanism by which the support element is activated are given below.

The driving mechanism of the tool is housed within driving mechanism housing 10 attached to the proximal end of the body. The control and mechanisms are located within the driving mechanism housing. A handle 12 is attached to the underside of the tool, either to the body or to the driving mechanism housing or to both. The movements of the hollow tool and the support element are controlled by independent control and driving systems. In the view shown in FIG. 1A, some of the elements of these control and driving systems are visible. Rotatable handle 18 is connected to the driving mechanism for the rigid circular hollow tube such that the motion of the distal end of the rigid circular hollow tube is proportional to the angle through which the handle is turned. Activation of quick-release tab 20 causes the rigid circular hollow tube to move directly to the end of its travel. Also visible in FIG. 1A are some of the components of the support element driving system. Rotatable knob 14 is connected to the driving mechanism of the support element such that the degree to which it is extended is proportional to the angle through which the knob is turned. Rotatable knob 18 comprises a central threaded orifice that engages threaded rod 24; as the knob is turned, it moves down the length of the threaded rod. The control mechanism also includes tab 22 which physically engages the driving mechanism for the support element. The tab includes an orifice that fits over the threaded rod distally to knob 14 and a stiff connector that connects the orifice to the distal end of the tab. The support element control mechanism also includes a quick-release pin 16, activation of which enables the support element to move directly to the end of its travel.

Figure 67A:
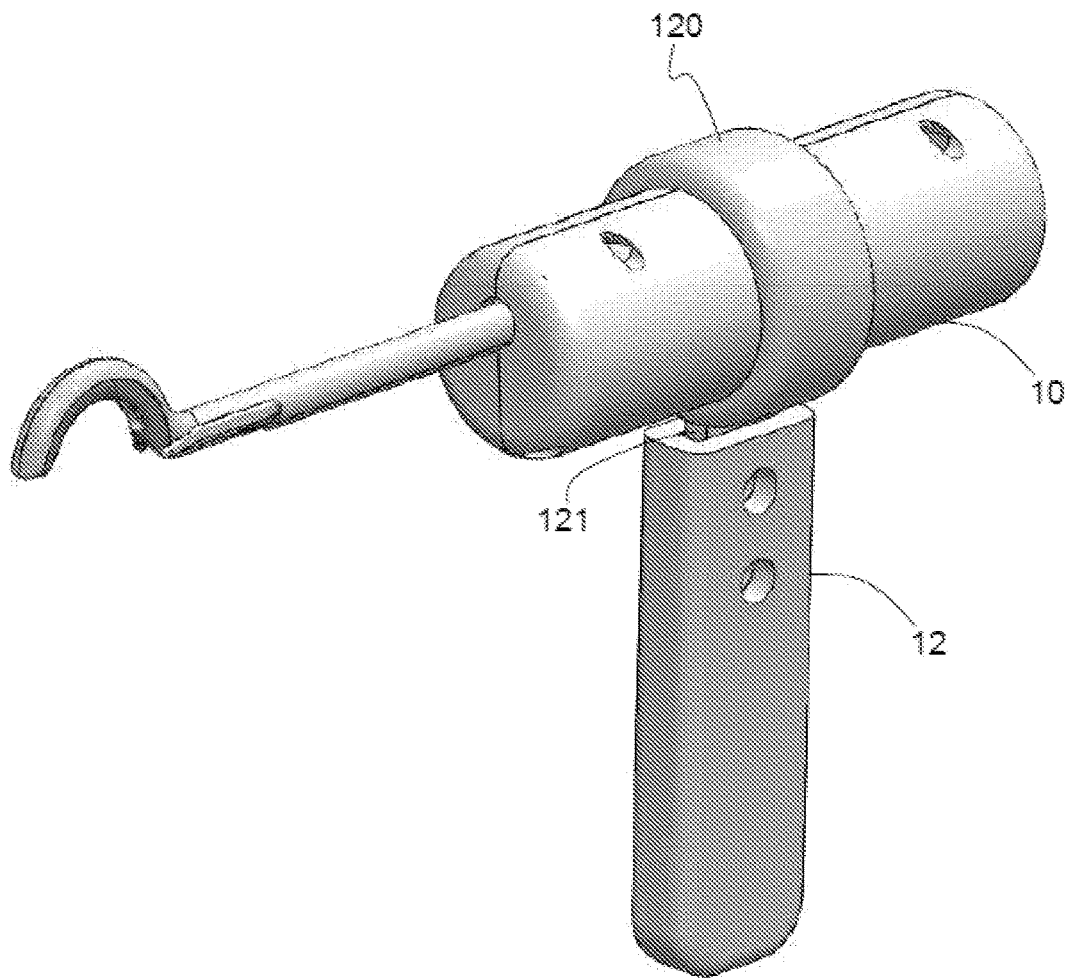
FIG. 67 illustrates an embodiment in which handle 12 can rotate and translate relative to driving mechanism housing 10.
Figure 67B:
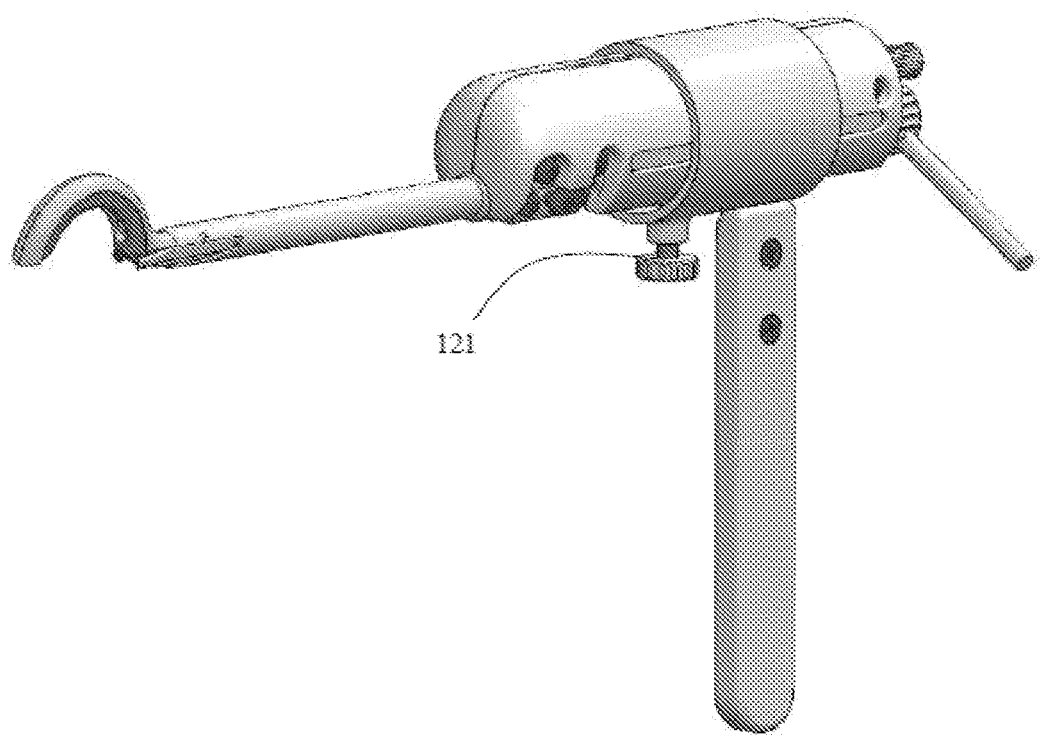

Reference is now made to FIGS. 67a-67b, which presents a view of the connection between handle 12 and housing 10 one preferred embodiment of the invention. In this embodiment, the handle is attached to the housing via sleeve 120 that surrounds the housing with a slip-fit sufficiently loose to allow relative movement of the sleeve and the housing. A mechanism 121 allows the interior of the sleeve to be constricted, thus fixing the sleeve in place when it has been set in its desired location. Mechanism 121 also allows, when loosened, the handle to rotate freely about its own longitudinal axis, and when tightened, the angle of rotation of the handle about its longitudinal axis to be fixed in place. Such mechanisms and means for activating them are well-known in the art. In these embodiments, the operator of the device can fix handle 12 in any desired location and orientation relative to the body of the device, and to change the relative location and orientation of the handle and the body to one that is more comfortable, provides better leverage, etc.

Reference is now made to FIG. 67b illustrating one possible embodiment of mechanism 121, according to this specific embodiment, mechanism 121 is a screw.

In some embodiments of the invention, it also includes means for determining how far the rigid circular hollow tube has traveled. In the embodiment illustrated in FIG. 1A, one side of the shaft includes a window 512. The rigid circular hollow tube driving mechanism includes a mark or other indicator 604 that is visible through the window and indicates the current position of the rigid circular hollow tube relative to the bounds of its travel. A mark 514 is placed on the body; when indicator 604 reaches mark 514, the user knows that the rigid circular hollow tube has reached the end of the travel.

Reference is now made to FIG. 69, which illustrates means for determining how far the rigid circular hollow tube has traveled according to other embodiments of the invention. In these embodiments, the device includes needle indicator 3200 and support indicator 5400. These indicators are designed to provide visual indications of the extent of travel of the needle and the rigid circular hollow tube, respectively. In the embodiment shown in FIG. 69A, the two indicators are colored tabs that ride in slots along the proximal-distal axis of the device. Needle indicator 3200 is in physical communication with the actuator for the needle, while support indicator 5400 is in physical communication with actuator 58 for support element 54. In both cases, the distance through which the indicator has traveled is proportional to the distance through which the corresponding component of the device has traveled.

Figure 69B:
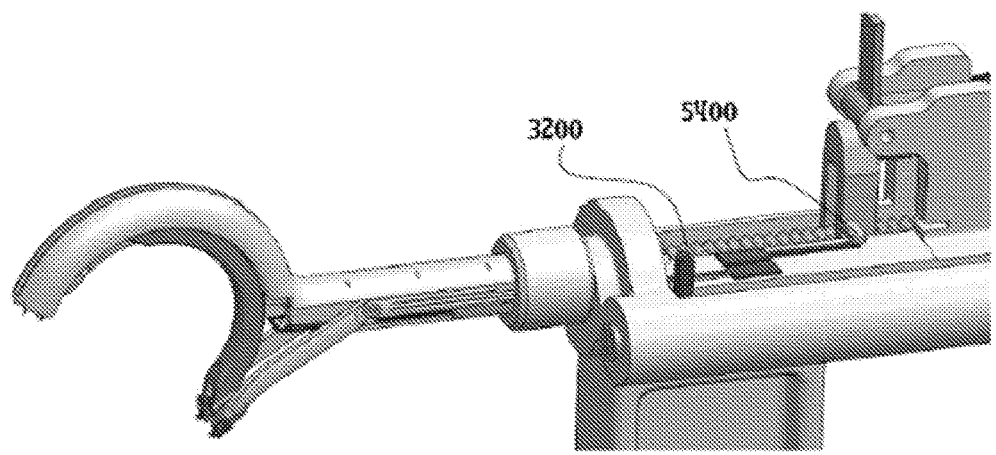

FIG. 69B illustrates the status of the two indicators prior to the beginning of the procedure. Needle indicator 3200 is fully at one end of its travel (fully forward in the embodiment illustrated), indicating that the hollow tube and therefore the needle is fully retracted. Likewise, support indicator 5400 is fully at one end of its travel (fully backward in the embodiment illustrated), indicating that the support element is fully retracted as well.

Figure 69C:
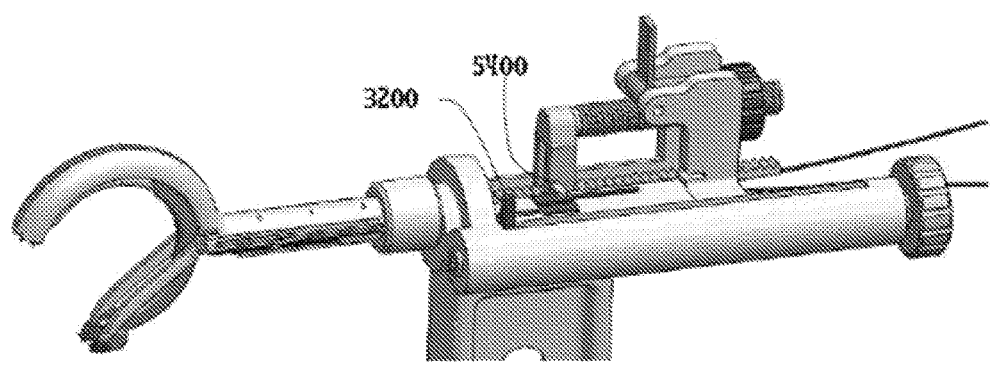

FIG. 69C illustrates the status of the two indicators after the support element has been extended, but while the needle remains fully retracted. Support indicator 5400 has now moved to the opposite end of its travel, while needle indicator 3200 remains in its initial position.

Figure 69D:
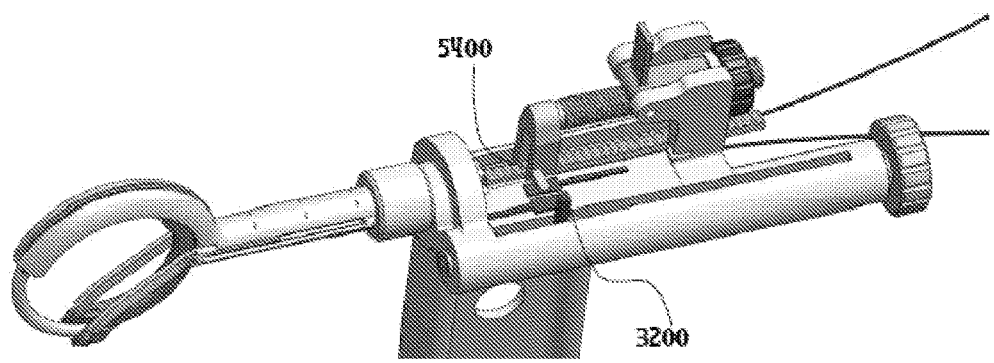

FIG. 69D illustrates the status of the two indicators after the needle has passed through the tendon and the bone. Now, both indicators are at the far end of their travel, indicating that the both the support element and the hollow tube are fully extended; full extension of the hollow tube indicates that the needle has passed through the bone and into the needle catcher. When both indicators have moved to the far end of their travel, the surgeon thereby knows that it is now possible to exchange suture 130.

Reference is now made to FIG. 1B, which provides an isometric view of embodiment 1000 after the left-hand side of the body 51 has been removed to reveal the interior of the hollow body. In this embodiment, the driving mechanism for the rigid circular hollow tube comprises a series of slidable members (beads) attached to one another. The interior of the body includes on its upper or lower side or both a track 522 that guides the movement of the slidable members. The distal slidable member 4 is flat on its forward side, which engages the proximal end of the hollow tube. The remaining slidable members 2 need not be flat on the forward side; as described in detail below, in preferred embodiments, they present a substantially circular profile. In this embodiment, the driving mechanism also includes at its proximal end rigid circular hollow tube actuator 6 that engages the rigid circular hollow tube control such that when the rigid circular hollow tube control moves forward, it causes the activator to move forward, thereby causing the slidable members to slide distally, pushing the hollow tube.

Also visible in the view shown in FIG. 1B is the activating mechanism for the support element. In this embodiment, the support element activating mechanism comprises an actuator 58 that engages at its proximal end the distal end of the support element control, and at its distal end support element connecting yoke 56 whereby forward movement of the support element control forces forward movement of actuator 58 (along axis 582) and hence forward movement of connecting yoke 56. The connecting yoke is pivotally connected to the support element via pivot element (e.g. a pin around which the assembly can rotate) 562. When activated, the support element moves along axis 542. It should be emphasized that the distal end of the support element, when activated, is located along the path formed by the rigid circular arc.

According to another embodiment, a circular cross section/profile of the shaft is provided. According to this embodiment, the circular profile ensures the best adhering/joining of the two parts of the incision (through which the circular tunneler/suture passer is being inserted). Such profile significantly reduces any leakage (of e.g. saline, which is typically used by surgeons to expand the inner volume) that may be developed during the operation.

The rigid circular hollow tube driving mechanism described above can provide a force of several hundred Newtons (especially, in the range of about 500 to about 600 Newton) to the hollow tube, which is more than sufficient for the rigid circular hollow tube to penetrate bone.

Figure 2A:
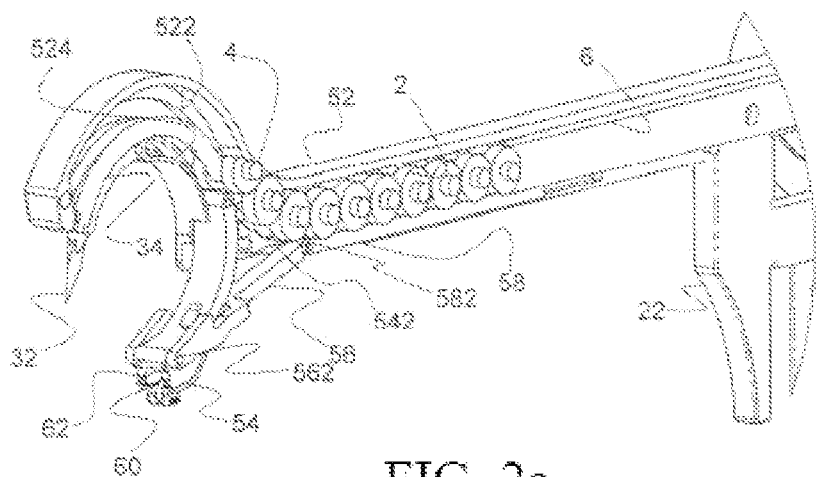
FIGS. 2a-2d presents a view of the curved/circular bone tunneling device or adjustable suture passer herein disclosed in which the support element has been extended.
Figure 2B:
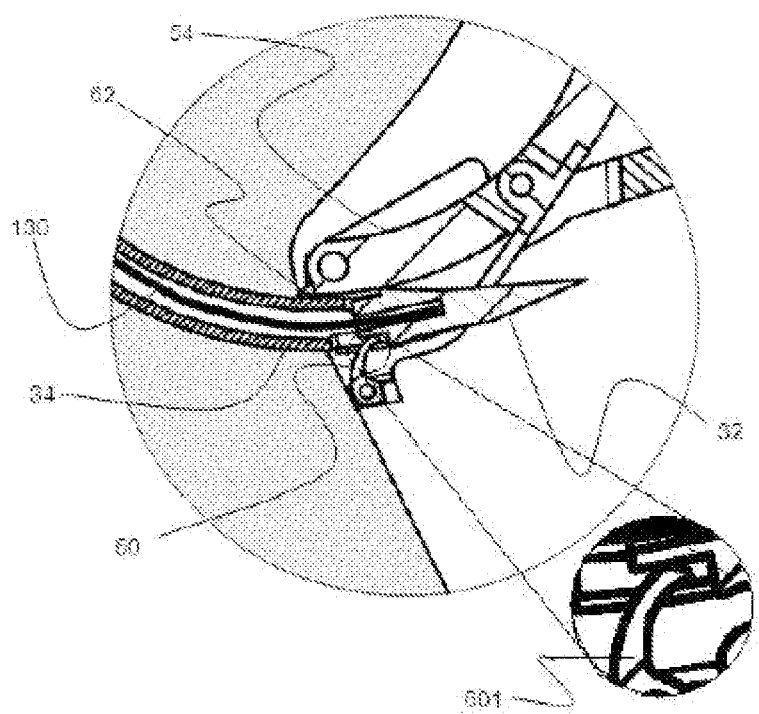

In order to insure that the protruding needle actually penetrates the bone rather than displacing the hollow elongate body head away from the bone surface, support must be provided to maintain the hollow elongate body head unit flush with bone surface by means of fixation of the unit to the bone circumference opposite to the side through which the needle enters. Hence, the tool comprises an extendable/retractable support element which, when extracted, extends from the underside of the tool opposite to the head. Reference is now made to FIGS. 2a and 2b, which shows embodiment 1000 of the tool after the support element 54 has been extended. In preferred embodiments of the invention, the support element additionally comprises a needle extractor 60.

The needle extractor 60 is responsible for maintaining penetrating element 32 within the support element 54. The same is enabled by means of a bore 601 located within the penetrating element 32, into which the needle extractor 60 penetrates so as to prevent the departure of penetrating element 32 from the support element 54.

Penetrating element 32 is a sharp element that can be pushed into the bone and penetrate through it. Penetrating element 32 pulls wire 130 with it (130 is connected to the proximal end of 60).

Once a full arc path from circumference point 1 to circumference point 2 through the bone has been formed, needle extractor 60 remains within the bore 601 [while the arched rigid hollow tube 34 returns back to housing 90.

Needle extractor 60 enables the penetrating element 32 to enter into support element 54 yet, ensures its release from the rigid circular hollow tube 34 when the same moved reversibly back into head.

Needle extractor 60 is an elastic element, bendable in one direction yet stiff in the opposite direction. Embodiment 1000 (illustrated in FIG. 1) discloses needle extractor 60 as a rigid hook rotating on an axis with a torsion spring pushing it.

It should be understood that several other embodiments may be utilized, however. For example, the mechanical properties of the needle extractor 60 (namely, its elasticity and spring-like properties) can be exploited.

Figure 2C:
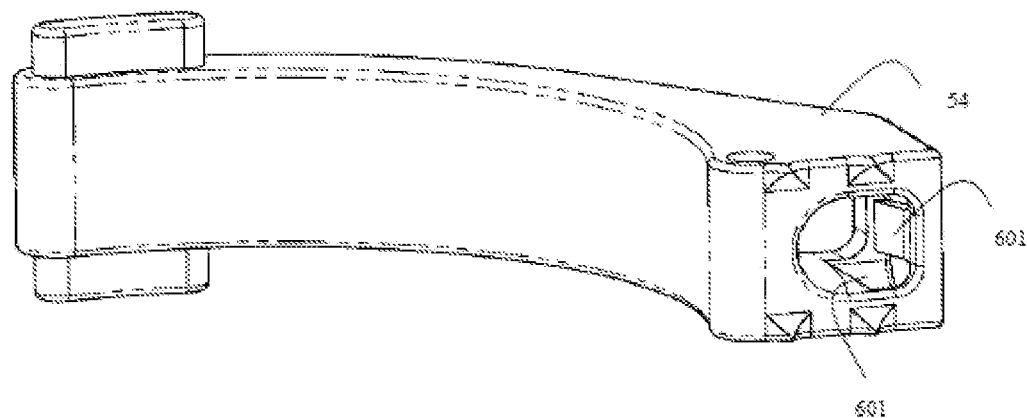
Figure 2D:
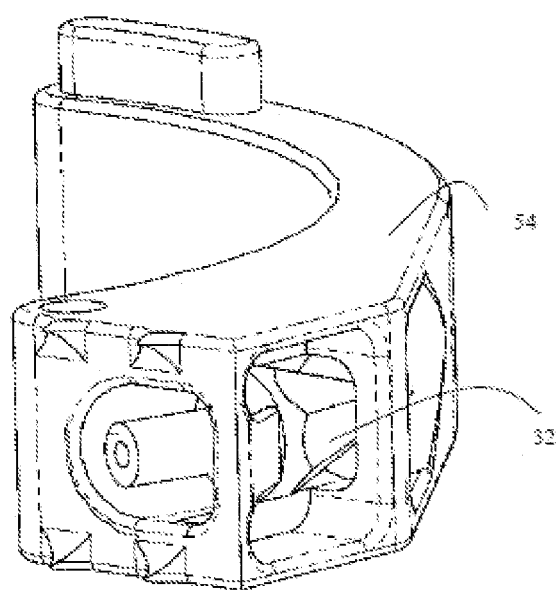

Reference is now made to FIGS. 2c and 2d, which illustrate an embodiment in which the spring-like properties of the needle extractor 60 is utilized.

In such an embodiment, the needle extractor 60 may be integrated into support element's 54 internal surface. According to this embodiment, the needle extractor 60 is characterized by two configurations, an extended configuration and a retracted configuration.

In the extended configuration, the needle extractor 60 substantially reduces the inner diameter of support element

54; and, in the retracted configuration of the needle extractor 60, the inner diameter of support element 54 remains substantially the same.

Due to the needle extractor's 60 spring-like properties, it can be reconfigured from the extracted configuration to the retracted configuration by application of force on the same. Once no force is applied, the needle extractor 60 is reconfigured back from the retracted configuration to the extended configuration.

The default configuration of the needle extractor 60, according to this embodiment is the extended configuration, in which the inner diameter of support element 54 is reduced.

Once the penetrating element 32 enters the support element 54, the needle extractor 60 is reconfigured from the extended configuration to the retracted configuration and applies pressure on the penetrating element 32, so as to maintain the same within support element 54.

It should be emphasized that the support element 54 may comprise either one or a plurality of said needle extractors 60.

Reference is now made to FIG. 2*d* which illustrates the above mentioned embodiment, but with the penetrating element 32 integrated within the support element 54.

FIG. 2*b* illustrates a close up view of how the needle extractor 60 functions once penetrating element (e.g., needle or lance) 32 are within the support element 54 and after the rigid circular hollow tube 34 is drawn back.

It should be noted that the distal face of element 54 is equipped with prongs 62, adapted to prevent any movement of the support element 54, once the same is positioned at desired location.

In preferred embodiments, the needle extractor is disposed on the underside of the support element and comprises a hollow receptacle into which the penetrating element (needle or lance) 32 enters upon reaching circumference point 2.

When either the support element or the rigid circular hollow tube is retracted following use of the tool, the penetrating element remains within hollow receptacle of the needle extractor 60.

Figure 3:
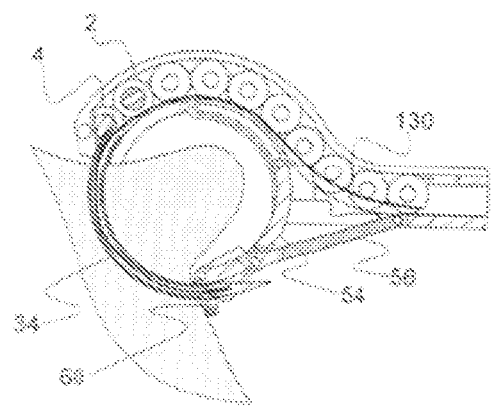
FIG. 3 presents a cross-sectional view of the distal end of the curved/circular bone tunneling device or adjustable suture passer herein disclosed illustrating its use to insert a guide wire through a bone.

Reference is now made to FIG. 3, which shows a cross-sectional view of embodiment 1000 of the tool after the rigid circular hollow tube has completed its travel. A guide wire 130 passes through the rigid circular hollow tube and is attached to the proximal end of the lance 32 (which in this view has passed through the bone, shown as a shaded region in the figure).

A suture can then be attached to the distal end of the guide wire and passed through the soft tissue and into and through the bone. In the view shown in FIG. 3, the needle has entered into the needle extractor 60.

Figure 4:
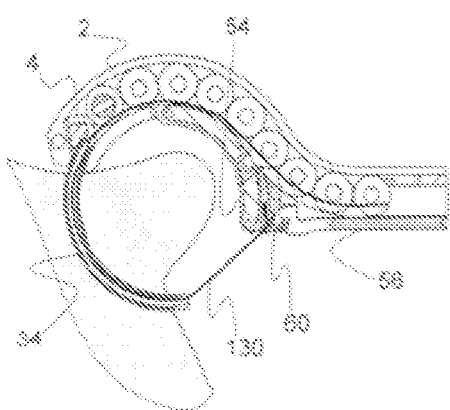
FIG. 4 presents the same view as in FIG. 3, but after the support element has been retracted.

Reference is now made to FIG. 4, which shows a cross-sectional view of the tool after the support element has been retracted. In this view, the rigid circular hollow tube is still within the bone, and needle can be seen to have remained within the needle extractor, carrying guide wire 130 with it.

A cavity in retractable support element 54 provides a 'nesting volume' for the penetrating element 32 securing it to its position, so as to prevent any damage to surrounding tissues.

Reference is now made to FIGS. 5A-5D, which illustrate the distal end of another preferred embodiment of the tool. According to this embodiment, an additional radial support is provided to rigid circular hollow tube 34 sections that aren't yet within the bone in order to ensure that at the end of its travel it will engage needle extractor 60.

In this embodiment, the support element further comprises a tab 5421 that protrudes through a slot 5422 in one side of the head (90).

Tab 5421 slides in a slot 5422 so as to indicate the current position of the rigid circular hollow tube relative to the bounds of its travel.

Most significantly, this embodiment further includes rigid support element 70. The support element is located between the right and left halves of the head; in a preferred embodiment of the device, the head and body are manufactured from two matching pieces that form the left and right halves of the device when it has been assembled.

Figure 5A:
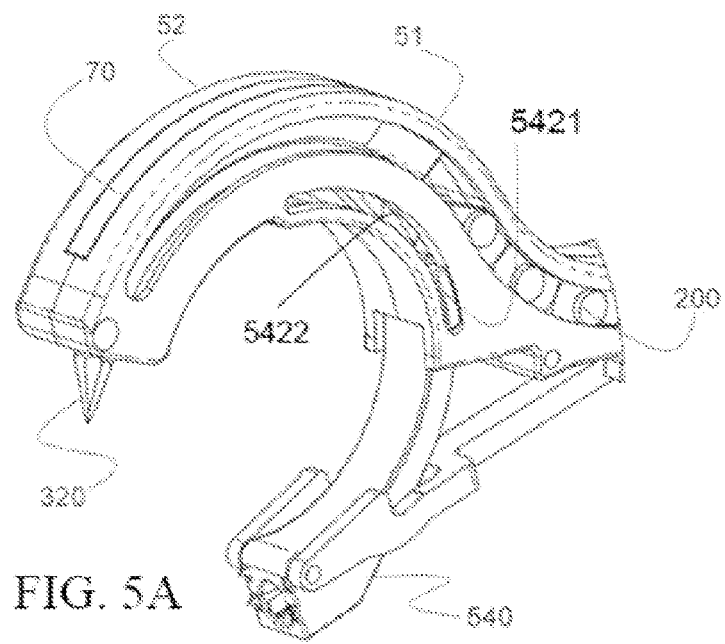
FIGS. 5a-5d presents views of the distal end of another preferred embodiment of the invention.

FIG. 5A shows an external view of head 90, including rigid support element 70. The same illustrating how it sits between the two halves of the head.

Figure 5B:
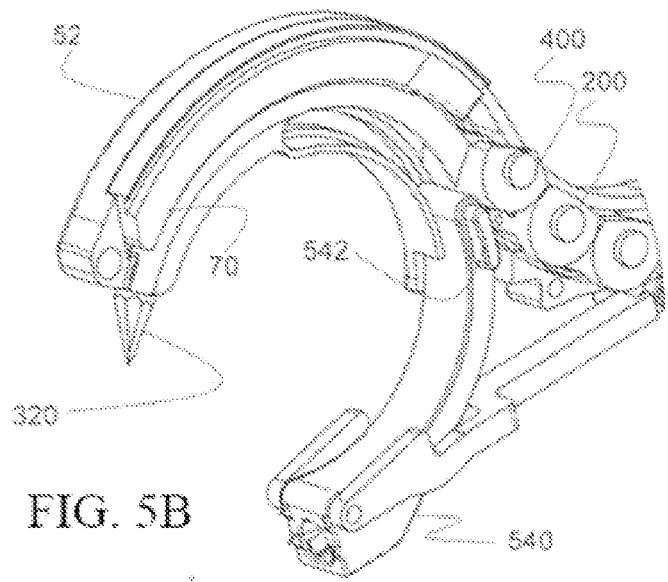
Figure 5C:
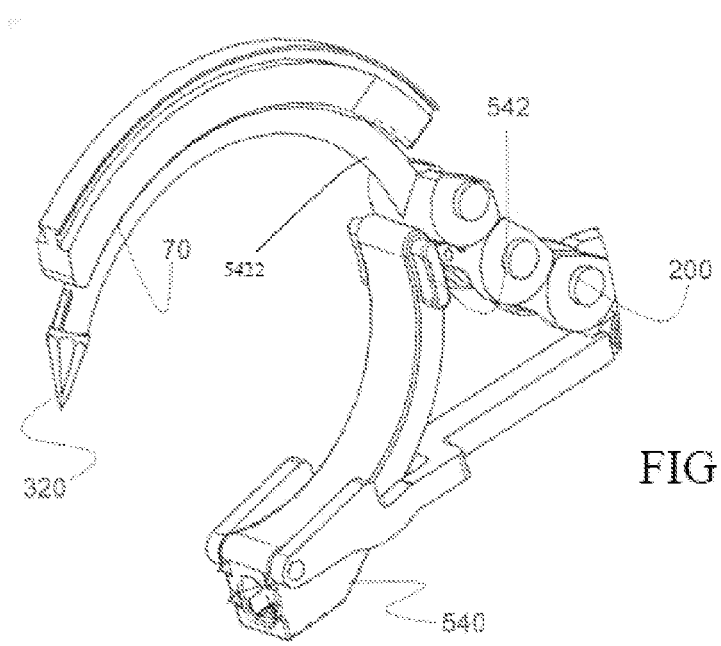
Figure 5D:
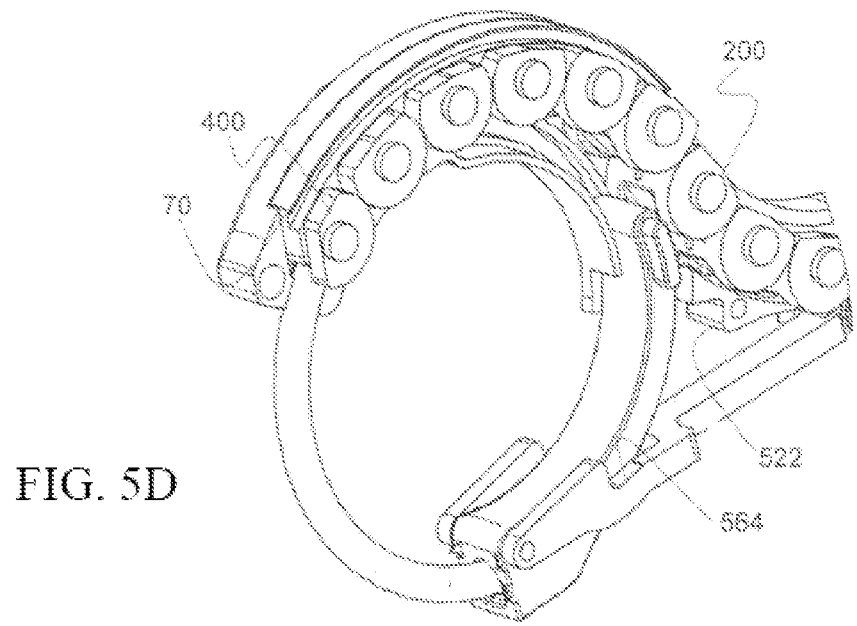

FIG. 5B shows a partial cutaway view of the head with support element 70 in place. An isometric view of rigid support element 70 can be seen in FIG. 5C. Support element 70 has the shape of an arc with essentially the same curvature as the upper portion of head 90. Slots on either side of the support element hold it in place between the two halves of the head when it is assembled. Support element 70 has a depth sufficient to contact rigid circular hollow tube 34 while not hindering the movement of the hollow tube. Rigid support element thus provides additional support to rigid circular hollow tube 34 and prevents it from bending or crimping (and any other deformation) such that the rigid circular hollow tube is constrained to move only along a path that will return it to needle catcher 60, as shown in FIG. 5D and FIG. 6D

Figure 6A:
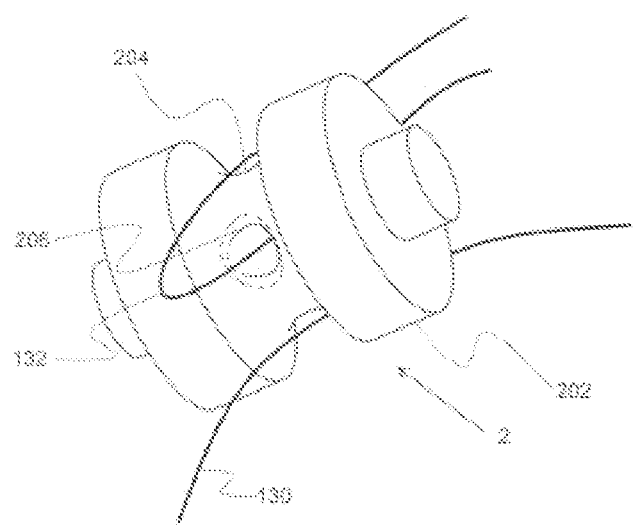
FIGS. 6a-6d presents illustrations of slidable members 2 and 4 according to a preferred embodiment of the invention.

Reference is now made to FIG. 6A, which illustrates a preferred embodiment of slidable member 2. In preferred embodiments, the slidable member is substantially cylindrical in shape, with an indentation 204 around the waist of the cylinder (i.e. around its circumference and perpendicular to the cylinder's longitudinal axis). The indentation allows guide wire 130 to pass unhindered. At least one of the ends 202 fits into track 522 that enables the member to slide along the distal-proximal axis of the body. Note that even though the member has a circular cross-section, it does not roll along the track.

A channel 206 passes through the slidable member along an axis substantially perpendicular to the longitudinal axis of the cylinder. A connecting wire 132, disposed along the proximal-distal axis of the body, passes through the channel, thereby connecting the plurality of slidable members. The connecting wire is formed into a loop, the proximal end of which engages the rigid circular hollow tube driving mechanism, enabling the rigid circular hollow tube to be retracted after the tool has been used. As shown in the figure, as with guide wire 130 the leg of the loop in connecting wire 132 that does not pass through the channel passes outside the slidable member via indentation 204.

Figure 6B:
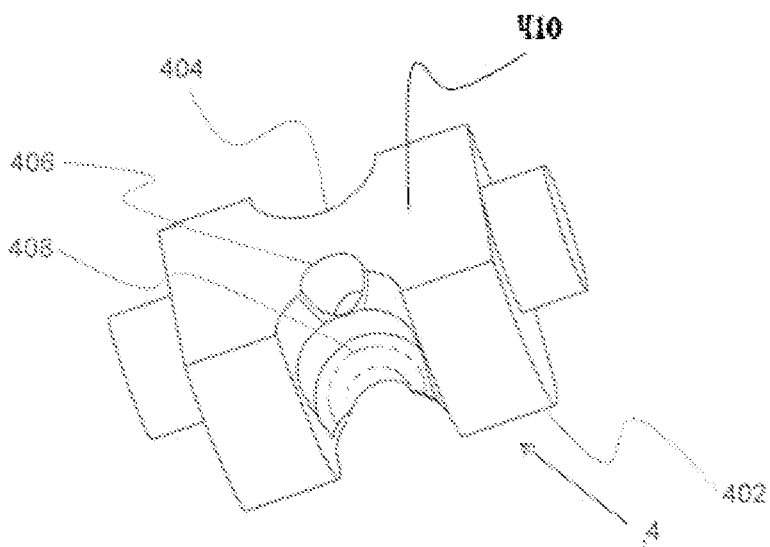

Reference is now made to FIG. 6B, which illustrates a preferred embodiment of distal slidable member 4. The overall cylindrical shape 402, indentation 404, and channel 406 are analogous to components 202, 204, and 206 of slidable member 2 illustrated in FIG. 5A. Unlike the other slidable members, the distal slidable member directly engages/actuates rigid circular hollow tube 34. Thus, it is provided with a flat face 410 that is oriented facing forward (i.e. in the direction of motion toward head 90), and a channel 408 that fits over the proximal end of rigid circular hollow tube 34 and, in preferred embodiments, is physically connected thereto.

Figure 6C:
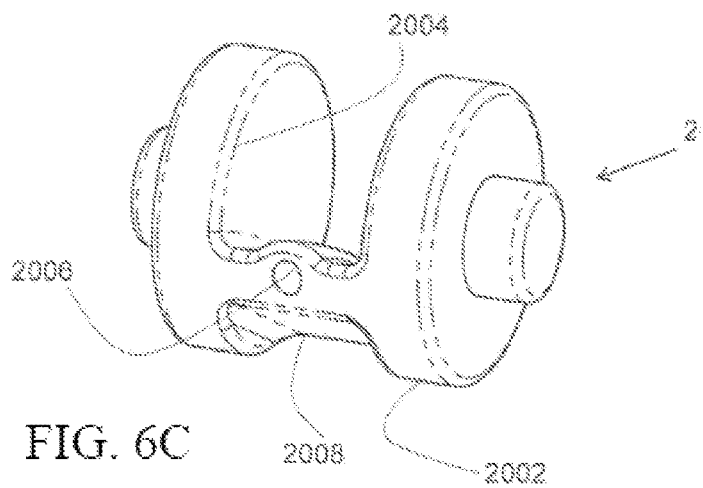
Figure 6D:
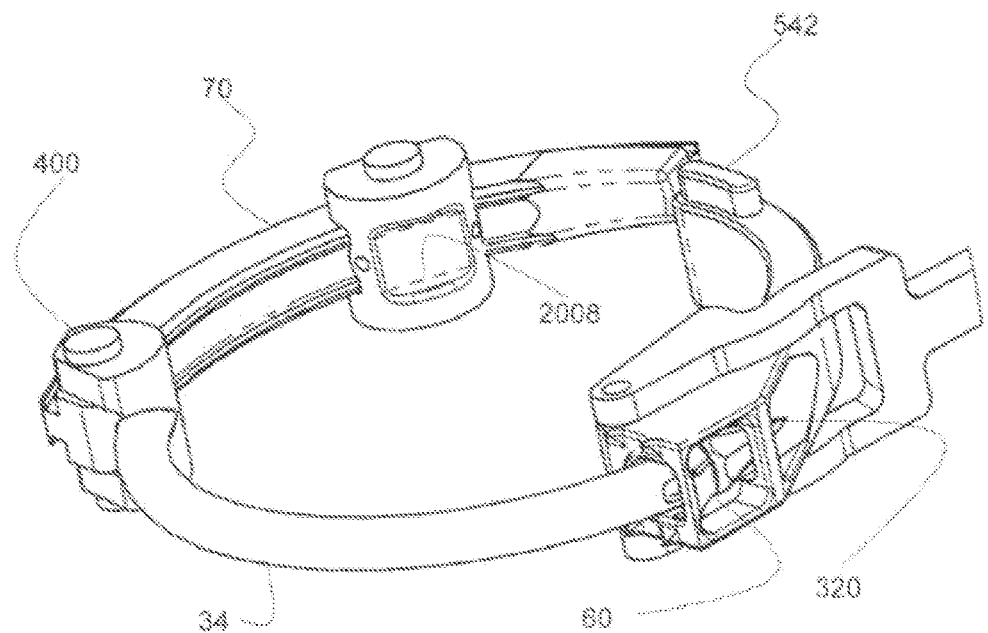

In embodiments of the invention that incorporate rigid support member 70, slidable members 2 have a somewhat different configuration from that shown in FIG. 6A. The configuration of slidable member 2 in these embodiments is shown in FIG. 6C. While the slidable member retains its generally cylindrical shape, the indentation is no longer symmetrical about the axis of the cylinder. Rather, indentation 2004 is cut through most of the diameter of the cylinder so that the slidable member 2 may pass under support element 70. Consequently, channel 2006 adapted to allow passage of connecting wire 132 is displaced from the center, as shown in the diagram. A second indentation 2008 is made on the opposite side of the member to allow passage of guide wire 130. One side of the cylinder (2002) is adapted to slide on track 522. A schematic assembly diagram showing support member 70, slidable member 2, and rigid circular hollow tube 34 in its extended position (i.e. after the needle attached to it has reached needle catcher 60), is given in FIG. 6D.

Figure 7:
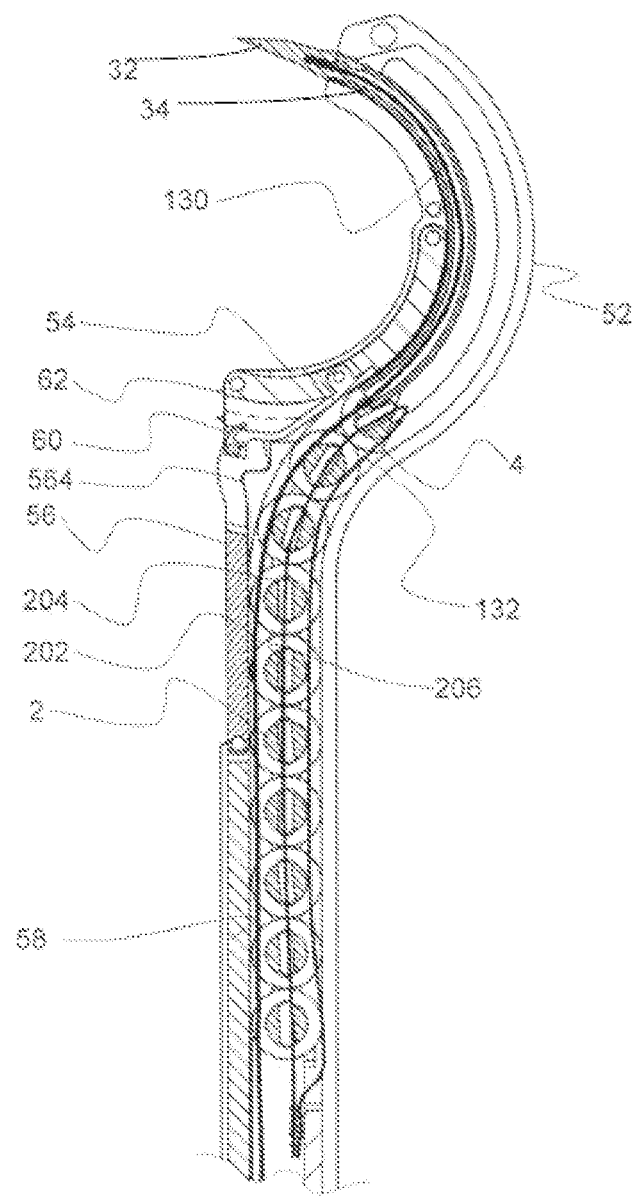
FIG. 7 presents a cross-sectional view of the assembly of the rigid hollow tube driving mechanism according to a preferred embodiment of the invention.

Reference is now made to FIG. 7, which presents a cross-sectional view of the assembly of the rigid circular hollow tube driving mechanism according to one embodiment of the invention. The slidable members are connected via connecting wire 132 through orifices 206 and 406 to form a train. Connecting wire 132 loops back through indentations 204 and 404; the proximal end of the loop engages the rigid circular hollow tube control such that when the rigid circular hollow tube control is activated, the slidable members move in tandem, thereby moving the rigid circular hollow tube 34 and the needle or lance 32 connected to its distal end. Guide wire 130 passes through indentations 204 and 404, whereby motion of the guide wire, which as described above passes through the rigid circular hollow tube 34 and is connected to needle or lance 32, is unimpeded.

Reference is now made to FIG. 8, which presents isometric views of the hollow tube (driving mechanism) control according to a preferred embodiment of the invention.

The control mechanism is disposed within and about driving mechanism housing 10. Rotatable knob 18 comprises a substantially circular handle (in preferred embodiments, it is knurled or its circumference is provided with a plurality of indentations or protrusions for ease of handling) and a hollow shaft 186 the internal wall of which is threaded. Driving mechanism housing 10 comprises a channel of internal diameter appropriate to provide a slip fit to hollow shaft 186 and a distal wall with an orifice through which hollow tube actuator 6 passes. The threaded shaft further comprises a groove 182 around the circumference of its external wall, substantially perpendicular to the longitudinal axis of the shaft, and disposed substantially at its distal end. The threaded hollow shaft engages a threaded rod 602 which is physically connected to the proximal end of hollow tube actuator 6. A hollow tube driving mechanism release tab 20 is pivotably connected to the body of driving mechanism housing 10. The hollow tube driving mechanism release tab comprises two protrusions extending from the central pivoting body, one of which (212) engages groove 182 and one of which extends above driving mechanism housing 10 used for handling.

Figure 8A:
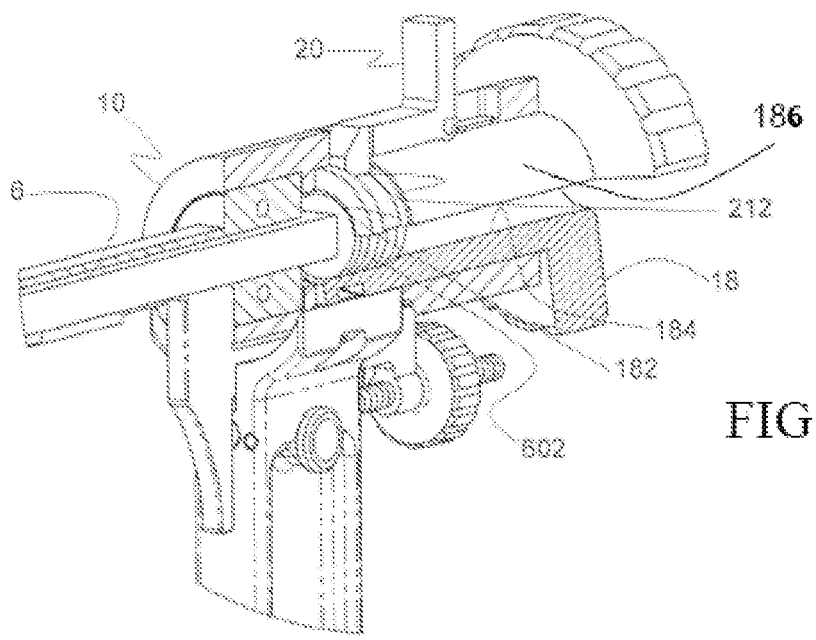
FIGS. 8a-8b presents isometric views of the rigid hollow tube control according to a preferred embodiment of the invention.

FIG. 8A shows a view of the hollow tube control as it appears when the driving mechanism release tab 20 is in its engaged position. In this configuration, protrusion 212 prevents handle 18 from moving along the distal-proximal axis of the body, so rotation of the handle causes threaded rod 602 to travel along the length of the shaft, thereby driving hollow tube actuator 6 and, via the remainder of the hollow tube driving mechanism (not shown in FIG. 8) engaged by actuator 6, slidable member (e.g., 2 and 4) and hollow tube 34 such that the distance through which the hollow tube moves is proportional to the angle through which knob 18 is rotated. In FIG. 8A, the threaded rod is shown at the most distal point of its travel; further movement of the threaded rod is blocked by the distal wall of driving mechanisms housing 10.

Figure 8B:
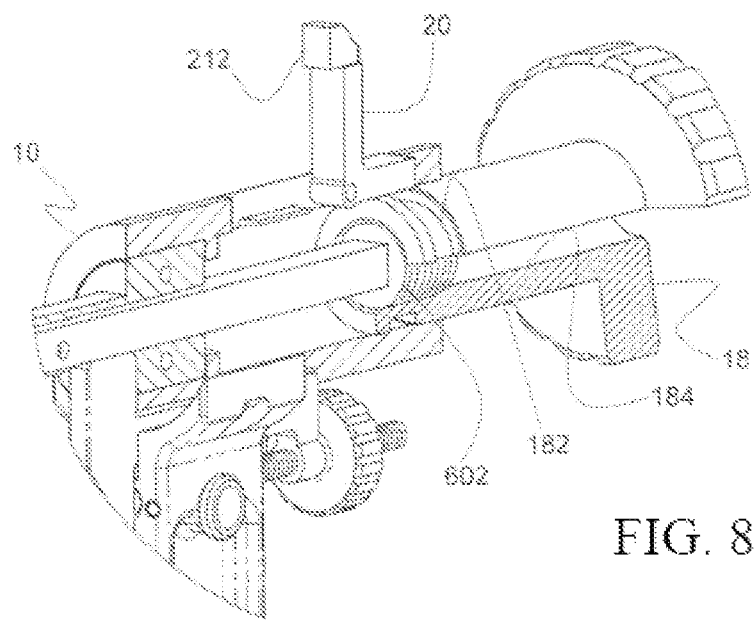

Application of pressure to its external protrusion activates tab 20, moving protrusion 212 to its disengaged position. FIG. 8B shows the hollow tube control with tab 20 in its disengaged position. Since in this configuration motion of knob 18 along the distal-proximal axis of the tool is unhindered, it is possible in this case to move hollow tube 34 by pushing or pulling knob 18 without turning it. By pulling knob 18 to the proximal direction hollow tube 34 is retrieved back into 90.

Reference is now made to FIG. 9, which presents isometric views illustrating the support element control according to a preferred embodiment of the invention. FIG. 9A shows an external view, while FIGS. 9B and 9C illustrated the internal mechanism of the support element control with handle 12 removed. In the embodiment of the support element control illustrated in FIG. 9, it comprises a threaded rod 24 and a quick-release pin 16. Quick-release pin 16 is adapted such that when it is in its disengaged position (as in FIG. 9B), motion of the threaded rod (both axial and rotational) is blocked, while when it is in its engaged position (as in FIG. 9C), motion of the threaded rod is permitted.

The support element control further comprises rotatable knob 14, which comprises an internally-threaded orifice that engages the threads of threaded rod 24. As with rotatable knob 18, in the most preferred embodiments, the circumference of knob 14 is knurled or provided with a plurality of indentations or protrusions for ease of handling. The control also comprises a slider, which comprises a tab 22, a circular orifice 26 of internal diameter at least sufficient to provide a slip fit over threaded rod 24, and a rigid connector that attaches the orifice to the tab. Tab 22 comprises a portion 27 that slides along the underside of shaft 50 and a protrusion that extends below the shaft. The distal portion of In some embodiments of the circular tunneler/adjustable suture passer that comprise this embodiment of the support element control, the underside of shaft 50 comprises a slot that allows the protrusion to move freely along the proximal-distal axis of shaft 50; in other embodiments, shaft 50 comprises a track on the exterior of its underside in which tab 22 and those portions of the support element driving mechanism engaged thereby slide.

In the embodiment of the support element control illustrated in FIG. 9, it engages the support element driving mechanism as follows. As knob 14 is turned, it travels along the length of threaded rod 24. When the travel is in the distal direction, the knob will engage orifice 26, thereby causing tab 22 to move in the distal direction. As sliding portion 27 moves distally, it engages the proximal end of the support element driving mechanism (e.g. actuator 58), thereby causing the support element to extend. When the user wishes to retract the support element, knob 14 is turned in the opposite direction, causing it to travel proximally along threaded rod 24. This motion will then leave a gap between knob 14 and orifice 26. Tab 22 can then be moved in the proximal direction manually by application of pressure to the portion that extends beneath shaft 50.

As shown in FIG. 9B, when quick-release pin 16 is in its engaged position, it prevents threaded rod 24 from moving, either by physically holding it (e.g. via a retractable vise-like grip) or by engaging an indentation in the threaded rod.

When pin 16 is disengaged, as shown in FIG. 9C, it no longer prevents movement of threaded rod 24. In a manner analogous to that of driving mechanism release tab 20, engagement of the quick-release pin permits the user to manually move the support element control without the necessity of turning knob 14.

Figure 10:
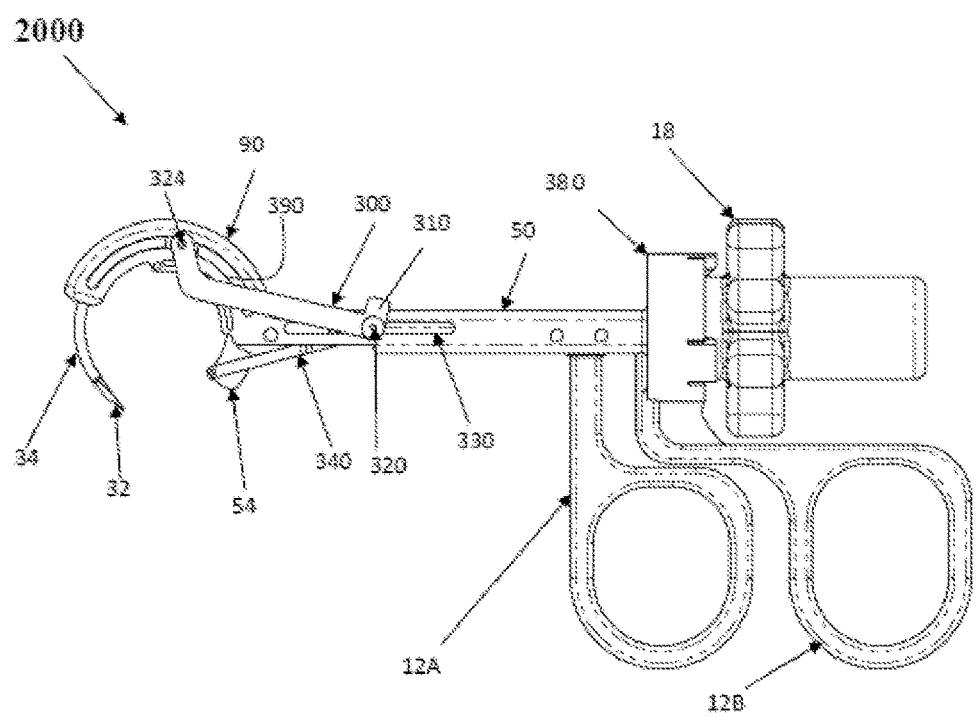
FIG. 10 presents a view of the curved/circular bone tunneling device or adjustable suture passer disclosed herein according to another embodiment of the invention.

Reference is now made to FIG. 10, which shows a view of a second embodiment 2000 of the circular tunneler/adjustable suture passer herein disclosed. The embodiment shown in FIG. 10 incorporates additional embodiments of the hollow tube and support element driving mechanisms and of the support element driving mechanism.

In the embodiment of the hollow tube driving mechanism shown in FIG. 10, shaft 50 incorporates body slot 330 along at least part of the length of at least one side of the body, and head 90 incorporates head slot 390 along at least part of the length of at least one side of the head. Slider 310 engages the hollow tube control at its proximal end. Yoke 300 is pivotably connected to slider 310 by pin 320 that passes through body slot 330, and is pivotably connected to the proximal end of hollow tube 34 by pin 324 that passes through head slot 390. When the hollow tube control is engaged, pin 320 travels distally, whereby yoke 300 forces hollow tube 34 to travel distally in proportion to the distance through which slider 310 has traveled. In this embodiment, the hollow tube control further comprises bearing housing 380.

FIG. 10 also shows a second embodiment of the support element driving mechanism. In this embodiment, the support element driving mechanism comprises an actuator 58 that engages at its proximal end the support element control and that is pivotably connected substantially at its distal end to a yoke 340 via a pin (not shown in FIG. 10). Yoke 340 is pivotably connected substantially at its distal end to the support element. When the support element control is engaged, actuator 58 travels distally, whereby yoke 340 moves downward, causing the support element to extend. In the embodiment shown in FIG. 10, handle 12 comprises two portions, a movable distal portion 12A and a stationary proximal portion 12B. In the embodiment shown, the handle is designed such that the user can grip it by placing his or her fingers through orifices at the bottom of the two portions of the handle. The movable distal portion of the handle further comprises a tab that fits into a slot in the underside of shaft 50.

In this embodiment, the support element control comprises the movable portion of the handle, which engages actuator 58; in preferred embodiments, the two are physically connected. As the movable portion of the handle is moved, actuator 58 moves in tandem, forcing yoke 340 to move and thereby extending or retracting the support element.

Figure 11A:
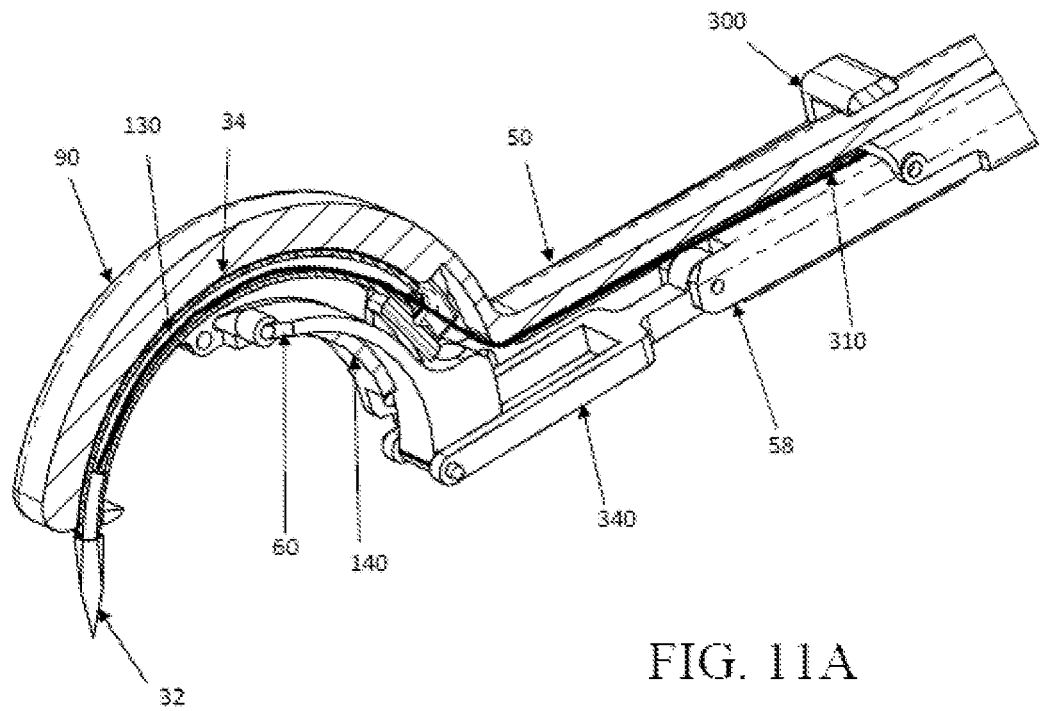
FIGS. 11a-11b presents interior views of the distal end of the curved/circular bone tunneling device or adjustable suture passer disclosed herein according to said second embodiment of the invention.
Figure 11B:
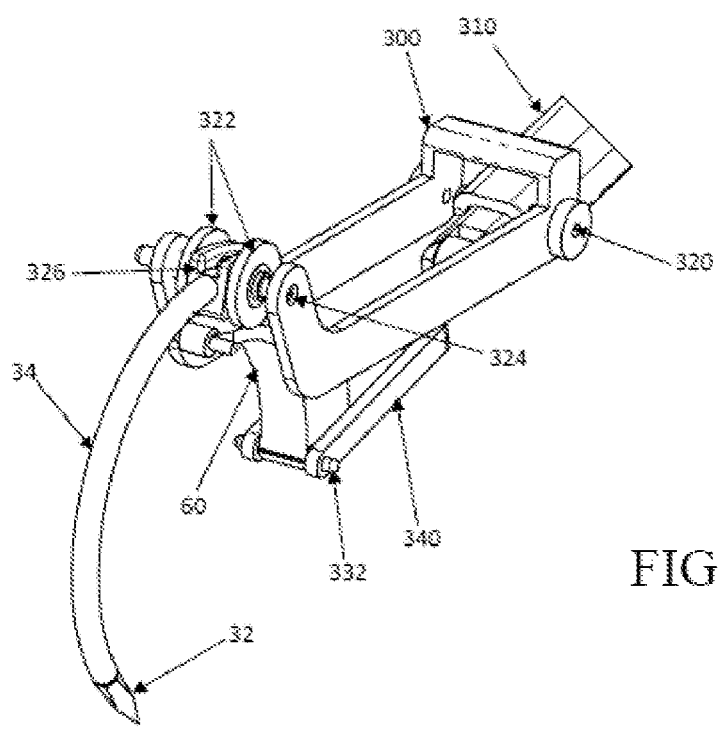

Reference is now made to FIG. 11, which shows views of the interior of the distal end of the circular tunneler/adjustable suture passer according to this second embodiment of the invention. The view shown in FIG. 11A illustrates how guide wire 130 passes through the head and shaft, and how the hollow tube actuator 58 engages yoke 340. FIG. 11B illustrates the workings of the support element driving mechanism according to this embodiment of the invention. When actuator 58 (shown in FIG. 11A, not shown in FIG. 1B) moves distally, it engages yoke 340. Substantially at its distal end, the yoke is connected to support element 54 via bearing 332. As the yoke descends in tandem with the motion of the actuator, the support element is pulled downward and forward, thus extending into its working position.

In the embodiments described thus far, the actuation of the device is performed manually. Reference is now made to FIG. 12, which presents a schematic illustration of an embodiment in which the hollow tube control and support mechanism control are actuated electrically. Motor 700 engages at least one of rotatable knobs 14 and 18. In the embodiment shown in the figure, each of the two rotatable knobs is engaged by a motor; motor 700A engages rotatable knob 14 and motor 700B engages rotatable knob 18. Any type of motor known in the art appropriate for actuating a medical device may be used. In preferred embodiments of the invention, motors 700A and 700B are DC stepper motors. FIG. 12A shows an overall schematic of such an embodiment. FIG. 12B presents a closer view of the hollow tube and support element controls. In these embodiments, rather than a knurled nut, each rotatable knob comprises a gear 720 (720A and 720B). Motors 700 (700A and 700B) drives gear 710 (710A and 710B, respectfully), which in turn drives gear 720 (720A and 710B, respectfully). FIG. 12C presents a cutaway view of the two rotatable knobs, illustrating the internal threads of the knobs and the threaded rods that the knobs engage, showing how the motor actuates the control mechanisms. Said gearing elements basically transform the motor's rotational input into two axial, linear, independent and juxtaposed moves.

In some embodiments of the invention, it further comprises a tendon holder. Any tendon holder known in the art that can be adapted for use with the present invention may be used.

The term "tendon holder" refers hereinafter to any device which enables the grasping of a tendon and pass of a suture through the same.

Figure 13A:
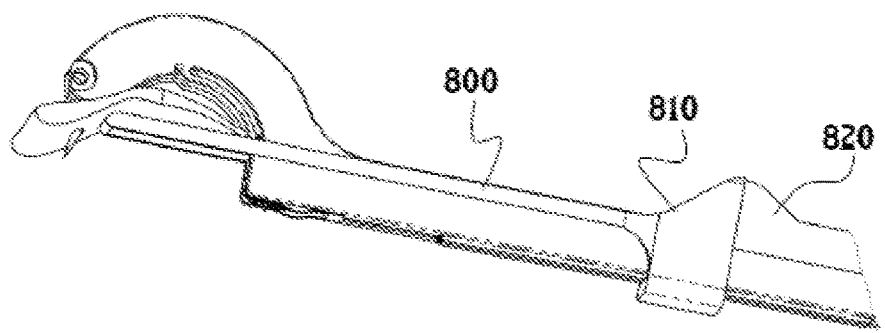
FIGS. 13a-13b presents a schematic view of an embodiment of the present invention in which it further comprises a tendon holder.

Reference is now made to FIG. 13, which illustrates a preferred embodiment of a tendon holder especially adapted for use with the invention herein disclosed. FIG. 13A presents a view of the distal portion of the circular bone tunneling device/suture passer showing the tendon holder. The tendon holder comprises grasping member 800, slider 810, and manipulator 820.

According to another embodiment, the tendon holder may comprise a single manipulator that enables both pushing and/or pulling movements.

Figure 13B:
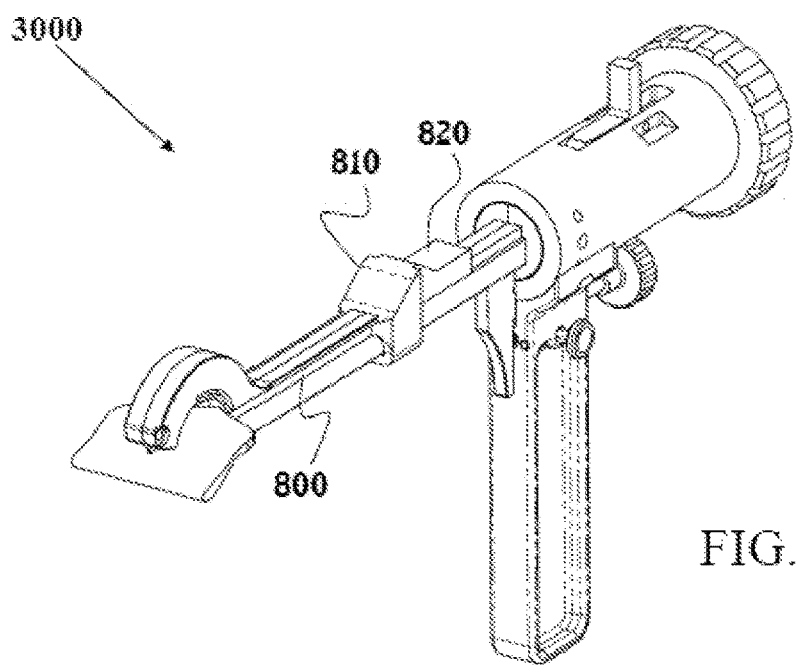

The slider is attached to the hollow elongate body of the circular tunneler/suture passer such that it can slide back and forth along the body. For example, it can comprise a channel with internal dimensions chosen to provide a slip fit over the body. Manipulator 820 is attached to the proximal side of the slider and sits on the upper side of the body. As can be seen in the diagram, in preferred embodiments, the manipulator has an ergonomic shape such that it can be pushed and pulled by the thumb of the operator of the device. Grasping member 800 is attached to the distal side of the slider. It is disposed on the upper side of the elongate body and slides along the distal-proximal axis of the body on the upper side of the body and passes under the head at the point at which the head is attached to the body. As can be seen in the diagram, in preferred embodiments, it has an elongated shape (e.g. a parallelepiped that is wider than it is high) and has a length sufficient that when it is moved to the distal end of its travel, it reaches sufficiently close to the distal end of head 90 that a tendon can be grasped between the distal end of the grasping member and the underside of the head. In the most preferred embodiments, when the grasping member is retracted to the most proximal point of its travel, it does not extend beyond the end of the body of the circular bone tunneling device/suture passer. An overall view of an embodiment 3000 of the device that comprises a tendon holder is shown in FIG. 13B.

It is also within the scope of the invention to disclose a method for tunneling through a bone during arthroscopic surgery. The method comprises steps of (a) providing a curved bone tunneling device comprising: (i) a hollow elongated body defining a rigid circular arc; said hollow elongated body comprising a surgical needle adapted to tunnel through a bone along a path formed by said circular arc; and, (ii) an extendable and retractable support element, reconfigurable from at least one extended configuration to at least one retracted configuration; (b) positioning said hollow elongated body of said device adjacent to the circumference of a bone; (c) fixating said needle to said bone; (d) extending said retractable support element to a location along the path formed by said circular arc; thereby grasping said bone with said support element and said hollow elongated body at two points along the circumference of said bone; (e) actuating said hollow tube and said needle, thereby tunneling through said bone along said circular arc path; wherein said step of tunneling through said bone is performed without drilling.

It is also within the scope of the invention to disclose a method for attaching soft tissue such as a ligament to a bone without the use of an anchor. The method comprises the following steps. A guide wire is passed through a device capable of imparting sufficient force to a surgical needle such that the surgical needle will pass through bone. A surgical needle or lance is attached to the guide wire and then connected to the distal end of the device. The device is then inserted into position. A support element engages the bone through which the needle is to be inserted on a side of the bone opposite that into which the needle is to be engaged, i.e. it holds the bone from the side towards which it would tend to move when the needle hits the bone's surface. The device is then engaged, causing the needle (and the guide wire attached thereto) to pass through the bone. A suture is attached to the proximal end of the guide wire. The guide wire is pulled through the bone, carrying the suture with it. Once the suture has passed through the bone, the guide wire is detached and discarded.

Figure 14:
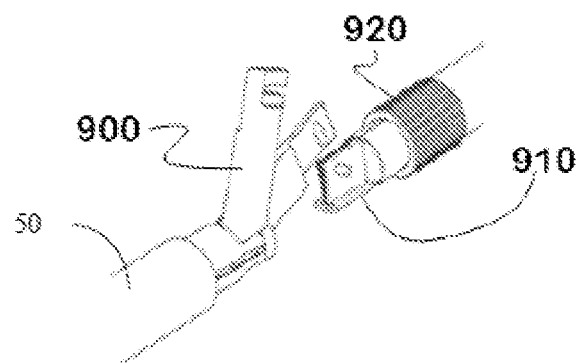
FIG. 14 presents a schematic view of an embodiment of the present invention, utilizing a motorized tool in which decoupling of the shaft is enabled.

Reference is now made to FIG. 14 which illustrates an embodiment in which the decoupling of the shaft (50) is enabled.

In other words, FIG. 14 presents a schematic view of a connector for rapid connection and disconnection of the shaft. Such a connector is particularly useful for embodiments that comprise motorized control.

In some embodiments of the invention in which it the circular bone tunneling device mechanically driven by one or more motors, it may include a connector for rapid connection and disconnection of the working portion of the circular bone tunneling device/suture passer (i.e. the head and the elongate body) from the shaft that contains the hollow tube and support mechanism controls.

Reference is now made again to FIG. 14, which illustrates an example of such a connector. The connector is hollow to allow physical connection of the control and driving mechanisms within the same, and comprises at least one pivotable joint 900. The pivotable joint 900 comprises a slot, a fixed acceptor 910 with a pin adapted to match the slot, and a slidable closure 920 that slides over the joint and pin after the connection is made (so as to fix the connection).

It should be understood to one skilled in the art that the design (e.g., cross section, length et cetera) and properties (e.g., mechanical properties; rigid or soft) of the surgical needle used is of critical importance in order to successfully enable the penetration of the needle into the bone.

As mentioned above, one of the needle's critical properties is the length of the needle used. If the needle used is too long, changing the direction of the penetration path by the hollow tube would be resisted and difficult to achieve.

Figure 66A:
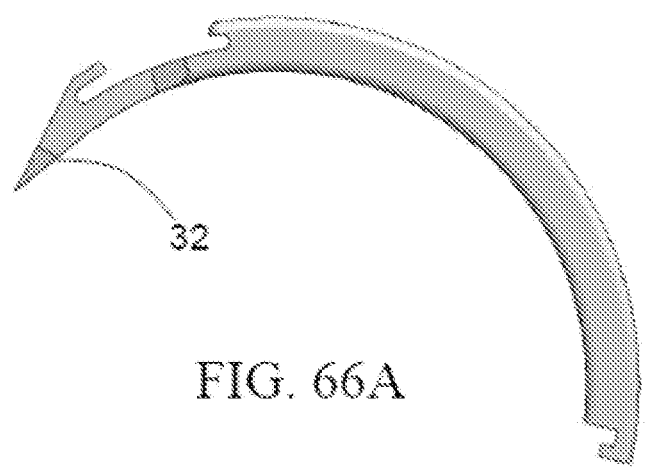
FIG. 66 illustrates a flat needle 32 used in some embodiments of the invention.
Figure 66B:
Figure 66C:
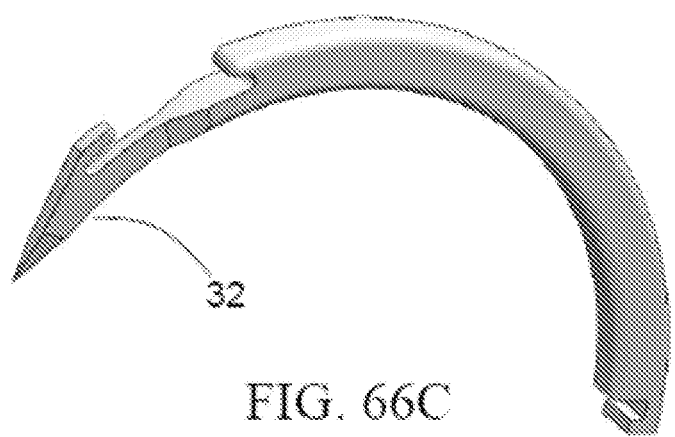

According to another embodiment, the needle is a straight needle or slightly curved needle. According to another embodiment of the present invention the cross sectional area of the needle is selected from a group consisting of circular, triangular, rectangular, flat, or any combination thereof. Reference is now made to FIG. 66, which presents three views (side, top, and isometric) of a flat needle 32 as used in some embodiments of the invention.

It should be understood to one skilled in the art that the design (e.g., cross section, length et cetera) and properties (e.g., mechanical properties; rigid or soft, materials from which the same is made) of the surgical rigid hollow tube used is of critical importance in order to successfully enable the penetration of the same into the bone.

Figure 17:
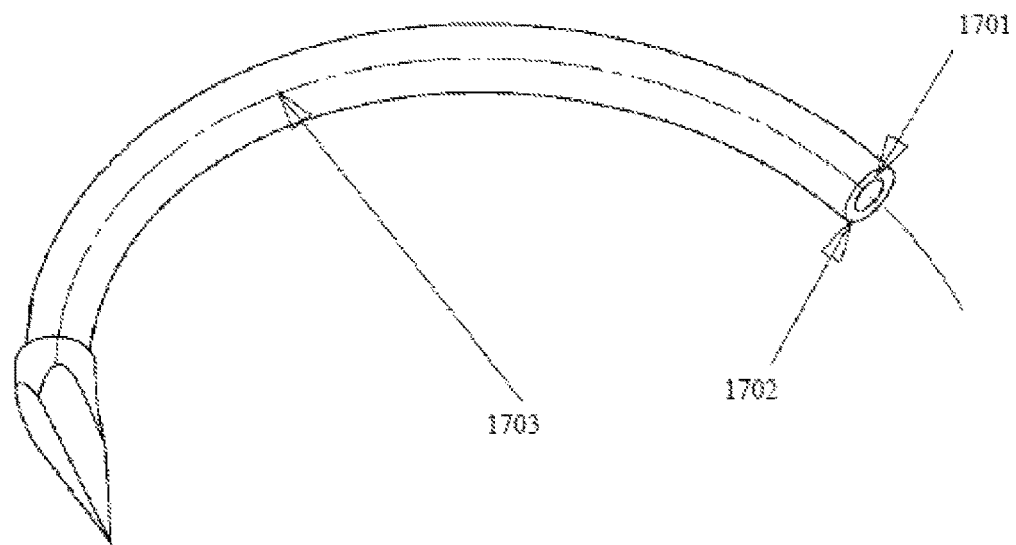
FIG. 17 schematically illustrates the dimensions of the hollow tubes.

According to one embodiment of the present invention, the hollow tube's outer diameter is in the range of about 1 to about 3 mm; According to another embodiment, the internal diameter (through which the guide wire passes) is in the range of about 0.5 to about 1.5 mm; or any combination thereof. Reference is now made to FIG. 17 illustrating both the internal diameter (illustrated as numerical reference 1701) of the hollow tube and the outer diameter (illustrated as numerical reference 1702) of the same. Also illustrated in the figure is the radius of curvature (illustrated as numerical reference 1703). According to one embodiment of the present invention the radius of curvature 1703 is in the range of about 7.5 mm to about 15 mm, especially 12.5 mm. According to another embodiment, the surgical rigid hollow tube is made of biocompatible metal selected from hardened corrosion resistant steel.

Figure 15A:
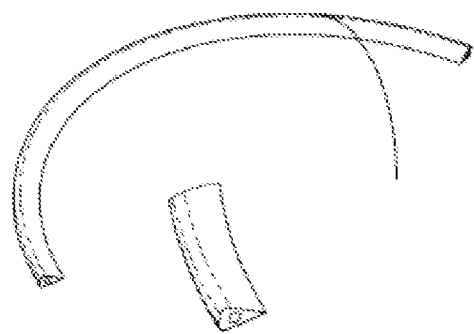
FIGS. 15a-15b presents a schematic view of an embodiment of the present invention, utilizing a hollow tube having a combination circular and triangular cross sectional area.

Reference is now made to FIG. 15a illustrating a hollow tube 34 having a triangular cross-section.

Figure 15B:
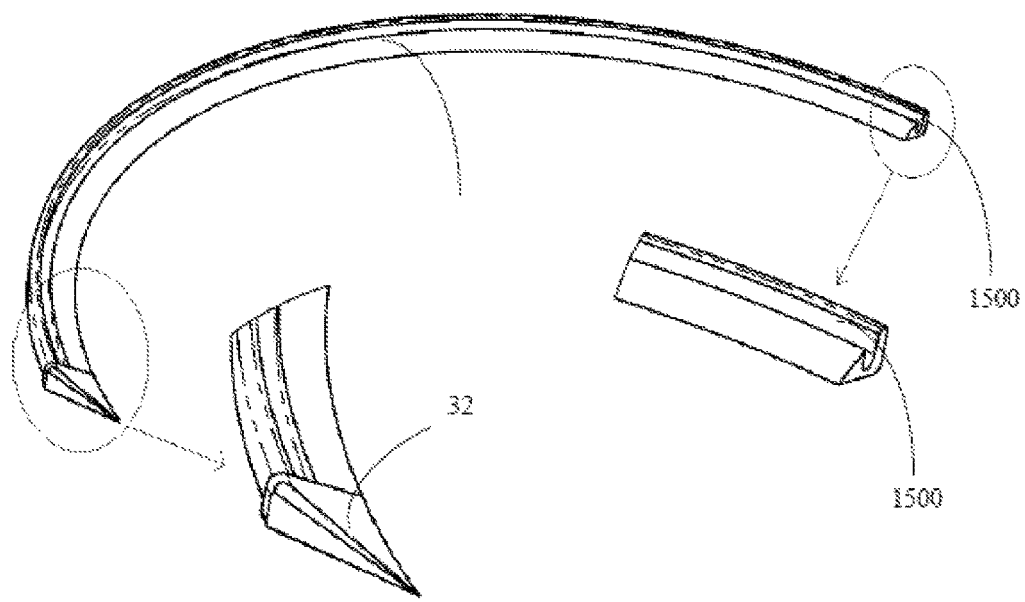

It should be pointed out that according to one embodiment of the present invention wire 130 is threaded through the hollow tube 34. According to another embodiment, the hollow tube 34 and the surgical needle comprises a groove along said needle's circumference (incase the cross section of said hollow tube is circular) or along at least one of said hollow tube's rib (in case the cross section is triangular or rectangular) throughout which said wire 130 is threaded. It should be understood to one skilled in the art, that the formation of a groove along one of the circumference or ribs simplifies the production line of the same. Reference is now made to FIG. 15b illustrating such an embodiment. According to this embodiment wire 130 is along groove 1500.

According to one embodiment of the present invention, one of the triangle's vertexes is pointing towards the center of the circular arc. Such an embodiment will ensure minimal resistance during the penetration into the bone.

Figure 16A:
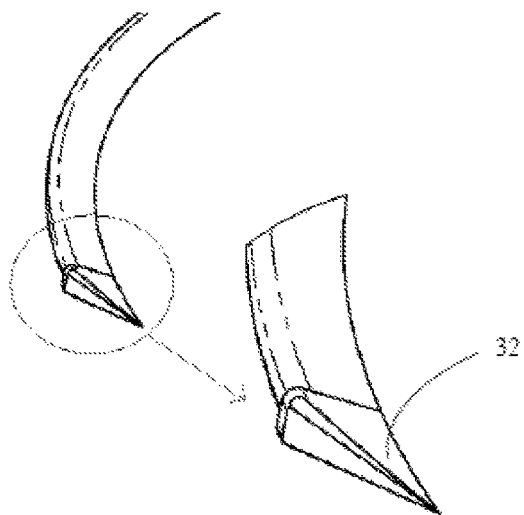
FIGS. 16a-16b illustrates another embodiment of the present invention, utilizing a slightly curved needle.
Figure 16B:
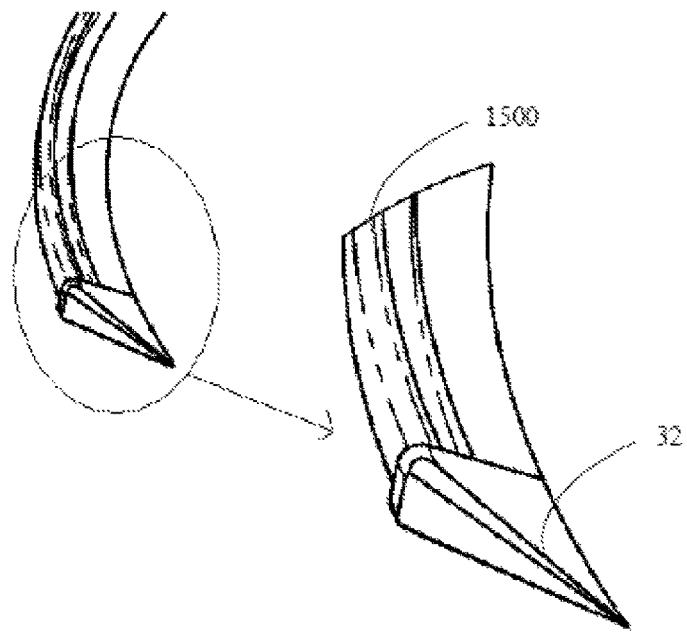

Reference is now made to FIGS. 16a-16b, illustrating another embodiment of the present invention in which the needle 32 being used is a slightly curved needle. Such curved needle ensures the mating and the slip fit between the needle, 32, and the support element 54 and further allows the needle and hollow tube to move in the direction of the arc.

FIG. 16b also illustrates an embodiment in which the hollow tube 34 comprises a grove 1500 along which said wire 130 is threaded.

It should be understood to one skilled in the art that the design (e.g., cross section, length et cetera) and properties (e.g., mechanical properties; rigid or soft, materials from which the same is made) of the surgical rigid hollow tube used is of critical.

Figure 18:
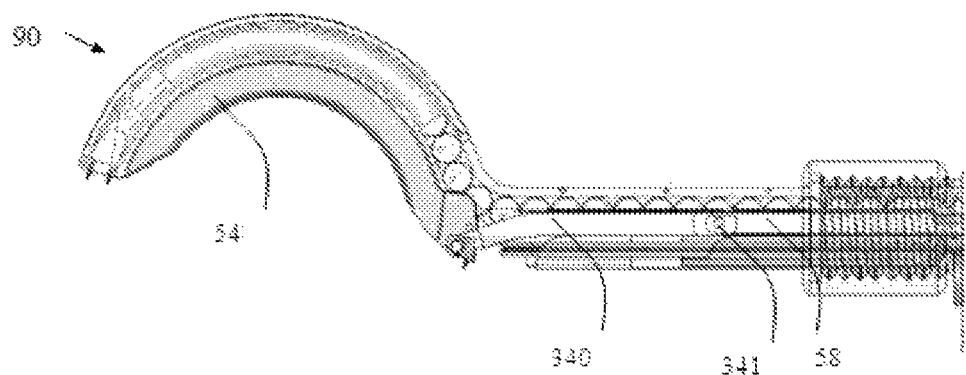
FIGS. 18-20 illustrate another embodiment of the extendable/retractable support element (54)
Figure 19:
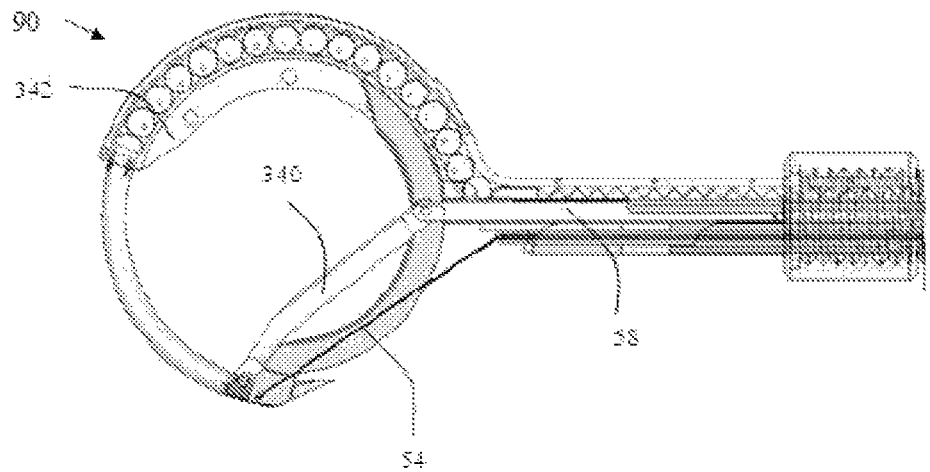
Figure 20:
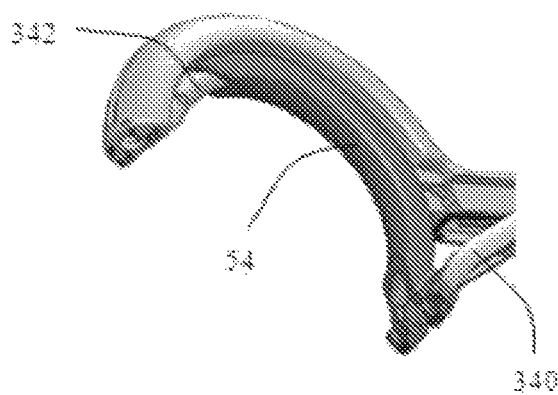

Reference is now made to FIGS. 18-20 which illustrate another embodiment of the extendable/retractable support element (54).

According to this embodiment, the support element (54) is movable along the rigid circular arc formed by the hollow elongate body.

In this embodiment, the support element driving mechanism comprises an actuator 58 that is pivotably connected substantially at its distal end to a yoke 340 via a pin 341. Yoke 340 is pivotably connected substantially at its distal end to the support element 54. When actuator 58 is engaged, the same travels distally, whereby yoke 340 moves downward, causing the support element 54 to extend downwardly along the rigid circular arc formed by the hollow elongate body.

Reference is now made to FIG. 19 which illustrates the support element 54 when the same is fully extended.

As can been seen from FIG. 19, actuator 58 has traveled its full path distally, thereby causing yoke 340 and support element 54 to fully extend downwardly.

According to this embodiment, an arch-like shaft 342 is coupled to the hollow elongate body head 90 from the underside of the same, such that when the support element 54 is activated, the same slides along the arch-like shaft 342.

Said slide of the support element 54 along said arch-like shaft 342 reconfigure the support element 54 from the retracted configuration to the extended configuration.

Reference is now made to FIG. 20, which, as in FIGS. 18-19, illustrates the new embodiment of the support element 54, when the same is partially extended. Also illustrated in said FIGS. is the Reference is now made to FIGS. 21-31 illustrating a second embodiment of the circular bone tunneling device/adjustable suture passer.

According to this embodiment, a suture cartridge 500 is provided. Said suture cartridge 500 loads a suture to the support element 54 such that when the needle 32 engages with the support element 54, the same 'catches' the suture.

It should be pointed out that the term "engagement of the needle with the support element" refers hereinafter to the entrance of the needle 32 into the support element 54 once the needle has emerged out of the bone after tunneling the arc-shaped path through the same.

It should be pointed out that the term "catches" refers hereinafter to any means (either by mechanical means, magnetically, electrical means or any combination thereof) adapted to capture or hold the suture. Specifically the term catches refers hereinafter means provided with/on the needle 32 adapted to catch the suture when the same engages with the support element.

Said circular bone tunneling device, unlike the previously disclosed embodiment, comprises a dedicated suture 32 (will be disclosed in FIGS. 21-22), a suture cartridge 500 (will be disclosed in FIGS. 23-26) and a loading mechanism for loading the suture 130 onto the support element 54 (will be disclosed in FIGS. 27a-27e).

Figure 21:
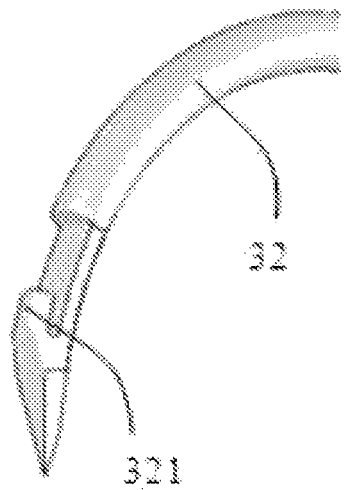
FIGS. 21-22 illustrate another embodiment of the needle 32.
Figure 22:
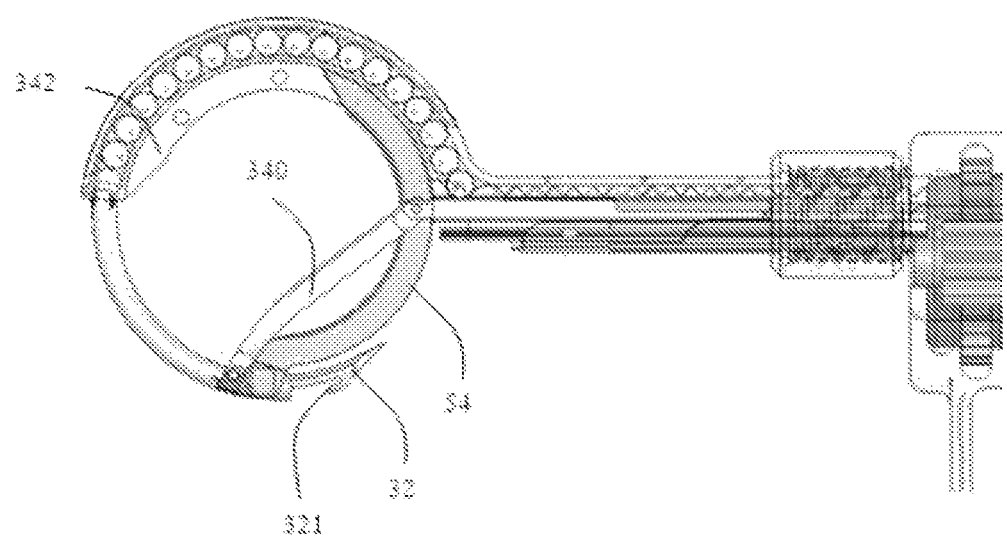
Figure 23:
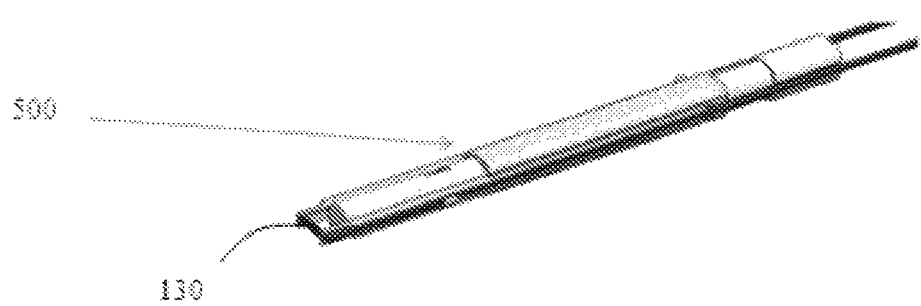
FIGS. 23-26 illustrate the suture cartridge 500.
Figure 24:
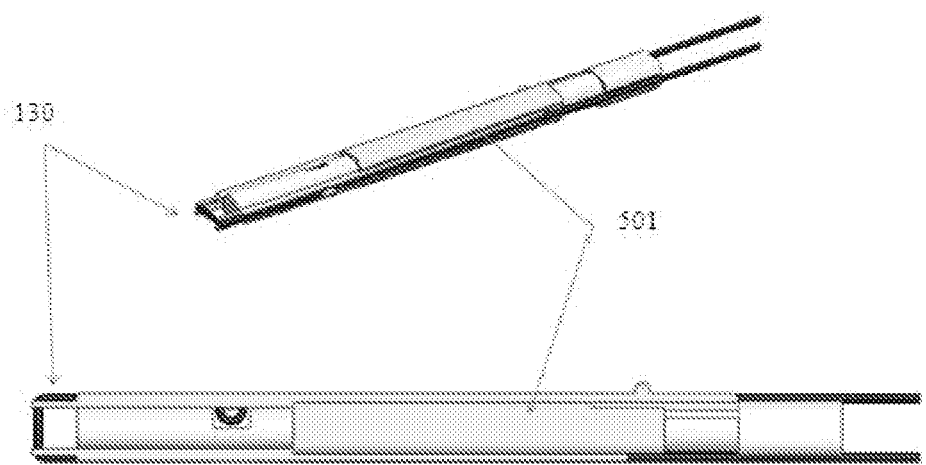

Reference is now made to FIGS. 21-22 which illustrate another embodiment of the needle 32.

According to this embodiment, needle 32 comprises at least one hook 321. Said hook's 321 role is in the engagement of the needle with the support member so as to catch the suture/wire 130 (will be disclosed hereinafter).

Reference is now made to FIG. 22 illustrating the fully extended support member 54 and needle 32 engaging with the same (i.e., the needle is fully inserted into said support member 54). In this stage, the hook 321 will catch the suture.

Reference is now made to FIGS. 23-26 illustrating the suture cartridge 500.

Suture cartridge 500 is coupled to shaft 50 of the circular bone tunneling device (see FIG. 26), and is adapted to reciprocally move along the longitudinal axis of the same so as to load the suture 130 onto the support element 54 (as will be disclosed hereinafter).

Figure 25:
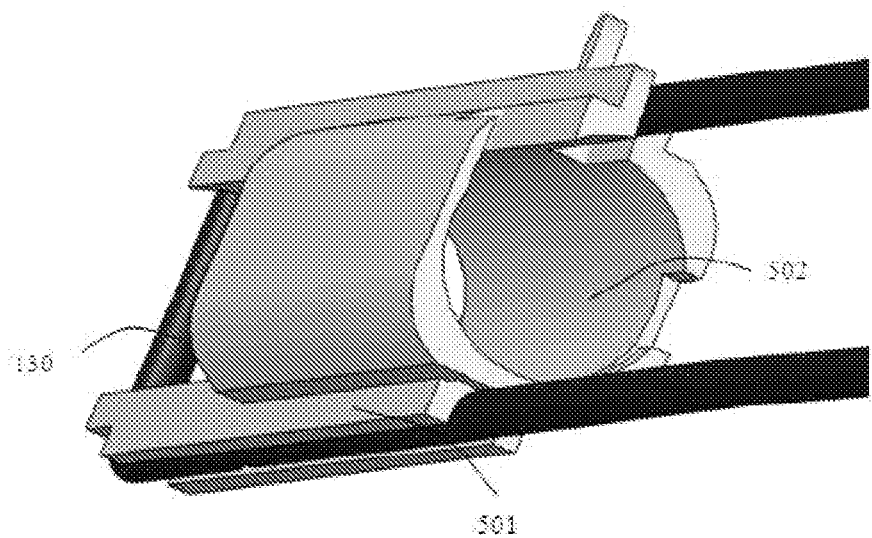
Figure 26:
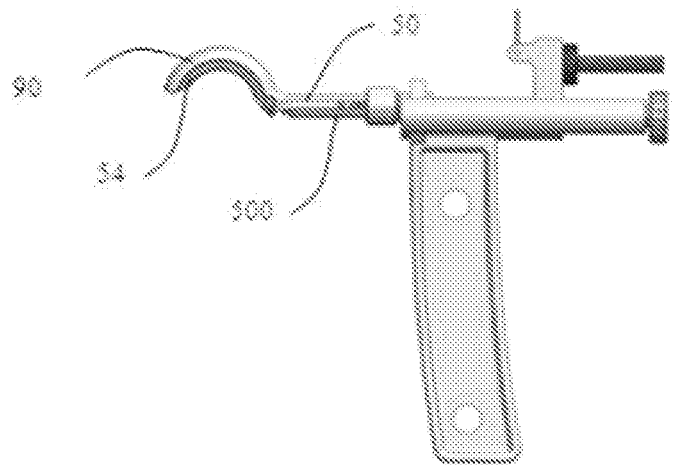

The cartridge 500 is characterized by having an external scaffold 501 enclosing an inner body 502 (see FIG. 25). Said inner body plays an important role and enables the insertion of a working tool throughout the same (as will be disclosed hereinafter).

According to this embodiment, suture 130 is disposed along the outer circumference of scaffold 501 of cartridge 500.

Reference is now made to FIGS. 27a-27e illustrating the loading mechanism 600 for loading suture 130 onto the support element 54.

The loading mechanism 600 comprising at least one (preferably two) hooks 603 pivotably connected to the support element 54.

In order to load suture 130 to the supporting element 54, suture cartridge 500 is linearly moved forward towards the supporting element 54 (see FIG. 27a), until suture 130 reaches hooks 603.

Figure 27A:
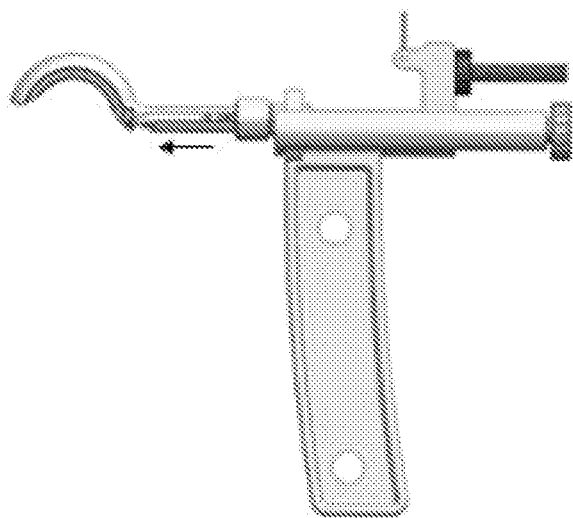
FIGS. 27a-27e illustrate the loading mechanism 600 for loading suture 130 onto the support element 54.
Figure 27B:
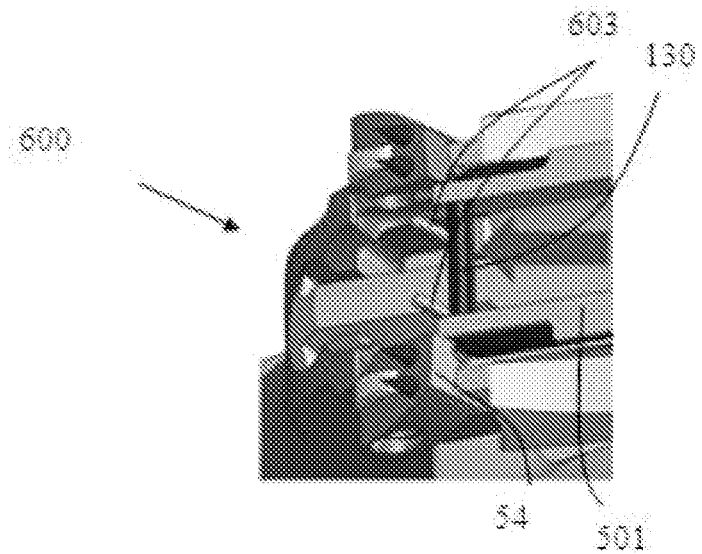
Figure 27C:
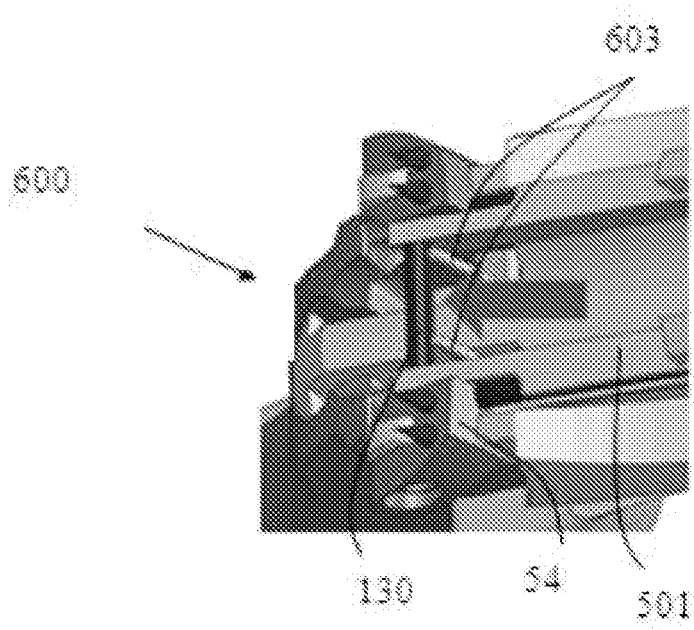
Figure 27D:
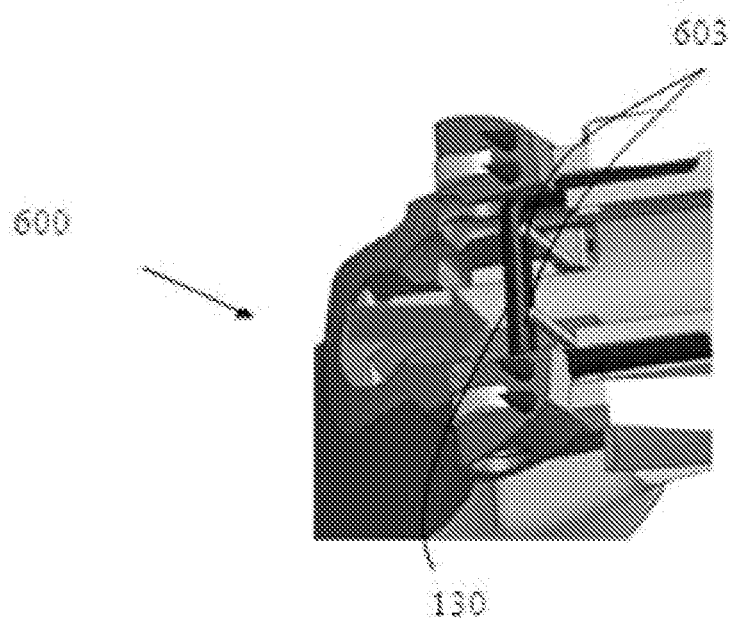
Figure 27E:
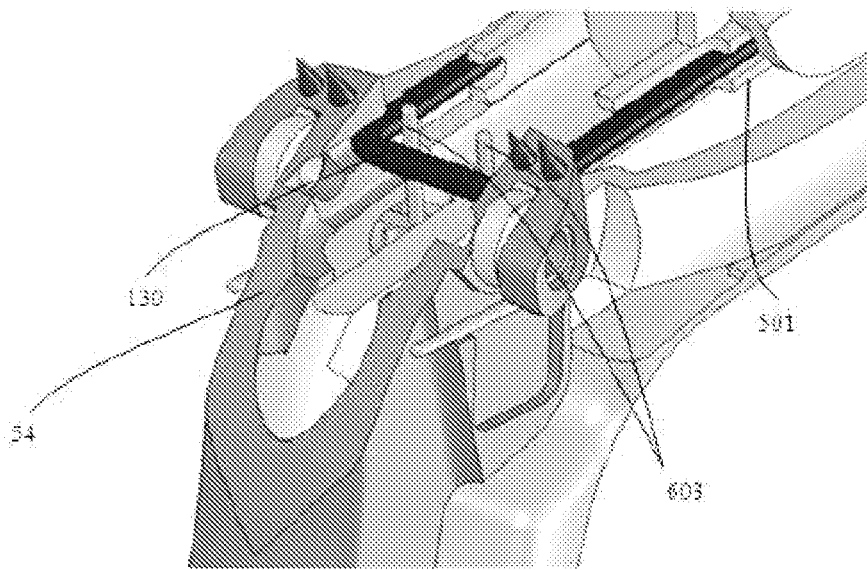

FIGS. 27b-27d provides a closer view of the suture loading mechanism.

First, the suture cartridge 500 is pushed forwards (see FIG. 27b) until suture 130 reaches hooks 603 of the support element 54 (see FIG. 27c).

Next, the suture is passed over hooks 603 such that the hooks hold suture 130 (see FIGS. 27d-27e) and prevent its release. Said suture being held by hooks 603 will be later engaged with the needle 32 (more specifically with hook 321 of the needle).

Reference is now made to FIGS. 28-31 which illustrates the engagement of the needle 32 with the support element 54 and the suture cartridge 500 (after the suture 130 has been loaded).

Figure 28:
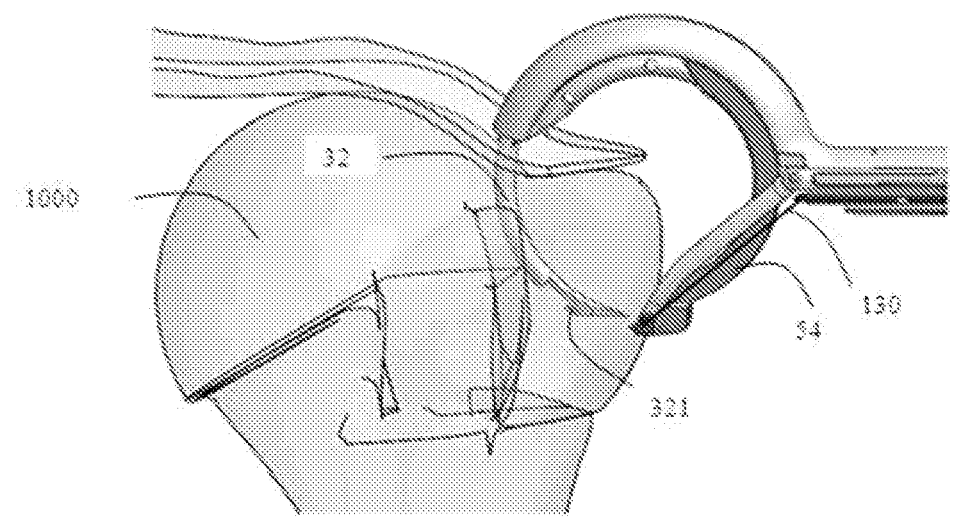
FIG. 28 illustrates the circular bone tunneling device once the suture 130 has been loaded to the support element 54 and the needle has already penetrated into the bone 1000.

FIG. 28 illustrates the circular bone tunneling device once the suture 130 has been loaded to the support element 54 and the needle has already penetrated into the bone 1000 and tunneled through the same.

Figure 29:
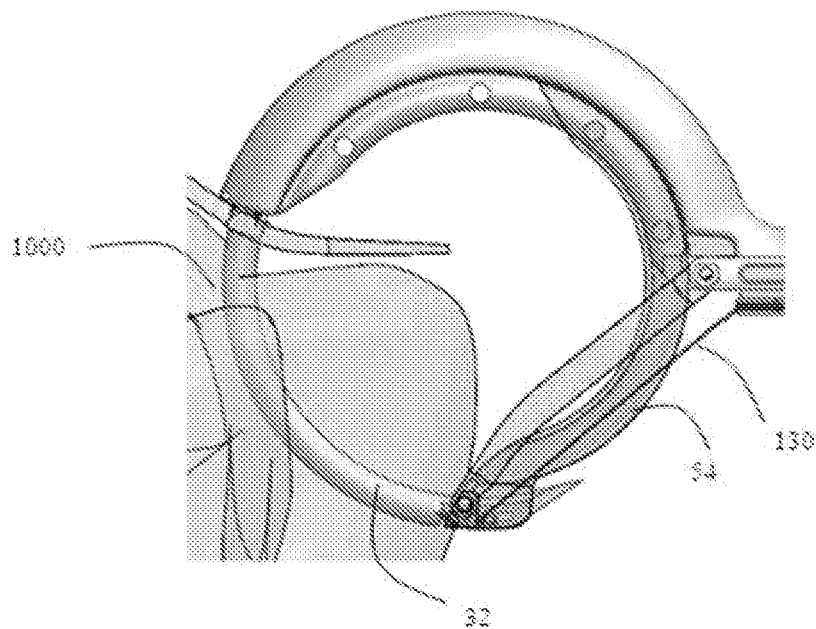
FIGS. 29-31 illustrate needle 32 engaging with the support element 54.

FIG. 29 illustrates needle 32 engaging with the support element 54. The main objective of said engagement is to 'catch' suture 130. Said catching is provided by means of hook 321.

Once said hook 321 reaches suture 130 being held by hooks 603 of the supporting element 54, the same encases suture 130.

Figure 30:
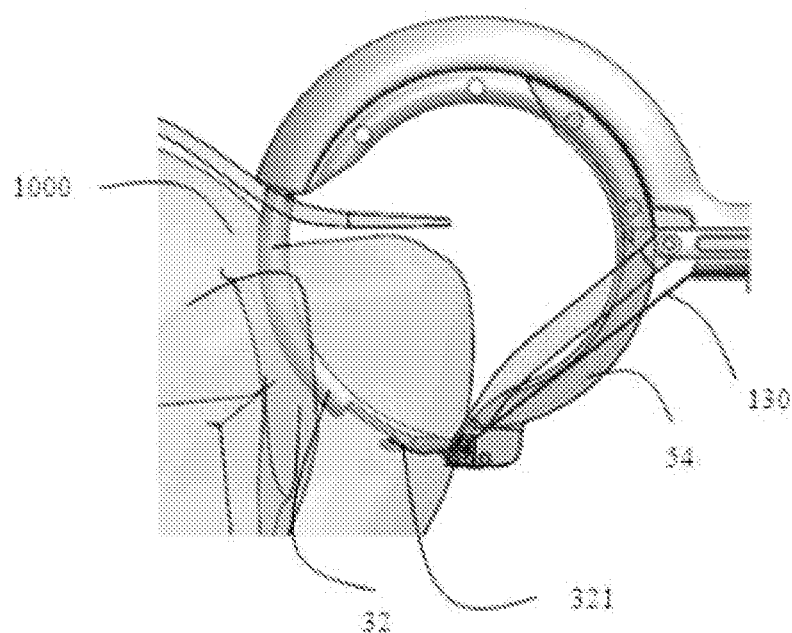
Figure 31:
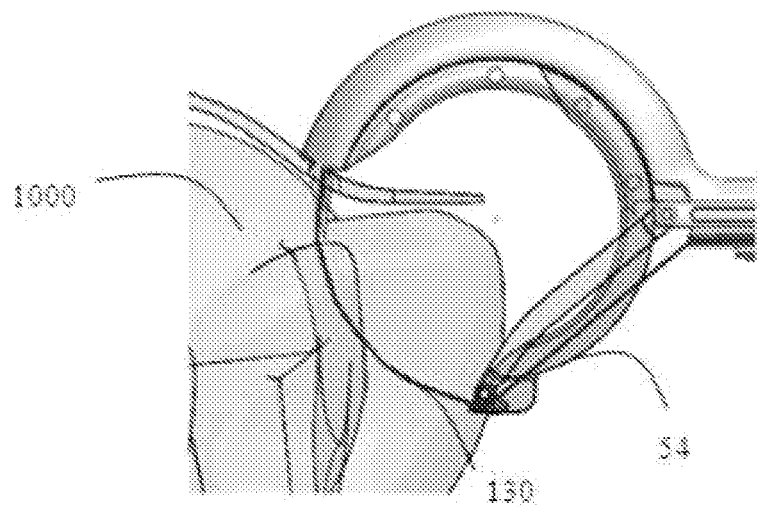

Once said hook 321 catches suture 130 needle 32 can be retracted back through bone 1000 (along the circular path created/tunneled by said needle 32 when the same penetrated said bone 1000), see FIGS. 30-31.

According to another embodiment of the present invention the catching of the suture is provided by at least one selected from a group consisting of electrical means, magnetic means or any combination thereof being provided along/within/with said needle 32.

Furthermore, it should be understood that the hook 321 disclosed above provided along said needle is given as a mere example of mechanical means capturing the suture. Other embodiments as known in the art can be applied as well.

According to another embodiment of the present invention, a working tool is provided along a working channel within the circular bone tunneling device.

According to one embodiment the inner body 502 of suture cartridge 500 is utilized as the working channel.

As mentioned above, the suture cartridge comprises an inner body 502. Said inner body 502 is structured to have a diameter of approximately 3 mm such that any surgical tool having a diameter of 3 mm or less could be inserted through the same. Such tool could be e.g., grasper, tendon holder, scissors, diathermy means, scalpel, stapler, jig, suturing means and any combination thereof.

According to another embodiment of the present invention the working tool (e.g., grasper) can be passed through the shaft 50 of the circular bone tunneling device.

Figure 32:
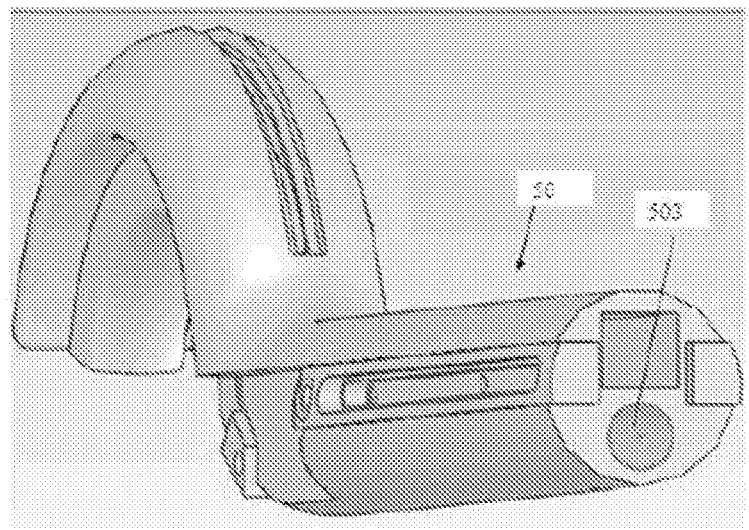
FIGS. 32-33 illustrate a working channel 503 being created through either shaft 50 (FIG. 32) and/or through the inner body 502 of cartridge 500 (FIG. 33)
Figure 33:
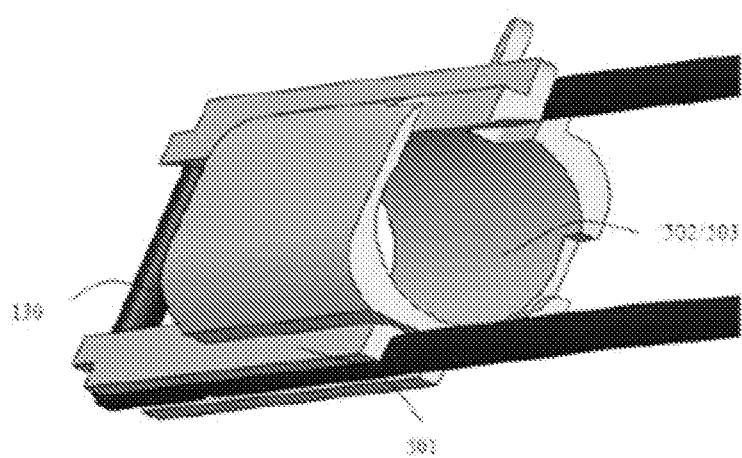
Figure 34:
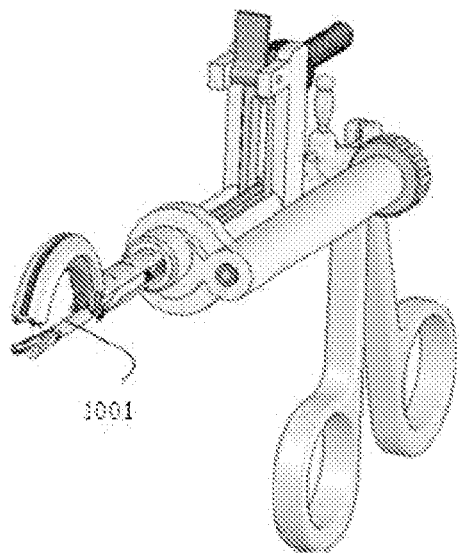
FIG. 34 illustrates the incorporation of a working tool (e.g., grasper) 1001 into the circular bone tunneling device.

Reference is now made to FIGS. 32-34 illustrating such an embodiment. According to said embodiment, shaft 50 is structured to have an inner elongated hollow tube (will be referred hereinafter as a working channel) 503 running throughout shaft 50 (see FIG. 32).

According to another embodiment the inner body 502 of cartridge 500 is utilized as the working channel (see FIG. 33).

FIG. 34 illustrates the incorporation of a working tool (e.g., grasper) 1001 into the circular bone tunneling device.

Reference is now made to FIGS. 35-49 illustrating the overall method of utilizing the circular bone tunneling device.

Figure 35:
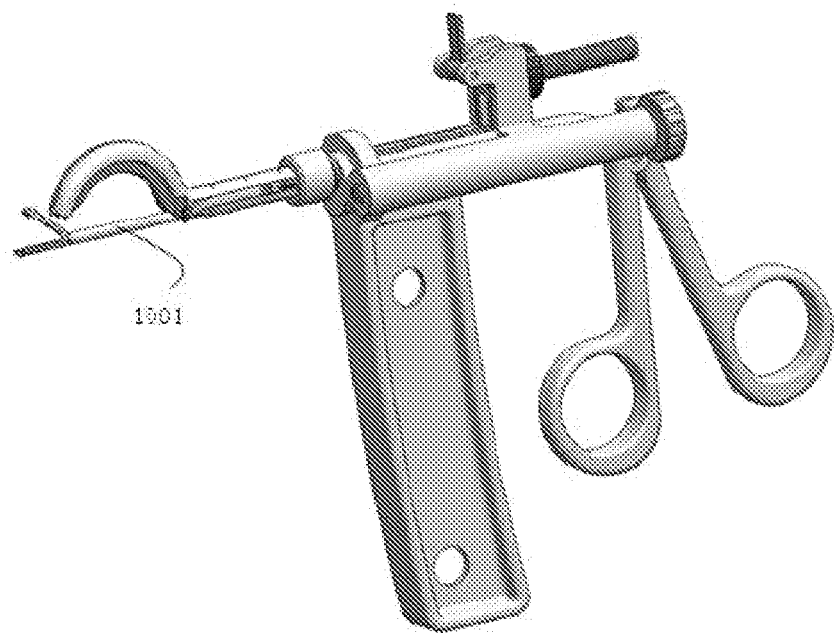
FIGS. 35-49 illustrate the overall method of utilizing the circular bone tunneling device.

FIG. 35 illustrates the grasper being inserted through the working channel 503 of the circular bone tunneling device (e.g., through the internal body 502 of the cartridge 500).

Figure 36:
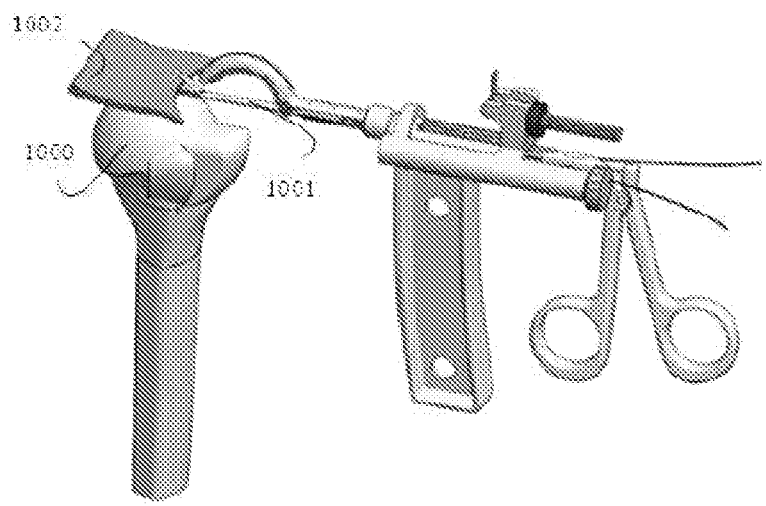

FIG. 36 illustrates the grasping of the tendon 1002 by means of the grasper 1001.

Figure 37:
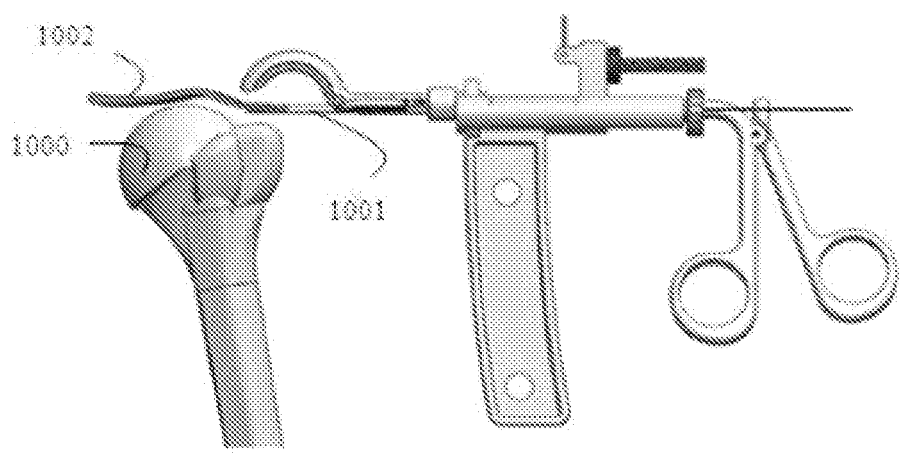
Figure 38:
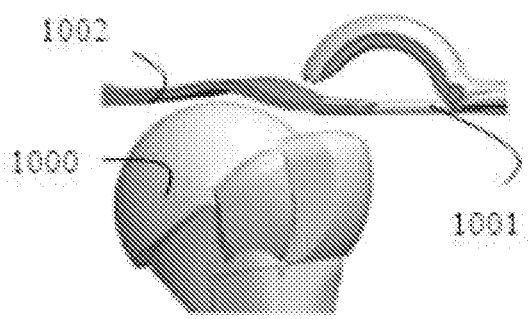
Figure 39:
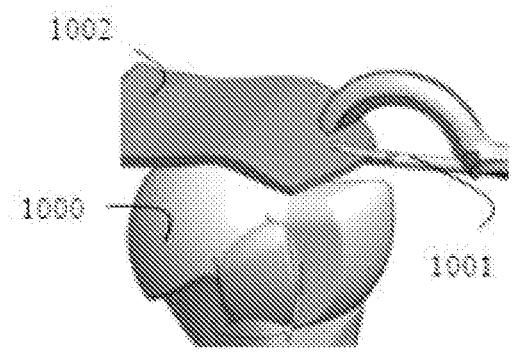

FIG. 37 illustrates grasper 1001 pulling the tendon 1002 to a position at which the needle 32 will penetrate. FIGS. 38-39 illustrate a closer view of the same.

Figure 40:
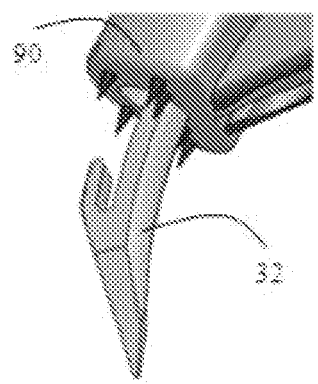

FIG. 40 provides a closer view of the needle being extracted from the circular bone tunneling device (namely from the hollow elongate body head 90.

Figure 41:
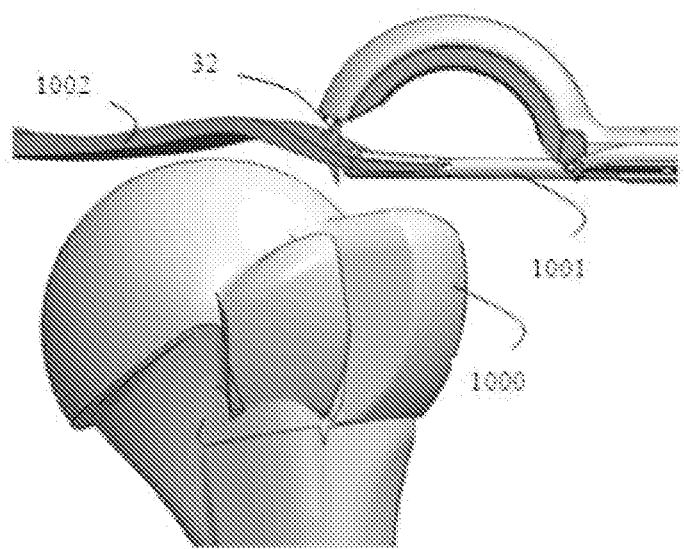

FIG. 41 illustrates the needle 32 being passed through the tendon 1002.

Figure 42:
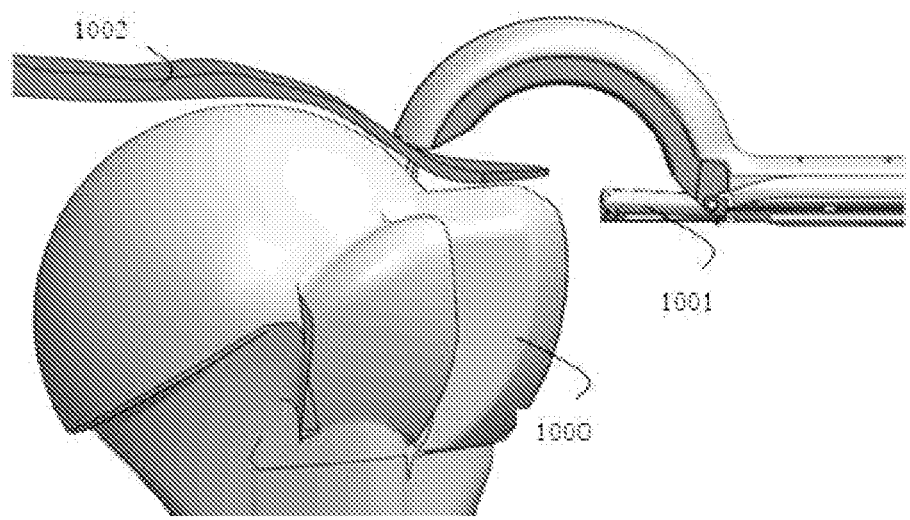

FIG. 42 illustrates the grasper 1001 being removed and extracted from the circular bone tunneling device.

Figure 43:
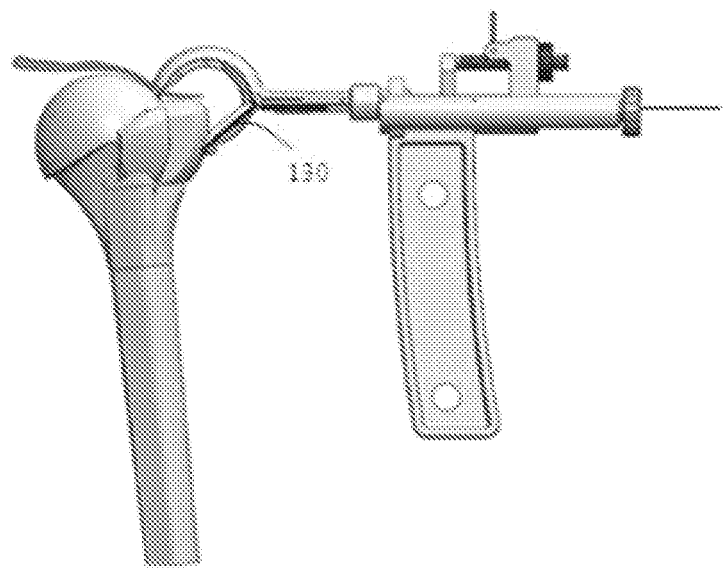
Figure 44:
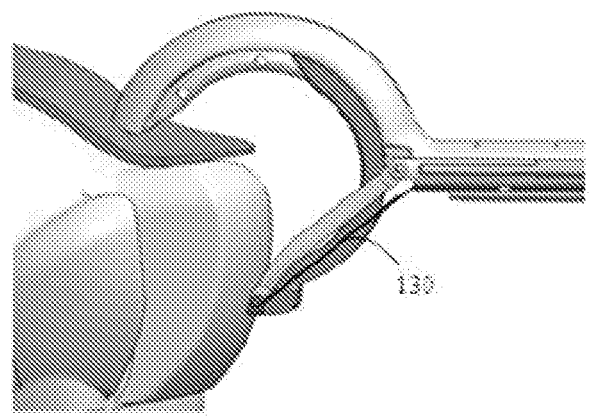

FIG. 43 illustrated the support element 54 being fully extended (after the suture 130 has been loaded, not shown). FIG. 44 provides a closer view of the same.

Figure 45:
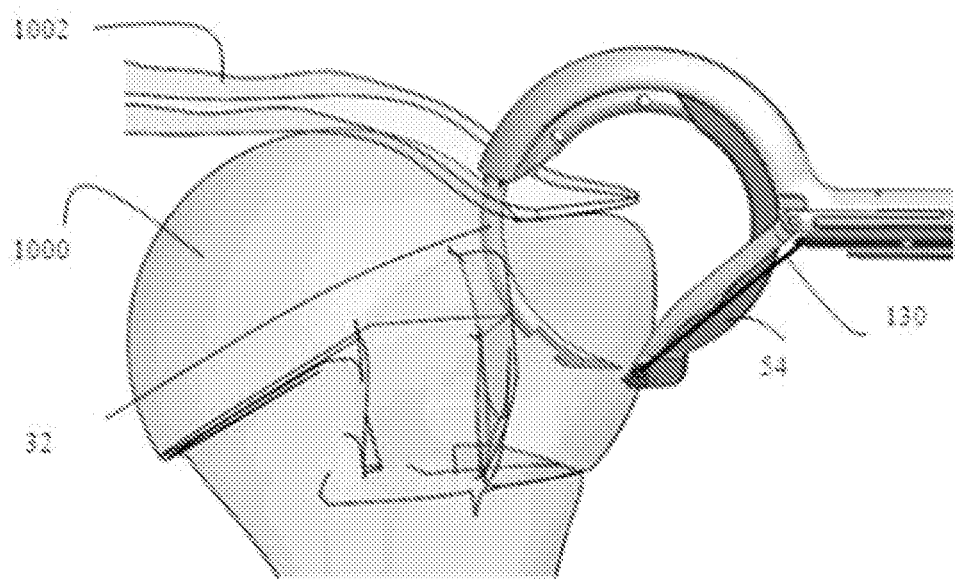

FIG. 45 illustrates the needle 32 being pushed forward through the bone 1000 so as to create said curved tunnel through the same.

Figure 46:
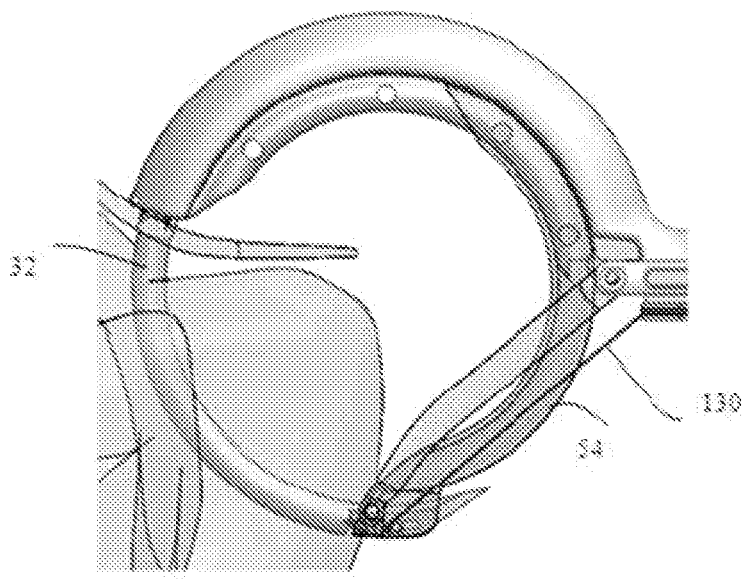

FIG. 46 illustrates the engagement of needle 32 with the supporting element 54. As described above, hook 321 of needle 32 engages with hooks 603 of support member 54 and encase suture 130.

Figure 47:
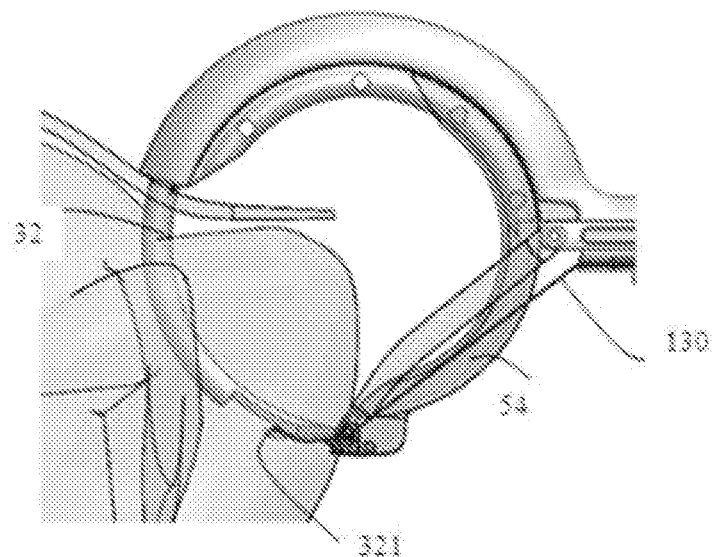

FIG. 47 illustrates needle 32 being retracted (moved back) through the curved channel with suture 130 caught onto hook 321.

Figure 48:
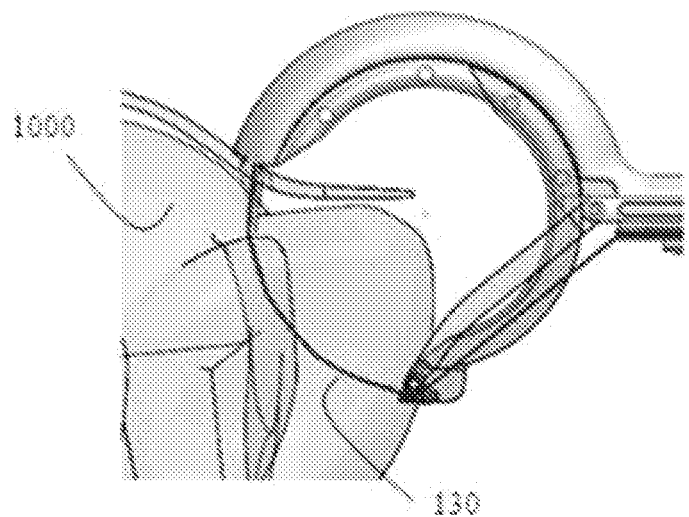

FIG. 48 illustrates the needle 32 being fully extracted from bone 1000.

Figure 49:
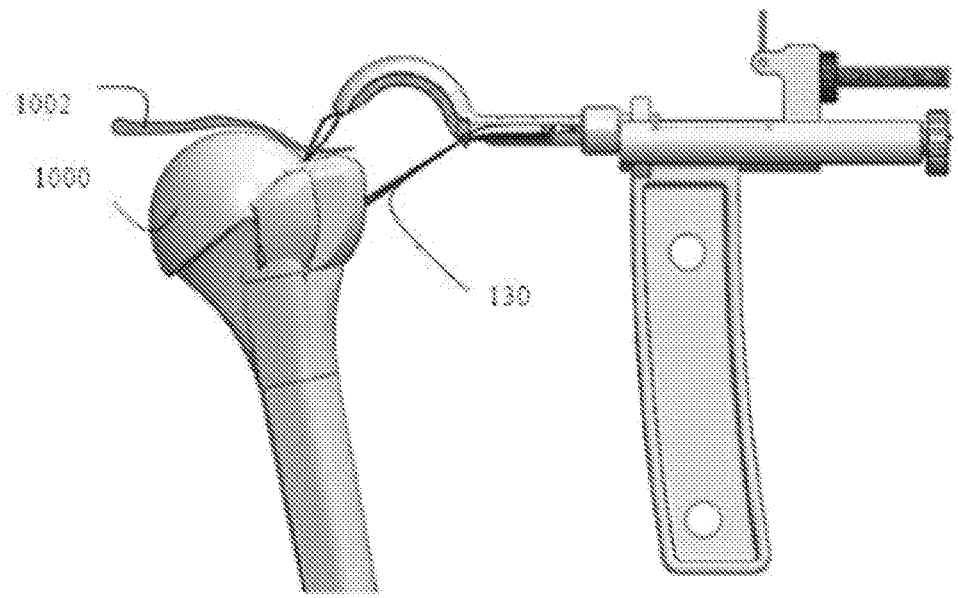

FIG. 49 illustrates the needle 32 and the supporting element 54 being retracted back to the circular bone tunneling device and wire 130 is completely passed through the bone 1000 and tendon or ligament 1002.

Figure 68A:
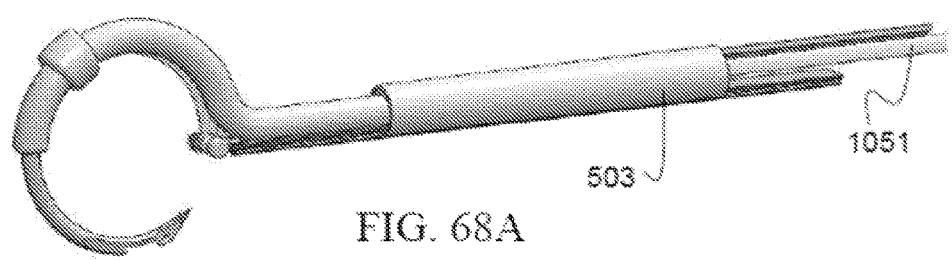
FIG. 68 illustrates an embodiment of the invention that incorporates a jig used to indicate the location of needle 32; and, FIG. 69 illustrates an embodiment of the invention that includes indicators showing the locations of support element 54 and needle 32.
Figure 68B:
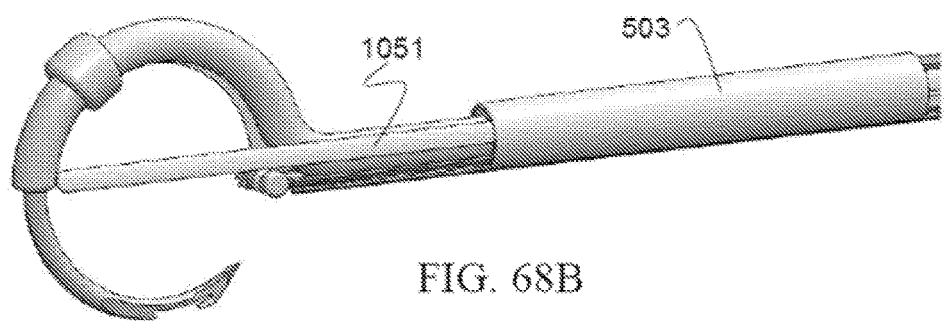
Figure 68C:
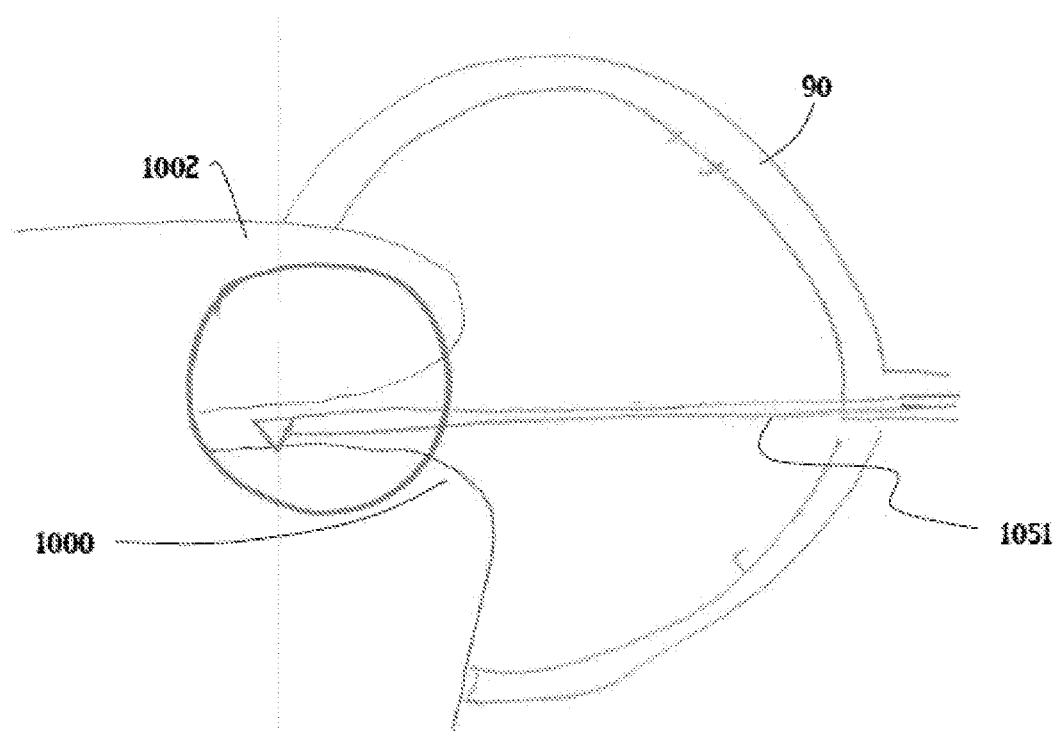

In arthroscopic procedures performed using instruments known in the art, the field of view of the camera is generally quite limited, and the surgeon sees on the screen a magnified view of a small area, normally the uppermost proximal area of the tendon or ligament. The surgeon does not have a wider view and cannot, for example, see in a single view the operating instrument and the upper portion of the hollow tube or the bone. Reference is now made to FIG. 68, which illustrates an embodiment of the invention in which it incorporates a jig to aid the surgeon in locating the needle and/or the expected pathway of the needle through the bone. FIG. 68A illustrates the distal portion of the instrument with jig 1051 retracted, while FIG. 68B illustrates the same portion of the instrument with the jig extended. FIG. 68C illustrates the use of the jig. The maximum distance to which the jig can be extended (circled in the figure) provides the surgeon with the information necessary to understand where the end of the instrument is located, where exactly the needle has entered tendon 1002 and bone 1000, and the overall orientation of the instrument.

Figure 68D:
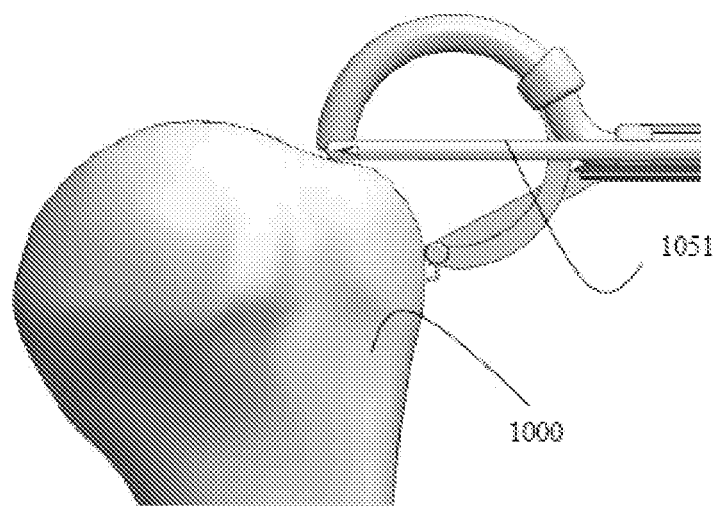
Figure 68E:
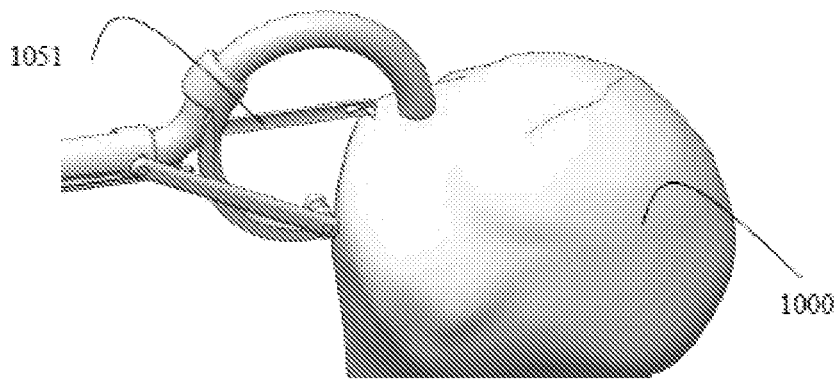
Figure 68F:
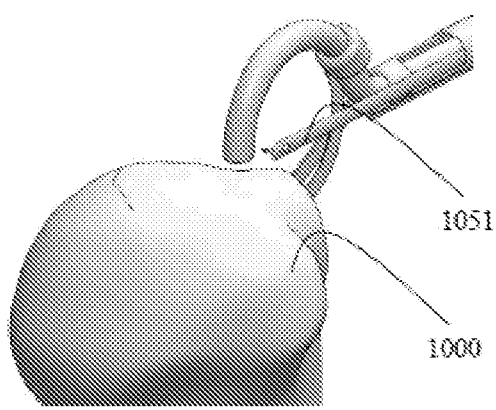

FIGS. 68D-68F provides a more clear illustration of jig 1051 with reference to tendon 1002 and bone 1000.

Figure 50:
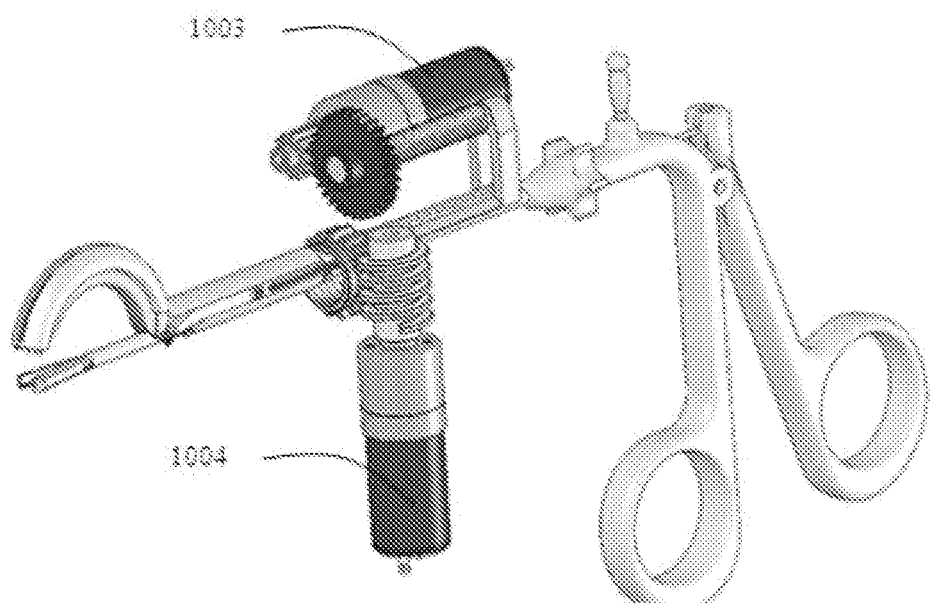
FIGS. 50-51 illustrate the circular bone tunneling device either manually operated (FIG. 50) or automatically operated (FIG. 51)
Figure 51:
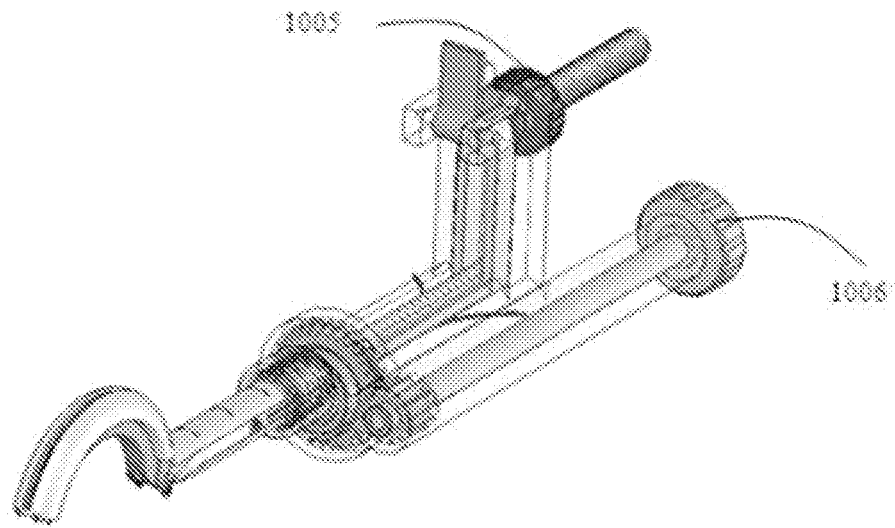

Reference is now made to FIGS. 50-51 illustrating the circular bone tunneling device as described above either manually operated (FIG. 50) or automatically operated (FIG. 51).

According to the motorized embodiment, one motor 1003 is in charge of the movement of the needle and the other 1004 in charge of the supporting element (see FIG. 50)

According to the manual embodiment, one rotating knob 1005 is in charge of the movement of the needle and the other 1006 in charge of the supporting element (see FIG. 51).

Figure 52:
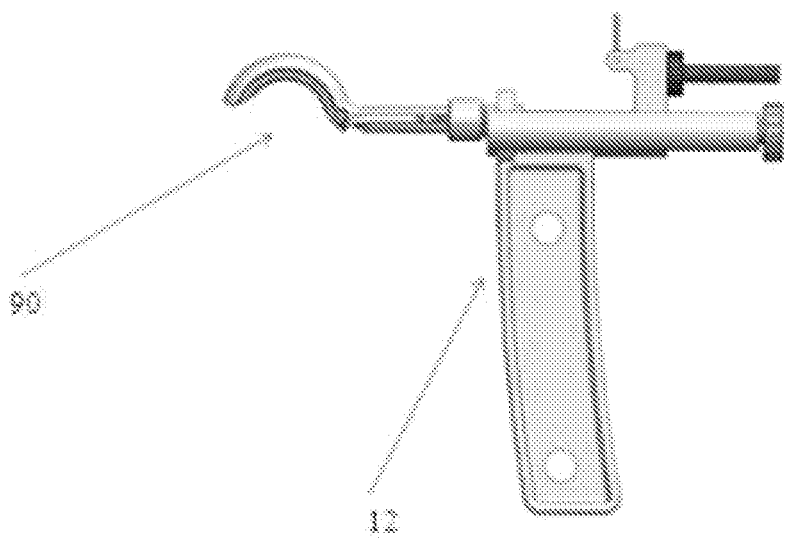
FIG. 52 illustrates another embodiment of the present invention in which at least a part of the same is disposable and a least a part of which is reusable.

According to yet another embodiment of the present invention the circular bone tunneling device comprises a disposable part and reusable part. According to this embodiment, the hollow elongate body head 90, is a disposable part to be used once and the handle 12 is a reusable part (see FIG. 52).

Figure 53:
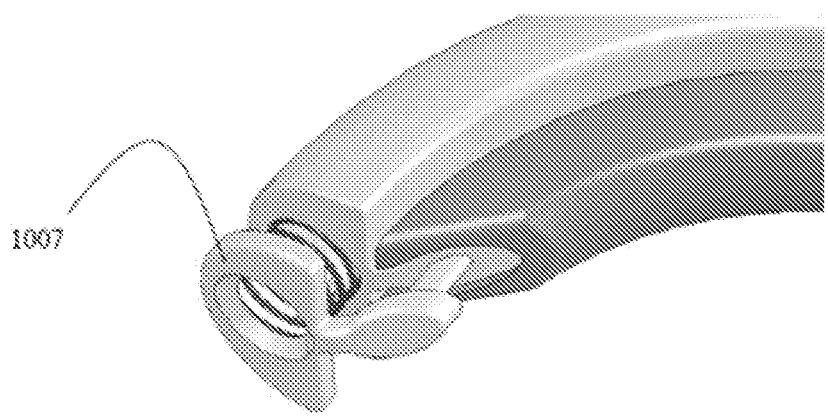
FIGS. 53-54 illustrate another embodiment of the present invention in which a retractable sleeve 1007 is provided.
Figure 54:
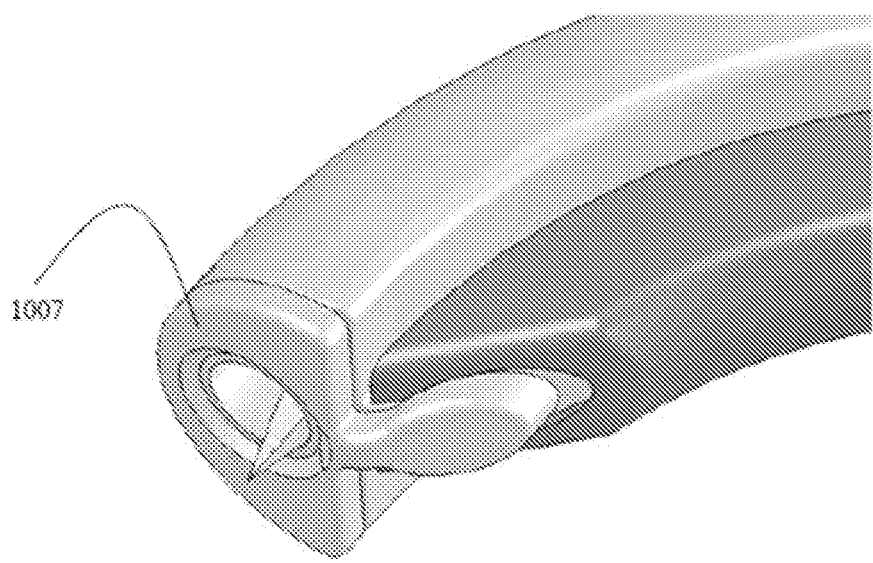

Reference is now made to FIGS. 53-54 illustrating another embodiment of the present invention in which a retractable sleeve 1007 is provided.

According to this embodiment said retractable sleeve 1007 is characterized by having at least two positions: (a) an extended position (see FIG. 53), in which said sleeve 1007 completely encircles needle 32; and, (b) retracted position (see FIG. 54), in which said needle 32 partially protrudes out of said retractable sleeve 1007.

The main objective of the use of sleeve 1007 is in the piercing of the tendon. According to this embodiment, the piercing of the tendon is obtained merely by approximating and adjacently bringing the low elongate body head 90 to the tendon while the sleeve is in the extended position and then retracting the sleeve so as to expose the needle and to pierce the tendon.

According to one embodiment of the present invention sleeve 1007 is characterized by a spring-like mechanical properties; such that, the actuation of said sleeve 1005 is provided by the compression/stretching of said spring.

Reference is now made to FIGS. 55-64 which illustrate another embodiment of the present invention in which anchoring means 1009 is being used. Said anchoring means 1009 is adapted to securely fix the tendon to the bone.

Figure 55:
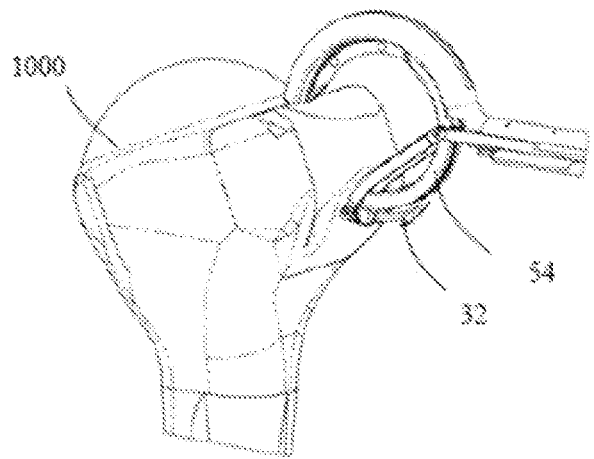
FIGS. 55-64 illustrate another embodiment of the present invention in which anchoring means 1009 is being used.
Figure 56:
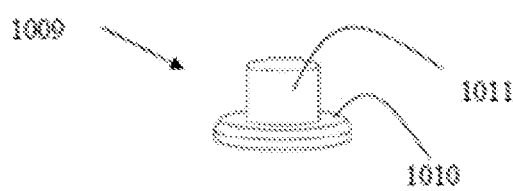

FIG. 55 illustrates the needle 32 after the same has tunneled through bone 1000. At this stage, according to previously disclosed embodiments, the needle is adapted to engage with the support member 54 so as to catch the suture 130. According to this embodiment, the needle 32 engages with anchor 1009, as will be described hereinafter.

Reference is now being made to FIGS. 56-59 which illustrate two exemplary embodiments of the anchor 1009.

According to one embodiment of the present invention, the anchor comprises at least one portion 1010 being characterized by cross section and/or diameter and/or dimensions substantially greater than the piercing aperture created in the bone 1000 and the tendon 1002 by needle 32. Portion's 1010 main rule is to fixate the anchor 1009 to its position and to prevent any movement of the same.

Anchor 1009 additionally comprises at least one second portion 1011 to which, according to one embodiment, said suture 130 is coupled.

Figure 57:
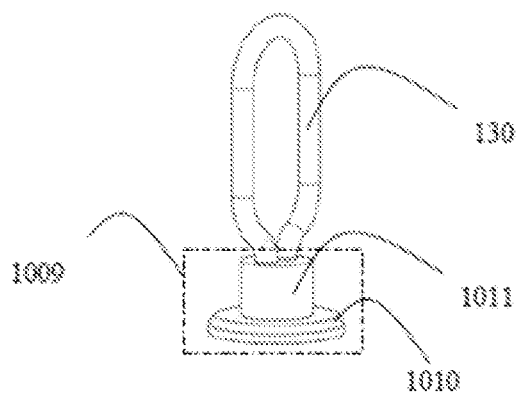

Reference is now being made to FIG. 57 which illustrates the anchor 1009 and the suture 130 coupled to the same (namely, to second portion 1011).

Figure 58:
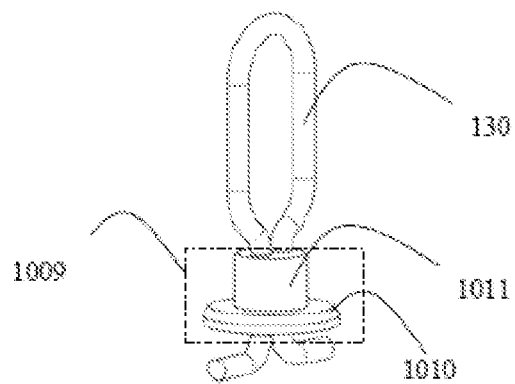

Reference is now being made to FIG. 58 which illustrates another embodiment of the present invention in which suture 130 is threaded through anchor 1009.

According to this embodiment, suture 130 is threaded through second portion 1011 (and 1010) and then the two ends of the same are folded and abutted against 1010 so as to secure the suture 130 against anchor 1009.

Figure 59:
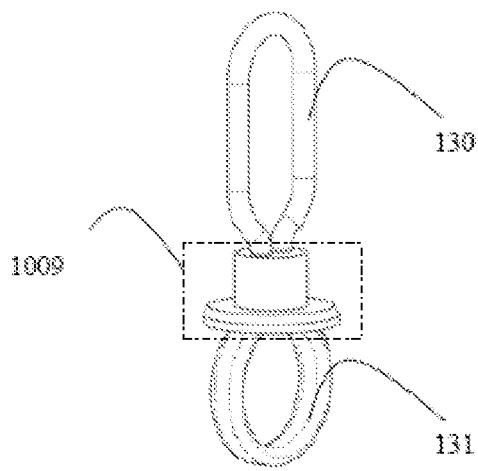

Reference is now being made to FIG. 59 which illustrates another embodiment of the present invention in which, in addition to suture 130, a second suture 131 is coupled to anchor 1009.

According to a preferred embodiment of the present invention suture 131 is coupled at its two ends to anchor 1009 so as to form a closed loop. Such a loop can be used to interleave additional sutures through the same.

Figure 60:
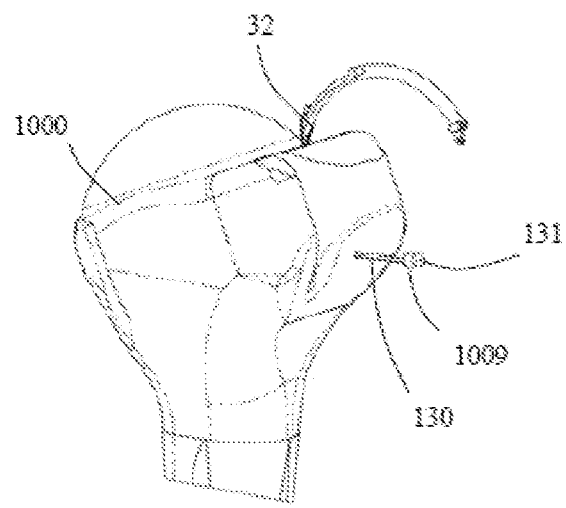
Figure 61:
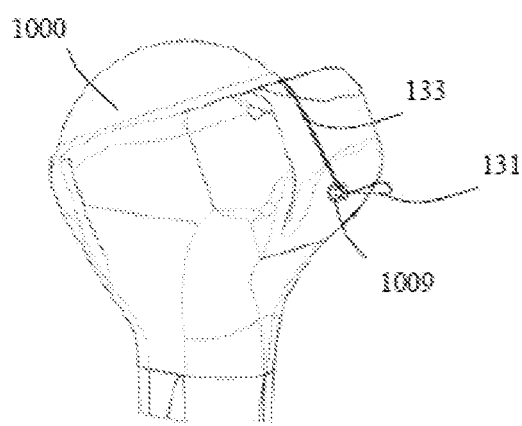

Reference is now being made to FIGS. 60-61 illustrating the incorporation of such anchor together with the circular bone tunneling device as described above.

FIG. 60 illustrates needle 32 when the same has already engaged with anchor 1009 and captured suture 130. In the FIG. needle 32 is being retracted out of bone 1000 thereby pulling suture 130 and anchor 1009.

FIG. 61 illustrates anchor 1009, when the same has been abutted against bone 1000.

FIG. 61 also illustrates interleaving a third suture 133 through the loop formed by the second suture 131.

Figure 62:
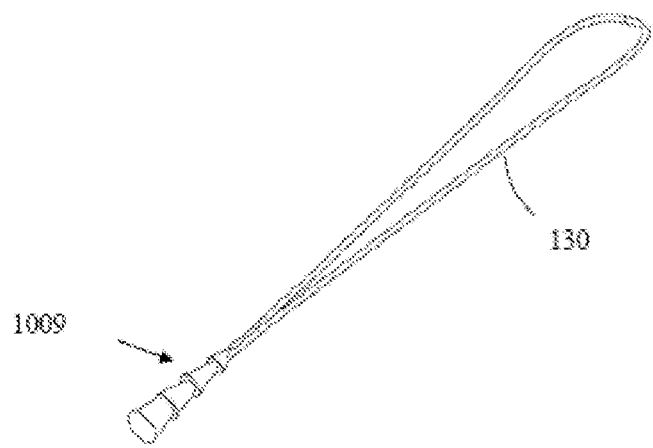
Figure 63:
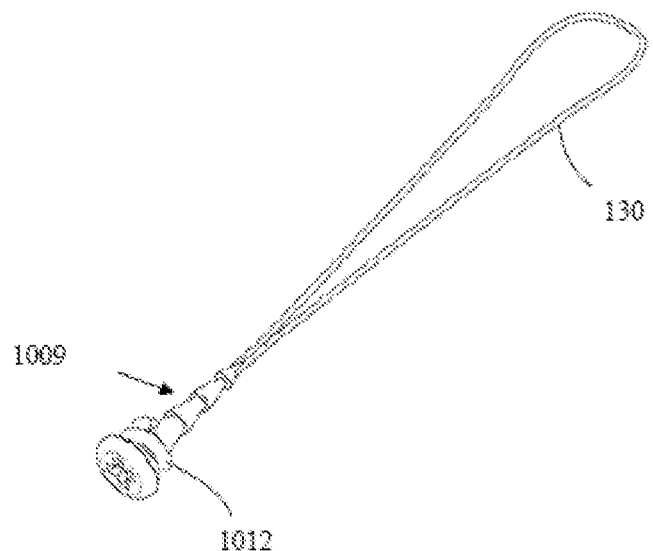
Figure 64:
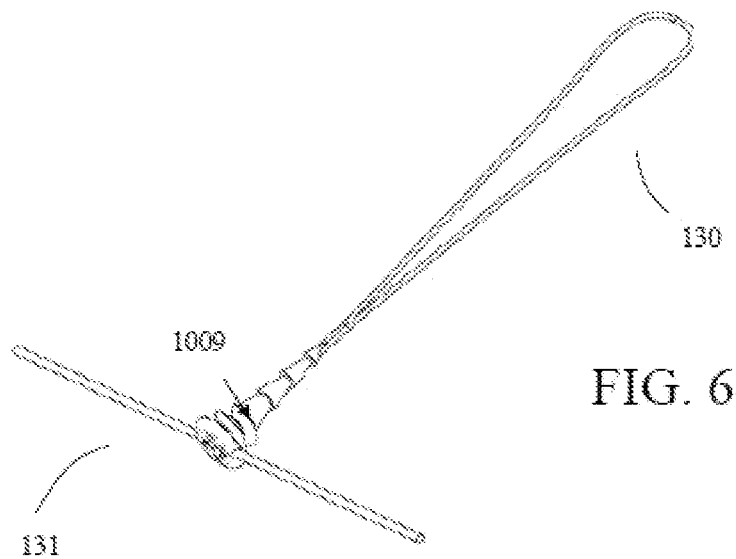

Reference is now being made to FIGS. 62-64 which illustrate another exemplary embodiment of the anchor 1009.

According to this embodiment, the anchor is shaped as a screw anchor or a wall plug.

According to another embodiment, anchor 1009 is provided with a screw 1012 so as to provide better fixation to the bone (see FIG. 63).

According to another embodiment, anchor 1009 is provided with a second suture 131 being coupled to same. As described above, said second suture 131 is used to interleave additional sutures through the same (see FIG. 64).

Figure 65A:
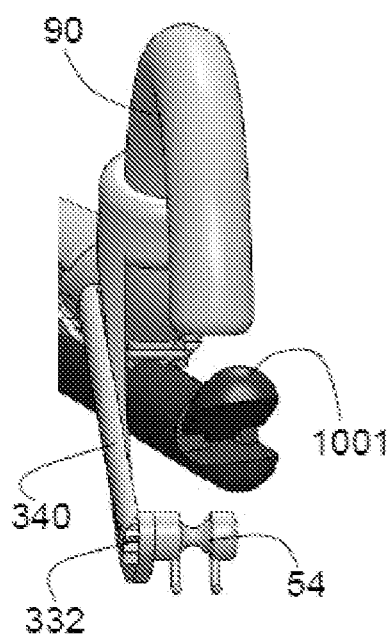
FIG. 65 illustrates an embodiment of the invention in which asymmetric support is provided to support element 54.
Figure 65B:
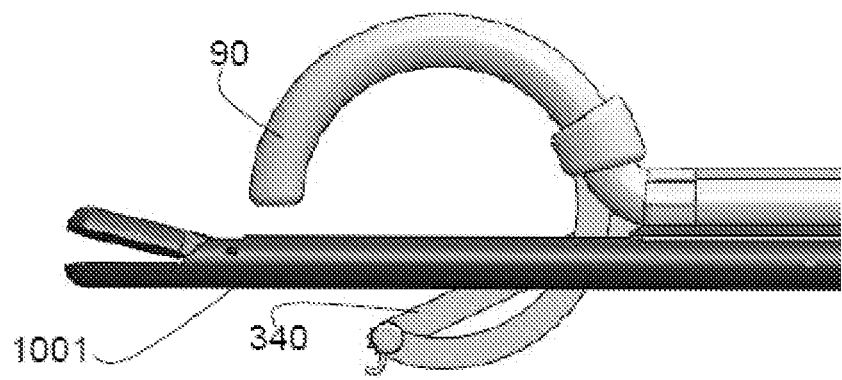
Figure 65C:
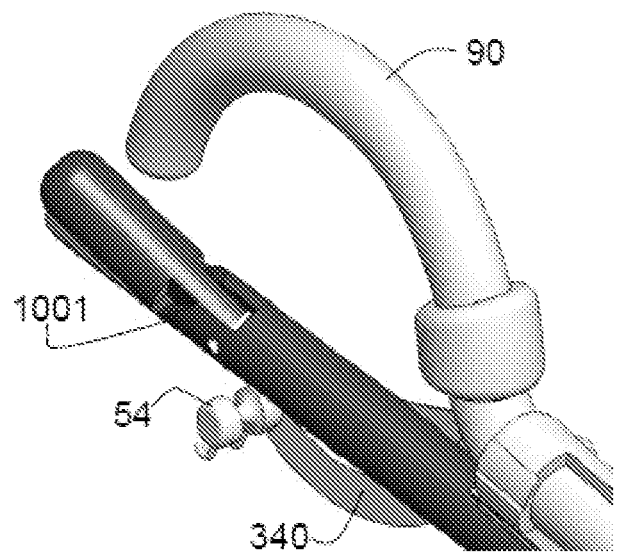

Reference is now made to FIG. 65, which shows an alternative architecture for yoke 340 according to some embodiments of the invention. In these embodiments, the yoke provides asymmetric support to support element 54. Rather than being constructed in a generally fork-like configuration, the yoke comprises only one prong, on one side only of head 90. The single prong is connected to support element 54 by a single connector 332. FIG. 65A provides a front view of a typical non-limiting configuration in which asymmetrical support is provided. Embodiments in which such asymmetrical support is provided have the advantage that they leave more room for surgical tool 1001 (e.g., grasper), thus allowing the use of the invention with a wider variety of surgical tools than is possible with symmetrical support. FIG. 65B shows a view from the side opposite that with the prong, showing how surgical tool 1001 passes through the distal end of the instrument. In the embodiment illustrated in FIG. 65B, the surgical tool is a grasper, but it will be well-understood by those skilled in the art than any appropriate surgical tool may be used. FIG. 65C presents a top view of the distal end of the instrument in the same embodiment, illustrating the positioning of the surgical tool relative to support element 54 and yoke 340.

Figure 70:
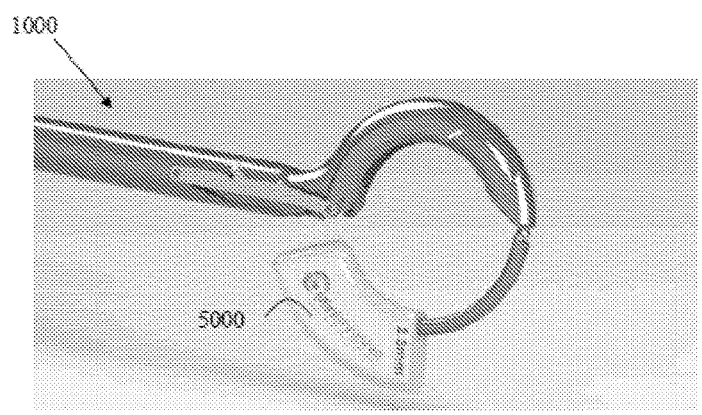
FIG. 70 illustrates an embodiment utilizing a single use needle cartridge 5000.

According to another embodiment of the present invention, a single use needle cartridge 5000 is provided. The single use needle cartridge 5000 may be specifically selected per every patient and coupled to the reusable circular bone tunneling device 1000 of the present invention. Reference is now made to FIG. 70 illustrating the single use needle cartridge 5000 and the coupling of the same to the circular bone tunneling device 1000 of the present invention.

Figure 71A:
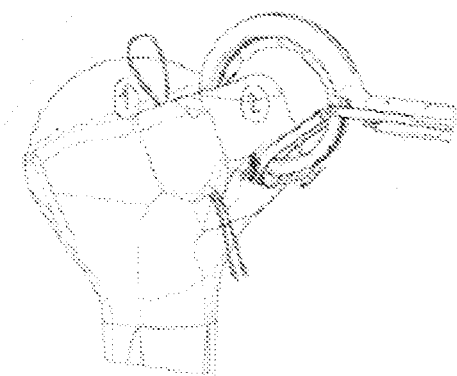
FIGS. 71a-71b illustrate the circular bone tunneling device utilized as a sewing machine.
Figure 71B:
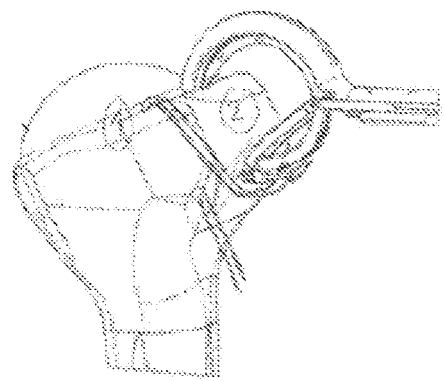
Figure 72:
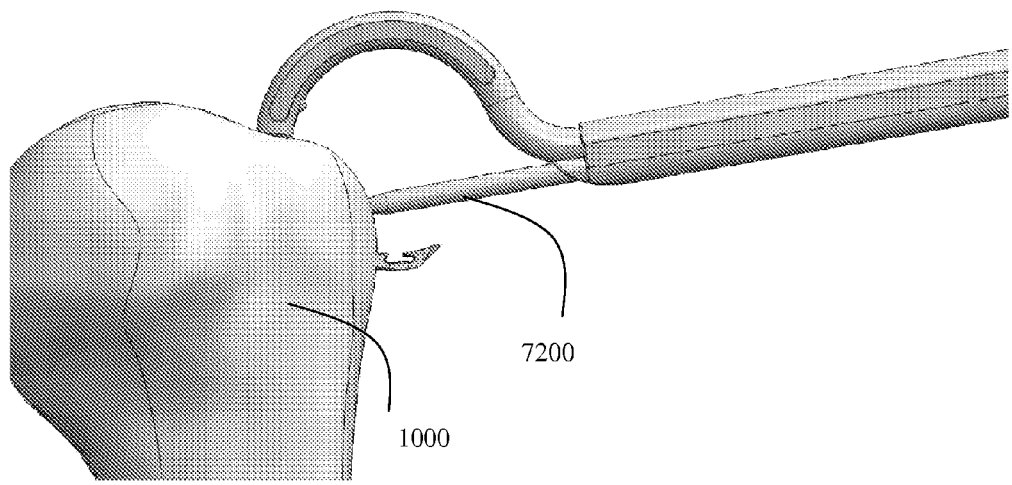
FIGS. 72-78 illustrate another embodiment of the present invention, in which a stabilizing element 7200 is provided.
Figure 73:
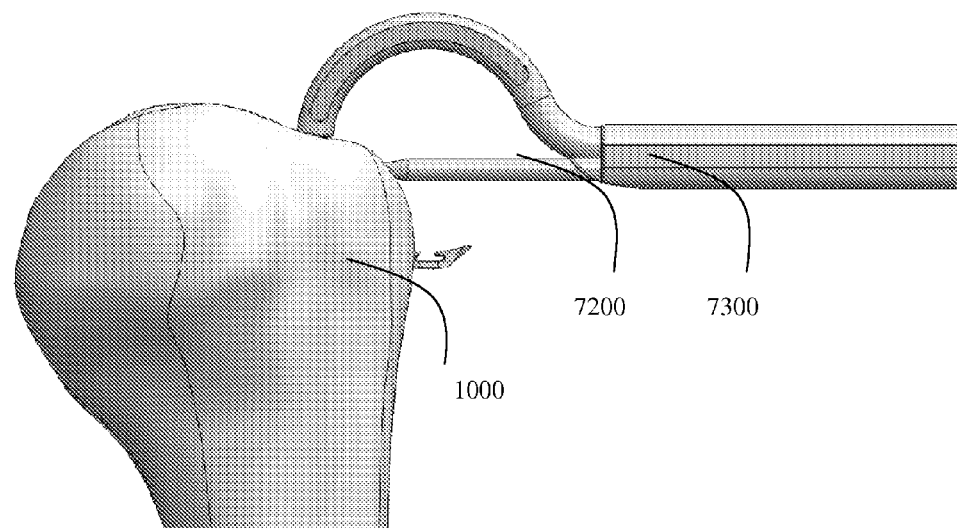
Figure 74:
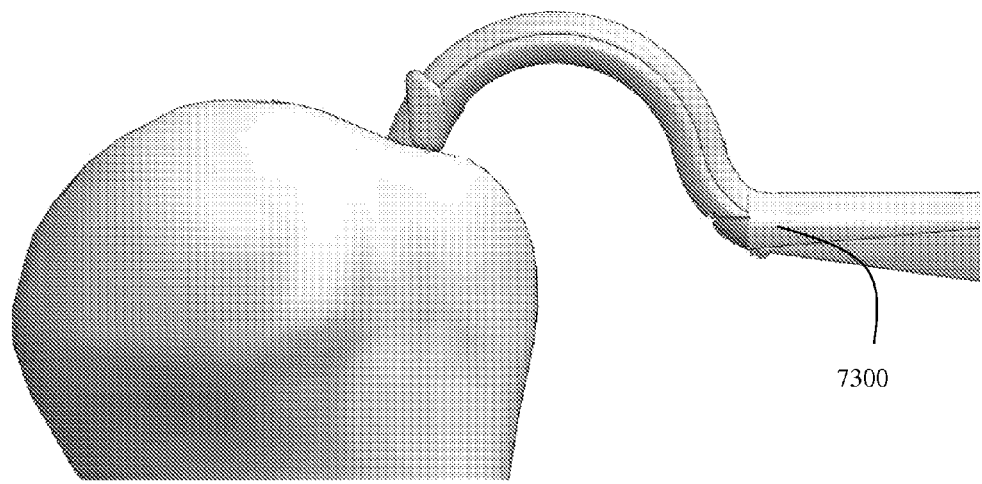

According to another embodiment of the present invention, the circular bone tunneling device of the present invention can be utilized as a sewing machine. Reference is now made to FIGS. 71*a*-71*b* illustrating the above mentioned embodiment.

According to this embodiment, a suture that was threaded into a first tunnel (illustrated in FIGS. 71*a*-71*b* as numerical reference "1") can be coupled to the circular bone tunneling device's needle, once the same has tunnel through the tendon and the bone a second tunnel (illustrated in FIGS. 71*a*-71*b* as numerical reference "2").

The coupling of the suture to the circular bone tunneling device's needle can be obtained manually by means of e.g., a grasper.

It should be pointed out that the above mentioned first tunnel (illustrated in FIGS. 71*a*-71*b* as numerical reference "1") can be provided by the circular bone tunneling device of the present invention 1000.

Another issue which is of extreme importance is the ability to stabilize and fixate the device of the present invention in a predetermined position and orientation relative to the bone. The same is provided by "grabbing" and firmly holding the bone at two different points along an arc and then stabilizing the device relative to the bone by a stabilizing element (that reduces the movement, degrees of freedom). The stabilizing element reduces the device's degrees of freedom fixating the device to the bone at a third contact point such that movement is minimized and the forces applied to the needle will be facilitated to be able to drive into the bone and further inadvertent movement by the physician due to hand movements will not affect the position of the device.

It is to be understood that unintentional movement of the needle (or the entire device) can lead the needle to penetrate the bone at the wrong angle and/or in the wrong position; and therefore cause excess damage to the bone.

Furthermore, incorrect angular penetration may well lead to a poor clinical outcome.

Such provision of angular fixation ensures that the device will be maintained in a constant position and orientation relative to the bone so as to enable the needle to penetrate with the proper angular orientation and at the proper position relative to the bone and without any undesired movements (namely angular movements) of the device.

Reference is now made to FIGS. 72-78 illustrating the above mentioned embodiment of the present invention. According to this embodiment, a stabilizing element 7200 is provided.

According to this embodiment, the stabilizing element 7200 is adapted to be in physical contact with said bone so as to fixate the orientation and position of the circular bone tunneling device relative to said bone.

According to another embodiment of the present invention the stabilizing element 7200 is characterized by at least one extended configuration (see FIGS. 72-73), in which said stabilizing element 7200 extends out of the hollow elongate body 7300, and at least one retracted configuration (see FIG. 74), in which said stabilizing element 7200 is encased within the hollow elongate body 7300. It is within the provision of the present invention wherein said stabilizing element 7200 is reconfigurable from said extended configuration to said retracted configuration and vice versa.

According to one embodiment of the present invention said reconfiguration of said stabilizing element from said extended configuration to said retracted configuration and vice versa is provided by reciprocally moving said stabilizing element along the main longitudinal axis of the circular bone tunneling device.

According to one embodiment of the present invention the stabilizing element 7200 is pivotally coupled, at a pivot point, to the distal end of the hollow elongate body 7300 at a pivot point. According to this embodiment, said reconfiguration of said stabilizing element from said extended configuration to said retracted configuration and vice versa is provided by radially and pivotably rotating the stabilizing element 7200 around said pivot point.

According to one embodiment of the present invention, the stabilizing element 7200 is merely in physical contact with the bone 1000. Said physical contact provides said fixation of the device relative to said bone.

Figure 75:
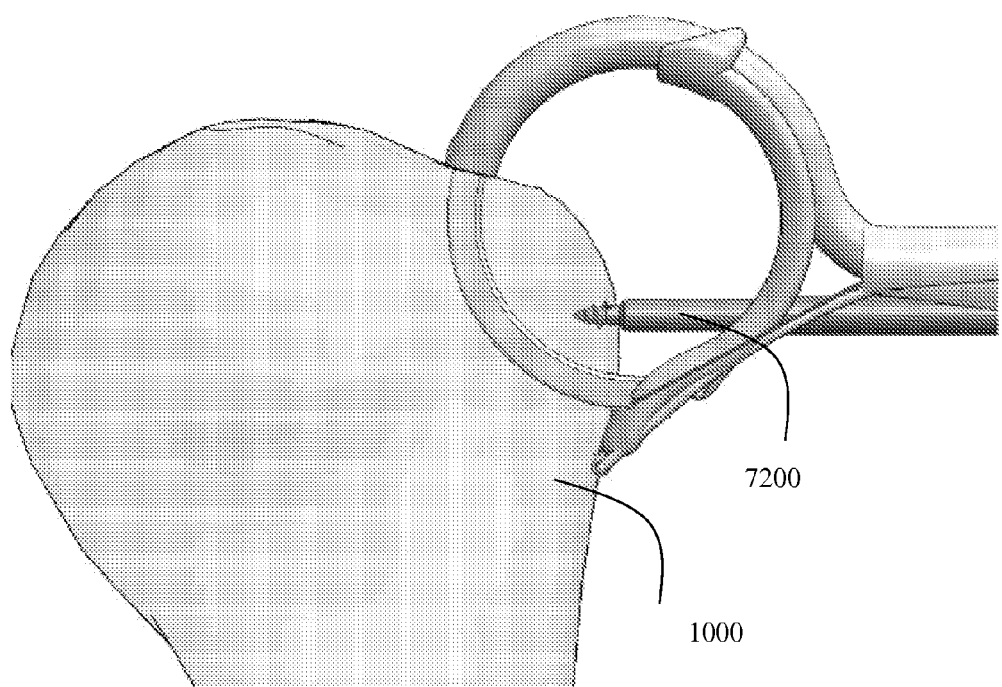
Figure 76:
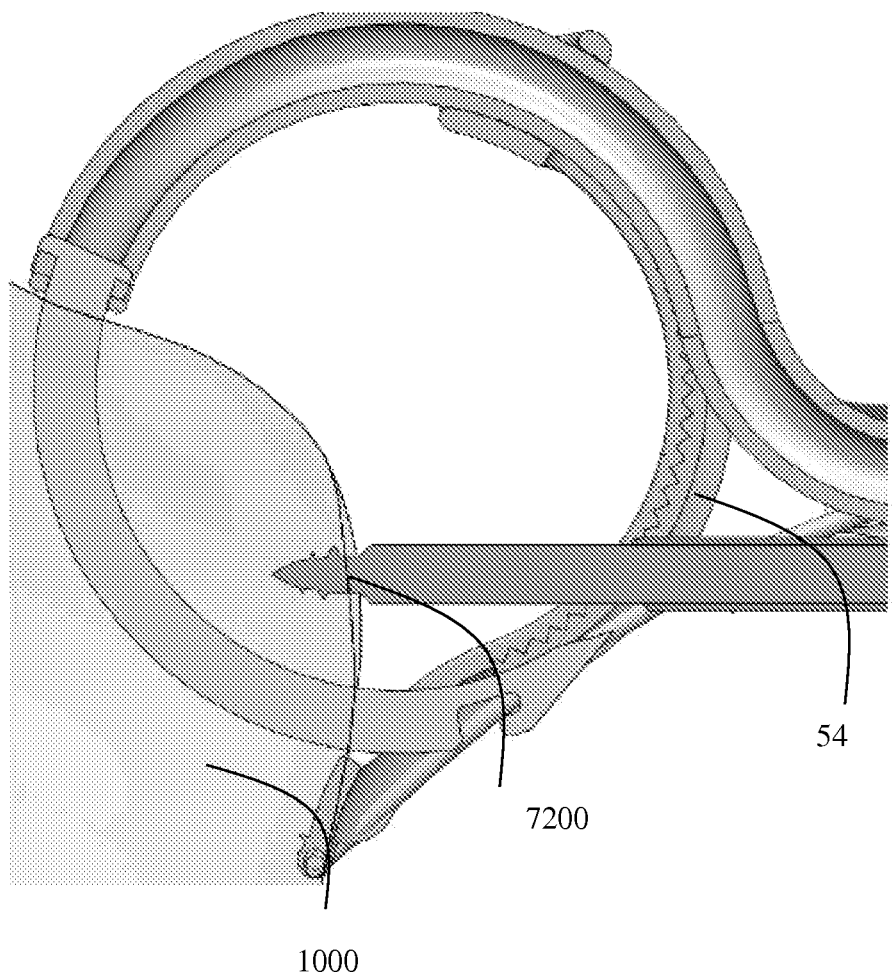

According to another embodiment of the present invention, the stabilizing element 7200 is anchored within the bone 1000 (see FIGS. 75-76, for example).

Reference is now made to FIGS. 75-76 which illustrates the stabilizing element 7200 in the extended configuration and the support element 54 in the extended configuration. In this position the device is fixated in its orientation to the bone.

Figure 77:
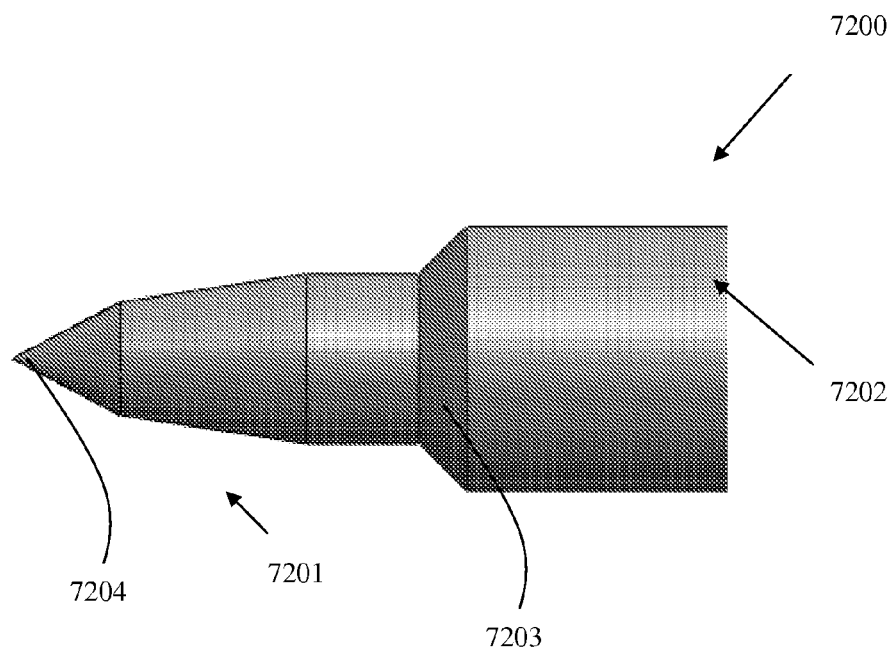
Figure 78:
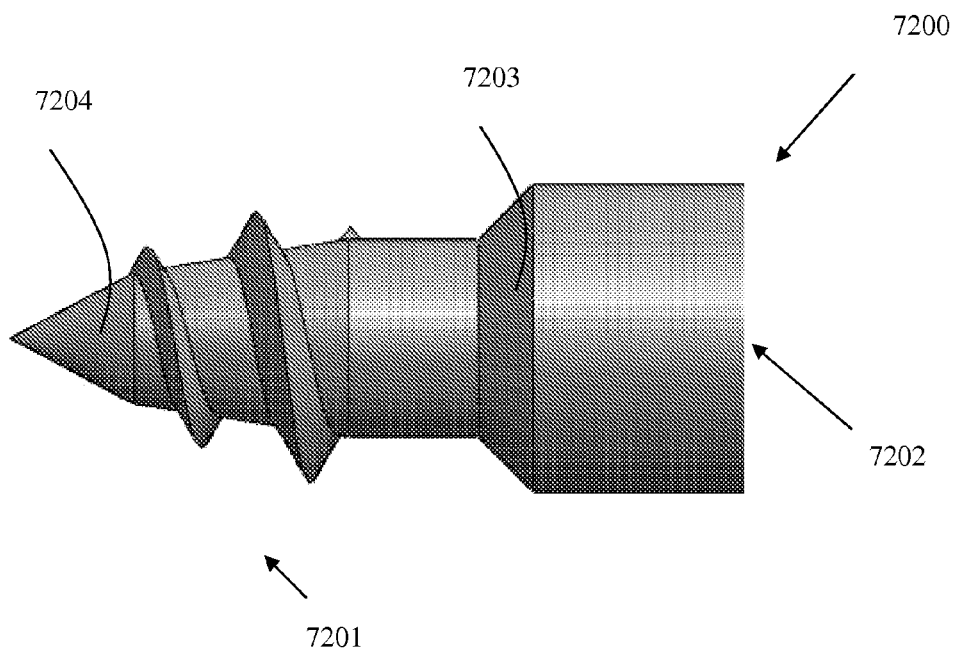
Figure 79:
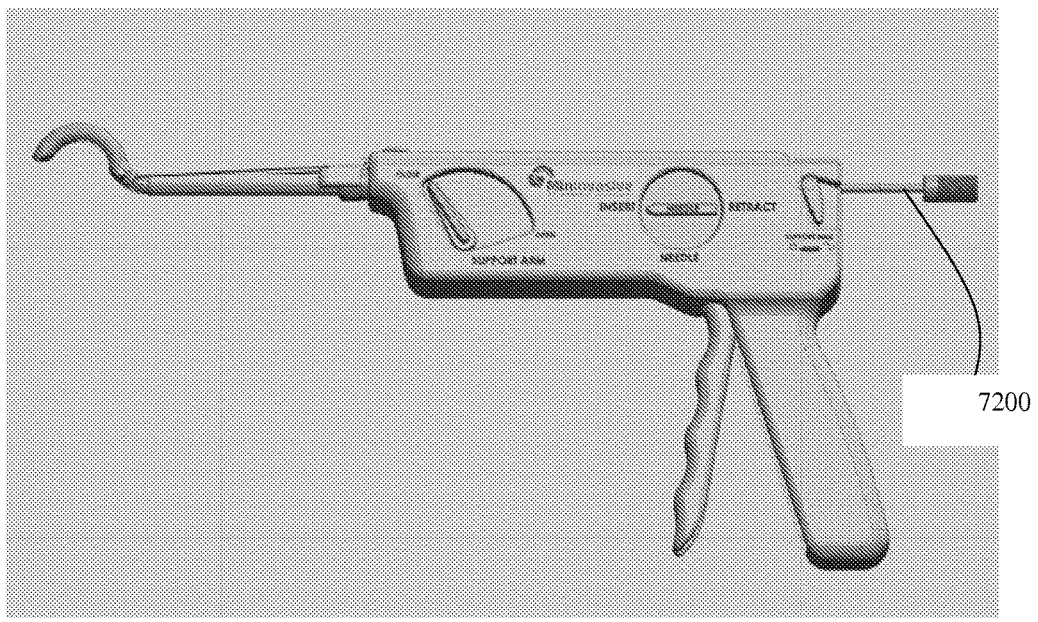
FIGS. 79-85 illustrate another embodiment of the stabilizing element 7200.

Reference is now made to FIGS. 77-78 providing a closer look at the stabilizing element 7200.

As can be seen in the FIGS., the stabilizing element 7200 is characterized by a distal end 7201 and a proximal end 7202.

According to said embodiment the distal end 7201 comprises a flange 7203 and a tip 7204. Tip 7204 is adapted to penetrate the bone 1000 and to anchor the stabilizing element within the same.

Flange 7203 adapted to limit the penetration of the stabilizing element 7200 into the bone. In other words, the stabilizing element 7200 is adapted to prevent the insertion of the proximal end 7202 of the stabilizing element 7200 into said bone 1000 such that only said tip 7204 is anchored within said bone 1000.

According to another embodiment of the present invention, the tip 7204 of the stabilizing element 7200 may have different shapes. One example is a nail-like tip (see FIG. 77); while another embodiment is a screw-like tip (see FIG. 78). Of course said shapes can be altered and are not limited to the ones disclosed above.

Reference is now made to FIGS. 79-85 illustrating another embodiment of the stabilizing element 7200.

As mentioned above, the stabilizing element 7200 is introduced through the hollow elongate body 7300 of the device and adapted to reciprocally move along the main longitudinal axis of the hollow elongate body 7300 of the device.

Figure 80:
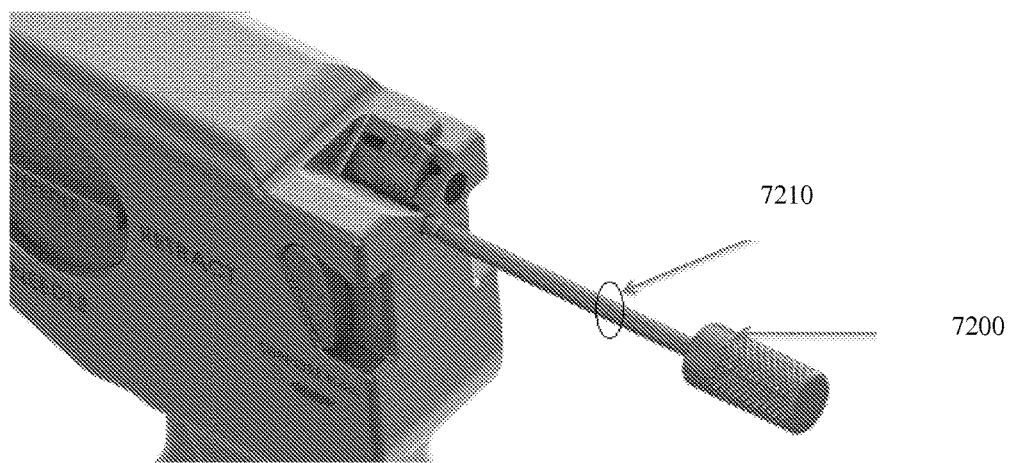

According to another embodiment, the stabilizing element 7200 comprises at least one marker 7210 on the same (see FIG. 80). Preferably said marker 7210 is engraved on the stabilizing element 7200.

Marker 7210 is adapted to indicate the contact point of the stabilizing element 7200 with the bone 1000 (i.e., that the stabilizing element 7200 has come into physical contact with the bone, as the same is further advanced through the hollow elongate body 7300 of the device). In other words, the marker 7210 verifies/informs the user as for the current position of the stabilizing element 7200 with respect to the bone.

Figure 81:
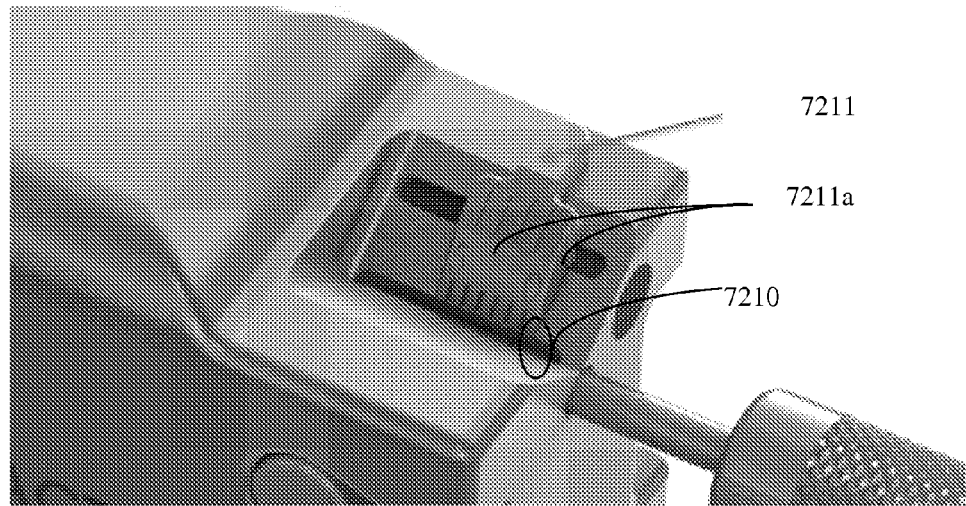

According to another embodiment, a second indicator 7211 is provided, see FIG. 81.

Indicator 7211 is provided with a ruler or a yardstick having numerical references 7211a staring from 0 to at least 5. Said numerical references 7211a are adapted to indicate the user how far the stabilizing element 7200 has penetrated the bone 1000. For example, if the second indicator 7211 indicates 0, thus the stabilizing element 7200 has not penetrated the bone at all but is in contact with the same. If the second indicator 7211 indicates 5, thus the stabilizing element 7200 has penetrated 5 mm into the bone.

The indication provided by the second indicator 7211 is provided by the integration and the intersection between the engraved marker 7210 and the numerical references 7211a on the second indicator 7211.

Figure 82:
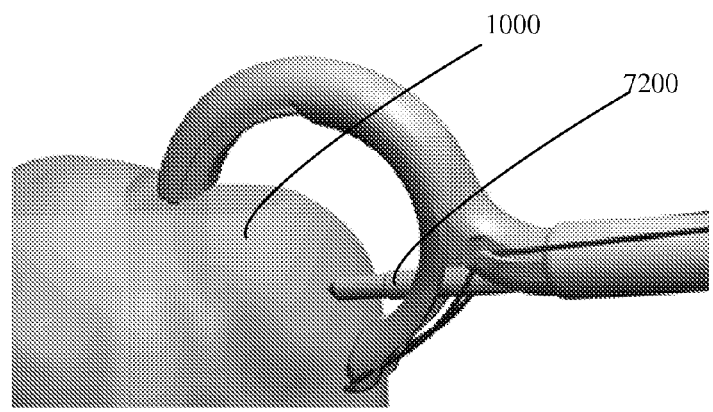
Figure 83:
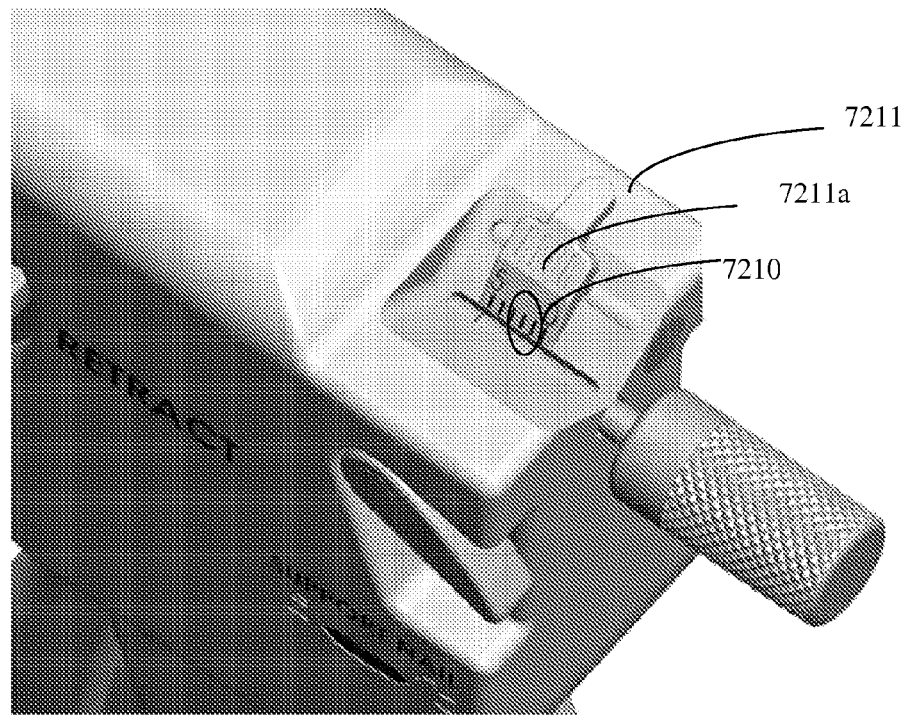

FIG. 82 illustrates the stabilizing element 7200 when the same is in physical contact with the bone 1000. i.e., when indicator 7211 indicates '0'.

Figure 84:
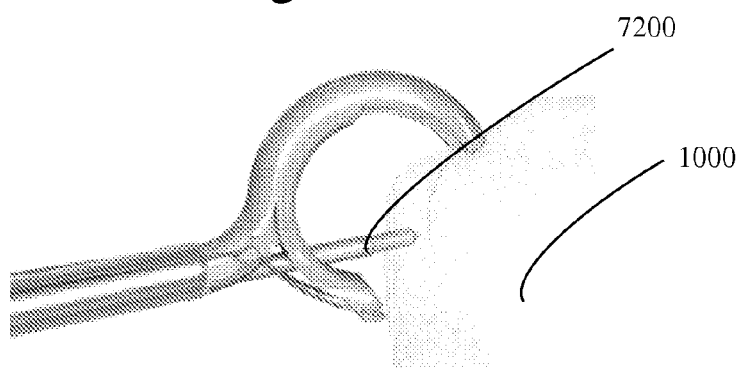

When indicator 7211 indicates '5' (see FIG. 83), the stabilizing element 7200 has penetrated the bone 1000 5 mm (see FIG. 84).

Figure 85:
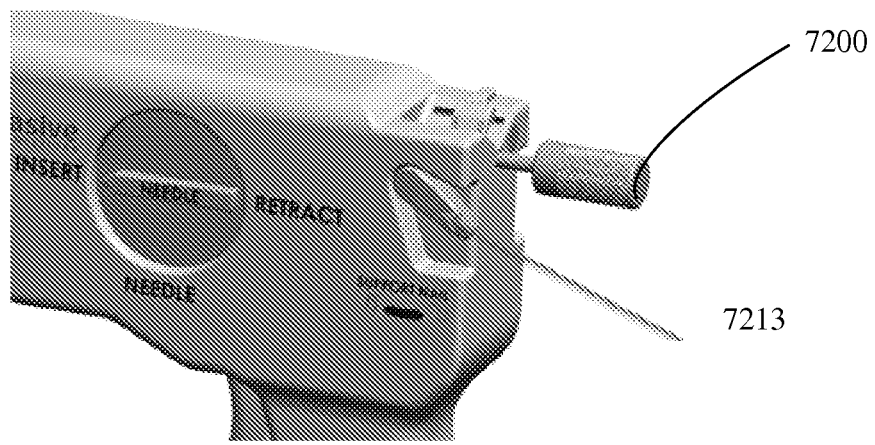

Reference is now made to FIG. 85 illustrating yet another embodiment of the present invention. According to this embodiment, the device of the present invention further comprises a locking mechanism 7213 adapted to lock the stabilizing element 7200 is position.

In light of the above disclosure, the circular bone tunneling device of the present invention comprises inherently each of the following advantages:

(a) the circular bone tunneling device of the present invention penetrates tendon and bone in a single step. The needle creates a tunnel through the tendon and the bone in said single step.

(b) the circular bone tunneling device of the present invention has a unique needle that penetrates the tendon, the bone, automatically catches the suture and withdraws the same all the way back. In other words, there is only one step for both the tunneling and the suture passage.

(c) With the circular bone tunneling device of the present invention, the physician penetrates from one entry point to second exit point forming a circular tunnel (one tunnel only).

(d) The circular bone tunneling device of the present invention has a specially adapted cartridge that threads the suture passed through the bone and the tendon by actuating the integral elements of the device designed to thread and feed the suture into the tunnel and through the ligament. This is in sharp contrast to commonly used devices which are not adapted to thread the suture but rather "a temporary suture" or a guide suture which is used to shuttle the final sutures through the tunnel.

(e) The circular bone tunneling device of the present invention is adapted to penetrate varying diameter bones and bone structures and can create tunnels of varying lengths specifically adapted to the various geometries of different bones in different locations and sizes. Due to its unique extendable and retractable support element (that can be opened to different sizes), the tunnel length is varied and the device is adapted for different bone size or different clinical needs.

(f) The circular bone tunneling device of the present invention has a working channel throughout which one can pass various working tools required (e.g. a Cartridge, Grasper, Manipulator a JIG or any other device).

(g) The circular bone tunneling device of the present invention has external indicators that enable the surgeon to understand where the needle and the support arm are located at any given time along the procedure.

(h) The circular bone tunneling device of the present invention may be fixated in its position relatively to the bone throughout at least a portion of the procedure (by means of the stabilizing element). Alternatively the circular bone tunneling device may be fixated in its position relatively to the bone throughout the entire procedure. In either case, such provision ensures that the device will be maintained at a constant position relatively to the bone so as to enable the needle to penetrate the bone without any undesired movements (e.g., angular movements) of the same.

It should be emphasized that each of the above can be carried out independently or any combination can be used in the circular bone tunneling device.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

We claim:

1. A circular bone tunneling device, for use in arthroscopic surgery, comprising:

a hollow elongate body including a hollow elongate body head, said hollow elongate body head defining a rigid circular arc, said hollow elongate body head including a surgical needle adapted to tunnel through a bone along a path formed by said rigid circular arc, thereby forming a transosseous tunnel through said bone; and a suture cartridge including a suture located at a predetermined location of said suture cartridge;

said surgical needle including a suture engagement portion, adjacent a distal end thereof, adapted to engage said suture and to catch said suture from said predetermined location after said surgical needle has formed said transosseous tunnel, and, upon retraction of said surgical needle through said transosseous tunnel, to draw said suture through said transosseous tunnel.

2. The circular bone tunneling device according to claim 1, further comprising a shaft including an inner elongated hollow tube.

3. The circular bone tunneling device according to claim 1, wherein said surgical needle is a rigid surgical needle.

4. The circular bone tunneling device according to claim 1, further comprising a needle control adapted to advance and retract said surgical needle through said bone.

5. The circular bone tunneling device according to claim 1 and wherein said suture cartridge comprises an external scaffold.

6. The circular bone tunneling device according to claim 5 and wherein said suture is disposed along an outer circumference of said scaffold.

7. The circular bone tunneling device according to claim 1 and wherein said suture cartridge includes an inner body.

8. The circular bone tunneling device according to claim 7 and wherein said inner body is utilizable as a working channel.

* * * * *